United States Patent
Muenks et al.

(10) Patent No.: US 10,258,040 B2
(45) Date of Patent: Apr. 16, 2019

(54) USE OF COMBINATIONS COMPRISING HOST DEFENSE INDUCERS AND BIOLOGICAL CONTROL AGENTS FOR CONTROLLING BACTERIAL HARMFUL ORGANISMS IN USEFUL PLANTS

(71) Applicant: Bayer CropScience Aktiengesellschaft, Monheim am Rhein (DE)

(72) Inventors: Karl-Wilhelm Muenks, Carmichael, CA (US); Rolf Christian Becker, Burscheid (DE); Friedrich Kerz-Moehlendick, Leverkusen (DE); Bernd Springer, Köln (DE); Lino Miguel Dias, Leverkusen (DE); Coralie Nicole Van Breukelen-Groeneveld, Neuss (DE); Gilbert Labourdette, Paray le Monial (FR); Denise Manker, Davis, CA (US)

(73) Assignee: Bayer CropScience Aktiengesellschaft, Monheim am Rhein (DE)

(*) Notice: Subject to any disclaimer, the term of this patent is extended or adjusted under 35 U.S.C. 154(b) by 0 days.

(21) Appl. No.: 14/903,336

(22) PCT Filed: Jul. 10, 2014

(86) PCT No.: PCT/EP2014/064873
§ 371 (c)(1),
(2) Date: Jan. 7, 2016

(87) PCT Pub. No.: WO2015/004260
PCT Pub. Date: Jan. 15, 2015

(65) Prior Publication Data
US 2016/0374341 A1    Dec. 29, 2016

Related U.S. Application Data

(60) Provisional application No. 61/859,467, filed on Jul. 29, 2013.

(30) Foreign Application Priority Data

Jul. 11, 2013   (EP) ..................... 13176096

(51) Int. Cl.
*A01N 43/80* (2006.01)
*A01N 63/00* (2006.01)

(52) U.S. Cl.
CPC ............. *A01N 43/80* (2013.01); *A01N 63/00* (2013.01)

(58) Field of Classification Search
None
See application file for complete search history.

(56) References Cited

U.S. PATENT DOCUMENTS 9,364,006 B2   6/2016   Wachendorff-Neumann et al.

FOREIGN PATENT DOCUMENTS

| WO | 2009/124707 A2 | 10/2009 |
| WO | 2010/128003 A2 | 11/2010 |
| WO | WO 2010/139656 | * 12/2010 |
| WO | 2011/114280 A2 | 9/2011 |
| WO | 2012/087980 A1 | 6/2012 |

OTHER PUBLICATIONS

Zeriouh et al., Mol Plant Microbe Interact., 2011, vol. 24, No. 12, p. 1540-1552.*
Han et al., Journal of Applied Microbiology, 2005, vol. 99, p. 213-221.*
Agraquest, Inc: Technical Sheet for Serenade® Max—Fire Blight Protection You Can Count on with Serenade: 2006.
Agraquest, Inc: Technical Sheet for Serenade®—For Proven Control of Fire Blight in Apples: Apr. 2007.
Agraquest, Inc: Technical Sheet for Serenade® Max—Proven Fire Blight Control on Apples: Apr. 2008.
Chithrashree, et al., "Plant Growth Promoting Rhizobacteria Mediate Induced Systemic Resistance in Rice Against Bacterial Leaf Blight Caused by *Xanthomonas oryzae* pv. *oryzae*," Biological Control, 2011, vol. 59, pp. 114-122.
Gilardi, G., et al., "Evaluation of Spray Programmes for the Management of Leaf Spot Incited by *Pseudomonas syringae* pv. *syringae* on tomato cv. *Cuore di bue*," Crop Protection, 2010, vol. 29, pp. 330-335.

(Continued)

*Primary Examiner* — Kade Ariani
(74) *Attorney, Agent, or Firm* — Adam L. Lunceford; Michelle L. Samonek

(57) ABSTRACT

The present invention relates to the use of a combination comprising at least one host defense inducer and at least one biological control agent in a synergistically effective amount for controlling bacterial harmful organisms in useful plants. The biological control agent is selected from specific microorganisms and/or a mutant of these strains having all the identifying characteristics of the respective strain, and/or a metabolite produced by the respective strain. In a preferred aspect of the invention the host defense inducer is isotianil or a combination of isotianil and acibenzolar-S-methyl. The present invention also relates to a method for controlling bacterial harmful organisms in useful plants by treatment with a combination comprising at least one host defense inducer and at least one biological control agent in a synergistically effective amount. A further aspect of the present invention is directed to method for controlling bacterial harmful organisms in useful plants by subjecting the plants to be protected against attack by bacterial harmful organisms to two or more sequential treatment blocks.

17 Claims, No Drawings

(56) References Cited

OTHER PUBLICATIONS

Ishida, A. K.N., et al., "Rhizobacterium and Acibenzolar-S-methyl (ASM) in Resistance Induction Against Bacterial Blight and Expression of Defense Responses in Cotton," Tropical Plant Pathology, 2008, vol. 33, pp. 027-034.

Marschall, K., et al., "Feuerbrandversuche auf der Laimburg," Obstbau Weinbau, Apr. 1, 2008, pp. 108-111.

Myresiotis, C.K., et al., "Biodegradation of Soil-Applied Pesticides by Selected Strains of Plant Growth-Promoting Rhizobacteria (PGPR) and Their Effects on Bacterial Growth," Biodegradation, 2012, vol. 23, pp. 297-310.

Ogawa, M., et al., "Applied Development of a Novel Fungicide Isotianil (Stout®)," Sumitomu Kagaku, R&D Report, May 31, 2011, pp. 1-16.

Parkunan, V., Induced Disease Resistance Elicited by Acibenzolar-S-methyl and Plant Growth-Promoting Rhizobacteria in Tobacco (*Nicotiana tabacum* L.), Dissertation submitted to the Faculty of the Virginia Polytechnic Institute and State University for the degree of Doctor of Philosophy in Plant Pathology, Physiology and Weed Science, Sep. 15, 2008, pp. 1-188.

Parkunan, V., et al., "Influence of Acibenzolar-S-methyl and Mixture of *Bacillus* Species on Growth and Vigor of cultivated Tobacco," Tobacco Science, Jan. 1, 2011, pp. 7-14.

International Search Report and Written Opinion of the International Searching Authority, International Patent Application No. PCT/EP2014/064873, dated Sep. 8, 2014, pp. 1-16.

Alexander, S.A., et al., "Evaluation of Fungicides for Control of Bacterial Spot and Septoria Leaf Spot in Staked Tomatoes," F&N Tests, 2001, vol. 57:V10.

\* cited by examiner

USE OF COMBINATIONS COMPRISING HOST DEFENSE INDUCERS AND BIOLOGICAL CONTROL AGENTS FOR CONTROLLING BACTERIAL HARMFUL ORGANISMS IN USEFUL PLANTS

CROSS-REFERENCE TO RELATED APPLICATION(S)

The present application is a 35 U.S.C. § 371 national stage entry of PCT/EP2014/064873, filed on Jul. 10, 2014, which claims priority to European Patent Application No. 13176096.9, filed on Jul. 11, 2013, and also which claims priority to U.S. Patent Application No. 61/859,467, filed Jul. 29, 2013, the contents of which are hereby incorporated by reference in their entirety. Applicant claims priority to each of the foregoing patent applications. The PCT International Application was published in the English language.

The present invention relates to the use of a combination comprising at least one host defense inducer and at least one biological control agent in a synergistically effective amount for controlling bacterial harmful organisms in useful plants. The biological control agent is selected from specific microorganisms and/or a mutant of these strains having all the identifying characteristics of the respective strain, and/or a metabolite produced by the respective strain. In a preferred aspect of the invention the host defense inducer is isotianil or a combination of isotianil and acibenzolar-S-methyl. The present invention also relates to a method for controlling bacterial harmful organisms in useful plants by treatment with a combination comprising at least one host defense inducer and at least one biological control agent in a synergistically effective amount. A further aspect of the present invention is directed to method for controlling bacterial harmful organisms in useful plants by subjecting the plants to be protected against attack by bacterial harmful organisms to two or more sequential treatment blocks.

INTRODUCTION AND PRIOR ART

International patent application WO 2010/089055 A2 and the corresponding European patent application EP 2393363 A2 generally disclose the use of sulphur-containing heteroaromatic acid analogues according to a general formula (I) for controlling bacterial harmful organisms in useful plants. The general formula (I) encompasses inter alia the host defense inducers tiadinil (compound I-1) and isotianil (compound I-15) out of a list of 20 different preferred specific compounds. The host defense inducer acibenzolar-S-methyl and probenazole are not comprised by formula (I). Further, the application broadly refers to various bacteria strains and to diverse plants to be treated. The application specifically only refers to one concrete example, wherein the use of compound 1-15 (isotianil) in the treatment of rice against *Xanthomonas campestris* pv. *oryzae* is described. The use of a combination comprising at least one of such host defense inducers and at least one biological control agent in a synergistically effective amount for controlling bacterial harmful organisms in useful plants is not described in WO 2010/089055 A2. The inventors of the present invention surprisingly found the beneficial synergistic effects of such combinations in combating bacterial harmful organisms in plants.

The unpublished patent application PCT/EP2013/050772 of the present applicant relates to the use of host defense inducers, preferably isotianil, for controlling selected bacterial harmful organisms in selected useful plants and can be considered as a selection invention over WO 2010/089055 A2. Combinations comprising a synergistically effective amount of at least one host defense inducer and at least one biological control agent for controlling bacterial harmful organisms in useful plants are not described therein.

International patent application WO 98/21967 A1 and the corresponding U.S. Pat. No. 5,869,042 generally disclose methods of preventing and treating above-ground fungal and bacterial infections in plants by applying an effective amount of at least one biological control agent, e.g. an antibiotic—producing *Bacillus* sp. bacterial strain AQ175 (ATCC Accession No. 55608), AQ 77 (ATCC Accession No. 55609) or AQ178 (ATCC Accession No. 53522) or at least one antibiotic produced by these strains. Combinations of such *Bacillus* sp. bacterial strains with at least one host defense inducer are not mentioned therein.

Further, several unpublished patent applications of the present applicant such as EP 12004160.3, EP 12197956.1, EP 12197951.2, EP 12197949.6, EP 12197945.4, EP 12197942.1, EP 12197941.3, EP 12197939.7, EP 12197141.0, EP 12197131.1, EP 12197132.9, EP 12197134.5, EP 12197135.2, EP 12197137.8, EP 12197139.4, EP 12169936.7 refer to combinations comprising biological control agents, particularly such comprising *Bacillus* sp. bacterial strains, and to combinations of such biological control agents with fungicides and/or insecticides.

Example 13 of WO 98/50422 discloses a synergistic effect of a mixture comprising *Bacillus subtilis* AQ713 (NRRL Accession No. B-21661) and azoxystrobin.

However, none of these patent applications refers to combinations of such *Bacillus* sp. bacterial strains as biological control agent with at least one host defense inducer.

The beneficial synergistic effects and new use of the combination comprising at least one host defense inducer and at least one biological control agent have now been shown by the inventors of the present invention for the first time and were not obviously suggested by the mentioned prior art.

Bacteria as pathogens in useful plants are encountered inter alia in temperate or warm and humid climates, where they cause bacterioses in a large number of useful plants with in some cases considerable economic losses.

Rice, for example, may be infected with *Acidovorax avenae* or *Burkholderia glumae*, causing brown stripe or bacterial grain rot, respectively.

Citrus greening disease (Huanglongbing, HLB, citrus vein phloem degeneration (CVPD), yellow shoot disease, leaf mottle yellow (in the Philippines), libukin (in Taiwan) and citrus dieback (in India)), caused by *Candidatus Liberibacter* spp., is probably the most deleterious disease of citrus and greatly reduces production, destroys the economic value of fruit and can ultimately lead to the death of the entire plant. *Candidatus Liberibacter* spp. is a genus of gram-negative bacteria in the Rhizobiaceae family. Members of the genus are plant pathogens, which are mostly transmitted by psyllids. The disease is distinguished by the common symptoms of yellowing of the veins and adjacent tissues; followed by yellowing or mottling of the entire leaf; followed by premature defoliation, dieback of twigs, decay of feeder rootlets and lateral roots, and decline in vigor; and followed by, ultimately, the death of the entire plant. Affected trees have stunted growth, bear multiple off-season flowers (most of which fall off), and produce small, irregularly-shaped fruit with a thick, pale peel that remains green at the bottom. Fruit from these trees tastes bitter. Infected trees do not recover and there is no curative method existing. The control of HLB is based on the preventive control of the vectors using systemic insecticides and contact insecticides. However, the efficacy and activity spectrum of these compounds are not always completely satisfactory. Newly infected trees show the first symptoms after a latency period of 6-12 months. In addition, it is essential to eradicate infected trees to prevent further uptake by psyllids and spreading of the disease. There is no cure for Huanglongbing and efforts to control the disease have been slow because infected citrus plants are difficult to maintain, regenerate, and study. Researchers at the Agricultural Research Service have used Huanglongbing-infected lemon trees to infect periwinkle plants in an effort to study the disease. Periwinkle plants are easily infected with the disease and respond well when experimentally treated with antibiotics. Researchers are testing the effect of penicillin G sodium and the biocide 2,2-dibromo-3-nitrilopropionamide as potential treatments for infected citrus plants based on the positive results that were observed when applied to infected periwinkle. HLB bacteria live and multiply exclusively in the phloem of citrus trees. Hitherto, there are however only few bactericides for the curative control of HLB, e.g. the international application WO 2011/029536 A2 refers to the use of cyclic ketoenols against *Candidatus liberibacter* spp.

Citrus canker is a disease affecting citrus species that is caused by the bacterium *Xanthomonas axonopodis* pv. *citri* (=*Xanthomonas campestris* pv. *citri*). Infection causes lesions on the leaves, stems, and fruit of citrus trees, including lime, oranges, and grapefruit. While not harmful to humans, canker significantly affects the vitality of citrus trees, causing leaves and fruit to drop prematurely; a fruit infected with canker is safe to eat but too unsightly to be sold. The impact is worsened because the presence of citrus canker in an area triggers immediate quarantine restrictions, disrupting the movement of fresh fruit. Citrus canker is believed to have originated in the area of Southeast Asia-India. It is now also present in Japan, South and Central Africa, the Middle East, Bangladesh, the Pacific Islands, some countries in South America, and Florida. Some areas of the world have eradicated citrus canker and others have ongoing eradication programs (citrus groves have been destroyed in attempts to eradicate the disease), but the disease remains endemic in most areas where it has appeared. Because of its rapid spread, high potential for damage and impact on export sales and domestic trade, citrus canker is a significant threat to all citrus-growing regions.

Citrus variegated chlorosis (CVC) is a further citrus disease affecting citrus plants throughout South America, in particular Brazil. CVC is caused by the bacterium *Xylella fastidiosa* from the family of Xanthomonadaceae. CVC is a systemic disease that only survives in plant xylem or within its vector. *X. fastidiosa* has been shown to move from seed to seedling in sweet orange. CVC has a latency period of 9-12 months before symptoms occur. Natural spread of *X. fastidiosa* occurs by several species of sharpshooter leafhoppers in the order Hemiptera. The kiwifruit industry is widely affected by *Pseudomonas* ssp. infections, e.g. infection with *Pseudomonas syringae* pv. *actinidae* (Psa) was first identified in New Zealand and in Japan and Italy, too, where it is extremely damaging on Gold kiwifruit. Presently, intensive research and testing of possible solutions against Psa damage in kiwi fruits are carried out.

Potato tuber Bacterial scab (Common scab) is an emerging issue in core potato growing areas which badly affects the tuber quality. The effected potato tubers are graded as low quality and achieve low prices in the market and in case of high infestation the potatoes are difficult to sell. It is general perception of the farmer that the disease is increasing every year.

Infection with *Erwinia* species, for example, may cause the death of entire fruit plantations such as apples or pears. Also known is bacterial soft rot in potatoes, tumour formation in plants caused by infection with agrobacteria and also a large number of necrotic diseases when cereals such as wheat or rice, vegetables or citrus fruit are infected by *Xanthomonas* species.

Bacterioses caused by *Pseudomonas* species in particular in vegetables, tree fruits and tobacco are considered as particularly destructive.

The standard treatment against bacterial harmful organisms comprises the use of synthetic chemical pesticides and in particular the use of (conventional) antibiotics, which are usually of synthetic or semi-synthetic origin or of natural origin, being isolated from living organisms and prufied or genetically engineered. Examples of such conventional antibiotics comprise e.g. streptomycin, blasticidin S or kasugamycin. The application of such conventional antibiotics is, in principle, the only effective way for controlling bacteria in useful plants. However, this approach is adopted only in rare cases since these antibiotics rely on the same mechanisms of action as antibiotics used in human and veterinary medicine, and there are therefore huge reservations against the use of antibiotics in plant protection. There are concerns that the formation of resistance is promoted; moreover, most conventional antibiotics are expensive and can frequently only be obtained by employing biotechnological methods, inter alia.

Synthetic and semi-synthetic pesticides such as synthetic or semi-synthetic antibiotics are often non-specific and therefore can act on organisms other than the target ones, including other naturally occurring beneficial organisms. Because of their chemical nature, they may be also toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i. e. synthetic) pesticides. Thus, there is a need to manage food chain requirements while still allowing effective pest control.

A further problem arising with the use of synthetic antibiotics is that the repeated and exclusive application of such conventional antibiotics often leads to selection of resistant microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The risk of resistance development in pathogen populations as well as environmental and human health concerns have fostered interest in identifying alternatives to conventional antibiotics for managing plant diseases. The use of biological control agents (biological control agents) is one alternative. However, the effectiveness of most biological control agents is not at the same level as for conventional antibiotics, especially in case of severe infection pressure. Consequently, known biological control agents, their mutants and metabolites produced by them are, in particular in low application rates, not entirely satisfactory.

Another approach for controlling bacteria in plant aims at the use of copper oxychloride, which is disadvantageous because of the necessity of high doses to be applied in the standard treatment. Copper oxychloride is e.g. used in controlling *Pseudomonas syringae* for example in the protection of tomatoes. Further, copper oxychloride is discussed as being phytotoxic and its use is more and more restricted as it is known to accumulate in the soil. In addition, copper oxychloride formulations normally leave visible residues on leaves and fruits, which is not appreciated and accepted by consumers.

There is therefore a great need for specific effective methods with improved effects for controlling bacterial diseases in useful plants, which methods furthermore require only small amounts of substance to be applied and, in addition, do not damage the plants or harm human or animal health.

In this context special focus is put on improved bactericidal activity and synergistic effects of such novel combinations as well as on the combination of a fast efficiency besides a long lasting efficiency to provide increased flexibility with regard to the time of application as well as to minimization of the doses of chemical products spread in the environment and reduction of the costs of the treatment.

It has now been found that a combination comprising at least one host defense inducer, such as preferably isotianil or a combination of isotianil and acibenzolar-S-methyl, and at least one biological control agent, such as preferably *Bacillus subtilis* strain QST713/AQ713 (NRRL Accession No. B21661), *Bacillus subtilis* strain AQ153 (NRRL Accession No. 55614), *Bacillus* sp. strain AQ175 (ATCC Accession No. 55608), *Bacillus* sp. strain AQ177 (ATCC Accession No. 55609), and *Bacillus* sp. strain AQ178 (ATCC Accession No. 53522) and *Pseudozyma aphidis* in a synergistically effective amount is particularly suitable for controlling bacterial harmful organisms in useful plants.

Further, it has been found that a method of treating plants comprising subjecting the plants to be protected against attack by bacterial harmful organisms to two or more sequential treatment blocks, where at least one treatment block comprises subjecting the plants to at least one treatment with at least one host defense inducer and at least one treatment block comprises subjecting the plants to at least one treatment with at least one biological control agent is particularly suitable for controlling bacterial harmful organisms in useful plants. According to a preferred embodiment, it has been found that a method of treating plants comprising subjecting the plants to be protected against attack by bacterial harmful organisms to two or more sequential treatment blocks, where at least one treatment block comprises subjecting the plants to at least one treatment with at least one host defense inducer and at least one treatment block comprises subjecting the plants to at least one treatment with at least one biological control agent, with the proviso that the last treatment block comprises subjecting the plants to at least one treatment with at least one biological control agent, is particularly suitable for controlling bacterial harmful organisms in useful plants.

Problem to be Solved

It was the object of the present invention to provide novel active compound combinations with superior effects in controlling bacterial harmful organisms in useful plants and to provide a new method of treatment.

DESCRIPTION OF THE INVENTION

The problem underlying the present invention has been solved by providing novel active compound combinations comprising (A) at least one host defense inducer and (B) at least one biological control agent in a synergistically effective amount for the use in controlling bacterial harmful organisms in useful plants.

Host Defense Inducers

In the context of the present invention host defense inducers refer to compounds which are characterized by their capability of stimulating the plant's own defense mechanisms so that the plant is protected against infection. Host defense inducers are then used for inducing early and strongly genes known as plant defense inducers. They prime the plant for stronger and/or faster induction of defense genes after a pathogen attack. According to the present invention, host defense inducers comprise e.g.

Acibenzolar-S-methyl:

Isotianil:

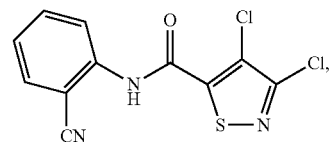 [SMILES: N#Cc1ccccc1NC(=O)c1snc(Cl)c1Cl]

Probenazole:

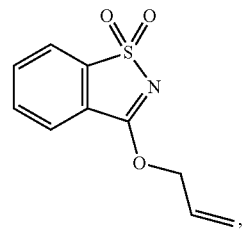

Tiadinil:

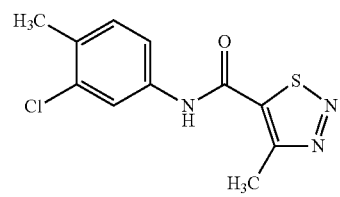 [SMILES: Cc1ccc(NC(=O)c2snnc2C)cc1Cl]

Laminarin:

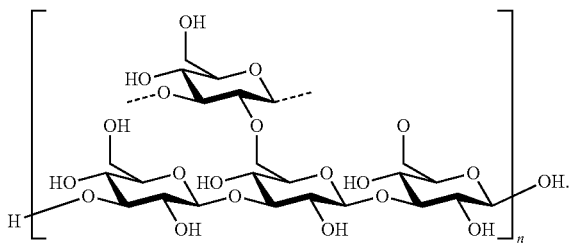

Preferably, the at least one host defense inducer (A) is selected from the group consisting of A.1 acibenzolar-S-methyl, A.2 isotianil, A.3 probenazole and A.4 tiadinil or combinations thereof, more preferably the at least one host defense inducer (A) is A.2 isotianil. In a further preferred embodiment the at least one host defense inducer (A) is a combination of A.2 isotianil and A.1 acibenzolar-S-methyl.

The host defense inducers (A) of the present invention may, if appropriate, be present in the form of mixtures of various isomeric forms which are possible, in particular stereoisomers, such as optical isomers.

Biological Control Agents

As used herein, "biological control" is defined as control of a plant pathogenic organism such as a pathogen and/or insect and/or an acarid and/or a nematode by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

In general "pesticidal" means the ability of a substance to increase mortality or inhibit the growth rate of plant pests. The term is used herein, to describe the property of a substance to exhibit activity against insects, mites, nematodes and/or phytopathogens. In the sense of the present invention the term "pests" include insects, mites, nematodes and/or phytopathogenic bacteria.

"Insecticides" as well as the term "insecticidal" refers to the ability of a substance to increase mortality or inhibit growth rate of insects. As used herein, the term "insects" includes all organisms in the class "Insecta". The term "pre-adult" insects refers to any form of an organism prior to the adult stage, including, for example, eggs, larvae, and nymphs.

"Nematicides" and "nematicidal" refers to the ability of a substance to increase mortality or inhibit the growth rate of nematodes. In general, the term "nematode" comprises eggs, larvae, juvenile and mature forms of said organism.

"Acaricide" and "acaricidal" refers to the ability of a substance to increase mortality or inhibit growth rate of ectoparasites belonging to the class Arachnida, sub-class Acari.

The term "metabolite" refers to any compound, substance or byproduct of a fermentation of a microorganism that has pesticidal activity.

The term "mutant" refers to a variant of the parental strain as well as methods for obtaining a mutant or variant in which the pesticidal activity is greater than that expressed by the parental strain. The "parent strain" is defined herein as the original strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art.

A "variant" is a strain having all the identifying characteristics of the NRRL or ATCC Accession Numbers as indicated in this text and can be identified as having a genome that hybridizes under conditions of high stringency to the genome of the NRRL or ATCC Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated NRRL or ATCC Accession Number may also be defined as a strain having a genomic sequence that is greater than 85%, more preferably greater than 90% or more preferably greater than 95% sequence identity to the genome of the indicated NRRL or ATCC Accession Number. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987) Supplement 30, section 7. 7. 18, Table 7. 7. 1.

NRRL is the abbreviation for the Agricultural Research Service Culture Collection, an international depositary authority for the purposes of deposing microorganism strains under the Budapest treaty on the international recognition of the deposit of microorganisms for the purposes of patent procedure, having the address National Center for Agricultural Utilization Research, Agricultural Research service, U.S. Department of Agriculture, 1815 North university Street, Peroira, Ill. 61604 USA.

ATCC is the abbreviation for the American Type Culture Collection, an international depositary authority for the purposes of deposing microorganism strains under the Budapest treaty on the international recognition of the deposit of microorganisms for the purposes of patent procedure, having the address ATCC Patent Depository, 10801 University Blvd., Manassas, Va. 10110 USA.

Samples of the Bacillus subtilis strain QST713/AQ713 (NRRL Accession No. B-21661), Bacillus subtilis strain QST30002/AQ30002 (NRRL Accession No. B-50421), and Bacillus subtilis strain QST30004/AQ30004 (NRRL Accession No. B-50455) have been deposited with the Agricultural Research Service Culture Collection located at the National Center for Agricultural Utilization Research, Agricultural Research Service, U.S. Department of Agriculture (NRRL), 1815 North University Street, Peoria, Ill. 61604, U.S.A., under the Budapest Treaty on Mar. 7, 1997, Oct. 5, 2010, and Dec. 6, 2010, respectively.

Biological control agents include in particular bacteria, fungi and/or yeasts, protozoa, viruses, entomopathogenic nematodes, Inoculants and botanicals and/or mutants of them having all identifying characteristics of the respective strain, and/or a metabolite produced by the respective strain that exhibits activity against bacterial harmful organisms, insects, mites, nematodes and/or phytopathogens.

According to the present invention the biological control agents (B) are particularly selected from the group consisting of 1) bacteria and 2) fungi (comprising yeasts).

1) Bacteria

According to the invention, biological control agents which are summarized under the term "bacteria" include spore-forming, root-colonizing bacteria, or bacteria and their metabolites useful as biological insecticdes, -nematicdes, miticides, or -fungicide or soil amendments improving plant health and growth. Examples of such bacteria to be used or employed according to the invention are (The numbering is used throughout the complete following description of the invention):
B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); B.1.2 *Bacillus subtilis* strain AQ153 (having NRRL Accession No. 55614 and described in U.S. Pat. No. 5,753,222); B.1.3 *Bacillus* sp. strain AQ175 (having ATCC Accession No. 55608 and described in U.S. Pat. No. 5,869,042); B.1.4 *Bacillus* sp. strain AQ177 (having ATCC Accession No. 55609 and described in U.S. Pat. No. 5,869,042); B.1.5 *Bacillus* sp. strain AQ178 (having ATCC Accession No. 53522 and described in U.S. Pat. No. 5,869,042); B.1.6 *Bacillus amyloliquefaciens*, strain D747 (available as Bacstar® from Etec Crop Solutions, NZ and also available as Double Nickel™ from Certis, US, having Accession No. FERM BP-8234, see abstract of U.S. Pat. No. 7,094,592); B.1.7 *Bacillus pumilus*, in particular strain BU F-33 (available as Integral F-33 from Becker Underwood, US, having Accession No. B-50185); B.1.8 *B. subtilis* var. *amyloliquefaciens* strain FZB24 (available as Taegro® from Novozymes, US, having Accession No. 000-00-9002); B.1.9 *B. thuringiensis* strain AQ52 (Accession No. NRRL B-21619) from AgraQuest, US; B.1.10 *Paenibacillus polymyxa*, in particular strain AC-1 (available as Topseed from Green Biotech Company Ltd., see WO2013010322A1); B.1.11 *Pseudomonas proradix* (available as Proradix® from Sourcon Padena, Accession No. PRORADIX-DSM 13134 (See Claim 1 of U.S. Pat. No. 6,916,650); B.1.12 *Bacillus amyloliquefaciens*, in particular strain IN937a; B.1.13 *Bacillus azotoformans*; B.1.14 *Bacillus smithii*; B.1.15 *Bacillus subtilis*, in particular strain DB 101; B.1.16 *Lysobacter antibioticus*, in particular strain 13-1 (cf. Biological Control 2008, 45, 288-296); B.1.17 *Pantoea agglomerans*, in particular strain E325 (Accession No. NRRL B-21856).

Preferred bacteria are B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); B.1.2 *Bacillus subtilis* strain AQ153 (having NRRL Accession No. 55614 and described in U.S. Pat. No. 5,753,222); B.1.3 *Bacillus* sp. strain AQ175 (having ATCC Accession No. 55608 and described in U.S. Pat. No. 5,869,042); B.1.4 *Bacillus* sp. strain AQ177 (having ATCC Accession No. 55609 and described in U.S. Pat. No. 5,869,042); B.1.5 *Bacillus* sp. strain AQ178 (having ATCC Accession No. 53522 and described in U.S. Pat. No. 5,869,042); B.1.6 *Bacillus amyloliquefaciens*, strain D747 (available as Bacstar® from Etec Crop Solutions, NZ and also available as Double Nickel™ from Certis, US); B.1.7 *Bacillus pumilus*, in particular strain BU F-33 (available as Integral F-33 from Becker Underwood, US); B.1.8 *B. subtilis* var. *amyloliquefaciens* strain FZB24 (available as Taegro® from Novozymes, US); B.1.9 *B. thuringiensis* strain AQ52 (Accession No. NRRL B-21619) from AgraQuest, US; B.1.10 *Paenibacillus polymyxa*, in particular strain AC-1 (available as Topseed from Green Biotech Company Ltd.); B.1.11 *Pseudomonas proradix* (available as Proradix® from Sourcon Padena).

Particularly preferred bacteria are B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); B.1.2 *Bacillus subtilis* strain AQ153 (having NRRL Accession No. 55614 and described in U.S. Pat. No. 5,753,222); B.1.3 *Bacillus* sp. strain AQ175 (having ATCC Accession No. 55608 and described in U.S. Pat. No. 5,869,042); B.1.4 *Bacillus* sp. strain AQ177 (having ATCC Accession No. 55609 and described in U.S. Pat. No. 5,869,042); B.1.5 *Bacillus* sp. strain AQ178 (having ATCC Accession No. 53522 and described in U.S. Pat. No. 5,869,042).

Most preferred bacteria are B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051).

The bacterial strains *Bacillus* sp. AQ175 (ATCC Accession No. 55608), *Bacillus* sp. AQ 177 (ATCC Accession No. 55609) and *Bacillus* sp. AQ178 (ATCC Accession No. 53522) described in WO 98/21697 A1 are known to be effective in treating and protecting plants from aboveground fungal and bacterial infections.

*Bacillus subtilis* AQ713 (Accession No. B-21661), also named *Bacillus subtilis* QST713, exhibits broad fungicidal and bactericidal activity and also exhibits corn rootworm activity (WO 98/50422 A1). Commercially available formulations of this strain are available under the tradenames SERENADE® MAX, SERENADE® Soil, SERENADE® ASO, SERENADE® CPB and RHAPSODY® from Bayer CropScience LP, US (previously AgraQuest, Inc. USA). SERENADE® ASO is a liquid formulation of the *Bacillus subtilis* strain, while SERENADE® Max is a dry formulation. Both products can be used interchangeably against bacterial diseases.

Respective formulas of the trade products are exemplified as follows:

SERENADE® ASO:
Aqueous Suspension/ASO=Aqueous Suspension Organic Active Ingredient:

| | |
|---|---|
| QST 713 strain of *Bacillus subtilis*\* | 1.34% |
| Other ingredients | 98.66% |
| TOTAL | 100.00% |

*Contains a minimum of 1 × 10⁹ cfu/g
U.S. Pat. Nos. 6,060,051; 6,103,228; 6,291,426, and 6,417,163 on QST 713 strain of *Bacillus subtilis*.

SERENADE® MAX:
Wettable powder
Active Ingredient:

| | |
|---|---|
| QST 713 strain of dried *Bacillus subtilis*\* | 14.6% |
| Other ingredients | 85.4% |
| TOTAL | 100.0% |

*Contains a minimum of 7.3 × 10⁹ cfu/g
U.S. Pat. Nos. 6,060,051, 6,103,228, 6,291,426, and 6,417,163 on QST 713 strain of *Bacillus subtilis*.

SERENADE® Soil:
Aqueous Suspension
Active Ingredient:

| QST 713 strain of dried *Bacillus subtilis*\* | 1.34% |
|---|---|
| Other ingredients | 98.66% |
| TOTAL | 100.00% |

*Contains a minimum of 1 x 10⁹ cfu/g
U.S. Pat. Nos. 6,060,051, 6,103,228, 6,291,426, and 6,417,163 on QST 713 strain of *Bacillus subtilis*.

Bactericidal activity of *Bacillus subtilis* is known against Bacterial leaf spot (*Xanthemonas*), Scab (*venturia*), Fire blight (*Erwinia*), *Pseudomonas*, Bacterial wilt (*Ralstonia*), Canker (including citrus canker, caused by *Candidatus Liberibacter* spec.). The Mode of Action comprises broad antifungal activity, elicitation of plant responses—ISR (Induced Systemic Resistance), Colonisation of the leaf and out-competition of pathogens. Tank Mixing is possible with e.g. fungicides such as azoxystrobin, boscalid and pyraclostrobin, chlorothalonil, cyprodinil, iprodione, myclobutanil, potassium bicarbonate, sulphur; insecticides such as abamectin, *Bacillus thuringiensis*, spinosad. Tank mixing with Fosetyl-Al should be avoided, as this can cause precipitation of the spores. Accordingly, in one preferred embodiment tank mixing of a combination of the present invention with fosetyl-Al is excluded.

*Bacillus subtilis* AQ153 (ATCC Accession No. 55614) as described in WO 98/21964 A1 is effective in inhibiting growth of plant pathogenic bacteria and fungi.

According to WO 98/21965 A1 the antibiotic producing strain *Bacillus thuringiensis* AQ52 (NRRL Accession No. B-21619) exhibits broad fungicidal and bactericidal activity.

2) Fungi and/or Yeasts

According to the invention biological control agents that are summarized under the term "fungi" and/or "yeasts" are as examples the following organisms and and/or mutants of them having all identifying characteristics of the respective strain, and/or metabolites produced by the respective strain that exhibit activity against insects, mites, nematodes and/or phytopathogens (the numbering is used in the complete description):
B.2.1 *Pseudozyma aphidis* (see WO2011151819A2); B.2.2 *Aureobasidium pullulans*, in particular blastospores of strain DSM14940; B.2.3 *Aureobasidium pullulans* blastospores of strain DSM 14941; or mixtures thereof; B.2.4 *Saccharomyces cerevisiae*, in particular strain CNCM No. 1-3936; B.2.5 *Saccharomyces cerevisiae*, in particular strain CNCM No. 1-3937; B.2.6 *Saccharomyces cerevisiae*, in particular strain CNCM No. 1-3938; B.2.7 *Saccharomyces cerevisiae*, in particular strain CNCM No. I-3939; B.2.8 *Scleroderma citrinum*.

Preferred fungi are B.2.1 *Pseudozyma aphidis*.

Thus, according to the present invention combinations are preferred, wherein the biological control agent (B) is selected from the group consisting of
1) bacteria consisting of B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); B.1.2 *Bacillus subtilis* strain AQ153 (having NRRL Accession No. 55614 and described in U.S. Pat. No. 5,753,222); B.1.3 *Bacillus* sp. strain AQ175 (having ATCC Accession No. 55608 and described in U.S. Pat. No. 5,869,042); B.1.4 *Bacillus* sp. strain AQ177 (having ATCC Accession No. 55609 and described in U.S. Pat. No. 5,869,042); B.1.5 *Bacillus* sp. strain AQ178 (having ATCC Accession No. 53522 and described in U.S. Pat. No. 5,869,042); B.1.6 *Bacillus amyloliquefaciens*, strain D747 (available as Bacstar® from Etec Crop Solutions, NZ and also available as Double Nickel™ from Certis, US); B.1.7 *Bacillus pumilus*, in particular strain BU F-33 (available as Integral F-33 from Becker Underwood, US); B.1.8 *B. subtilis* var. *amyloliquefaciens* strain FZB24 (available as Taegro® from Novozymes, US); B.1.9 *B. thuringiensis* strain AQ52 (Accession No. NRRL B-21619) from AgraQuest, US; B.1.10 *Paenibacillus polymyxa*, in particular strain AC-1 (available as Topseed from Green Biotech Company Ltd.); B.1.11 *Pseudomonas proradix* (available as Proradix® from Sourcon Padena); and
2) fungi consisting of B.2.1 *Pseudozyma aphidis*.

Even more preferred are combinations, wherein the biological control agent (B) is selected from the group consisting of
1) bacteria consisting of B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); B.1.2 *Bacillus subtilis* strain AQ153 (having NRRL Accession No. 55614 and described in U.S. Pat. No. 5,753,222); B.1.3 *Bacillus* sp. strain AQ175 (having ATCC Accession No. 55608 and described in U.S. Pat. No. 5,869,042); B.1.4 *Bacillus* sp. strain AQ177 (having ATCC Accession No. 55609 and described in U.S. Pat. No. 5,869,042); B.1.5 *Bacillus* sp. strain AQ178 (having ATCC Accession No. 53522 and described in U.S. Pat. No. 5,869,042); and
2) fungi consisting of B.2.1 *Pseudozyma aphidis*.

Most preferred are combinations, wherein the biological control agent (B) is selected from the group consisting of
1) bacteria consisting of B.1.1 *Bacillus subtilis*, in particular strain QST713/AQ713 (available as SERENADE MAX from Bayer CropScience LP, US, having NRRL Accession No. B21661 and described in U.S. Pat. No. 6,060,051); and
2) fungi consisting of B.2.1 *Pseudozyma aphidis*.

Further biological control agents include in particular protozoa, viruses, entomopathogenic nematodes and botanicals and/or mutants of them.

3) Protozoas

According to the invention biological control agents that are summarized under the term "protozoas" are the following examples (the numbering is used in the complete description):
B.3.1 *Nosema locustae* (products known as NoloBait), B.3.2 *Thelohania solenopsis* and B.3.3 *Vairimorpha* spp.

4) Viruses

According to the invention biological control agents that are summarized under the term "viruses" are the following examples. They include mutants of them having all identifying characteristics of the respective strain, and/or metabolites produced by the respective strain that exhibit activity against insects, mites, nematodes and/or phytopathogens (the numbering is used in the complete description):
B.4.1 *Adoxophyes orana* (summer fruit tortrix) granulosis virus (GV), (product known as BIOFA-Capex®), B.4.2 *Agrotis segetum* (turnip moth) nuclear polyhedrosis virus (NPV), B.4.3 *Anticarsia gemmatalis* (Woolly pyrol moth) mNPV (products known as Polygen), B.4.4 *Autographa californica* (Alfalfa Looper) mNPV (products known as VPN80 from *Agricola El Sol*), B.4.5 Biston suppressaria (tea looper) NPV, B.4.6 *Bombyx mori* (silkworm) NPV, B.4.7 *Cryptophlebia leucotreta* (false codling moth) GV (products known as Cryptex), B.4.8 *Cydia pomonella* (Codling moth) granulosis virus (GV) (product known as Madex Plus), B.4.9 *Dendrolimus punctatus* (Masson pine moth) CPV, B.4.10 *Helicoverpa armigera* NPV (product known as AgBiTech—ViVUS Max), B.4.11 *Helicoverpa* (previously *Heliothis*) *zea* (corn earworm) NPV (products known as Elcar), B.4.12 *Leucoma salicis* (satin moth) NPV, B.4.13 *Lymantria dispar* (gypsy moth) NPV (products known as Gypcheck), B.4.14 *Neodiprion abietis* (balsam-fir sawfly) NPV (products known as Abietiv), B.4.15 *Neodiprion lecontei* (red-headed pinesawfly) NPV (products known as Lecontvirus), B.4.16 *Neodiprion sertifer* (Pine sawfly) NPV (products known as Neocheck-S), B.4.17 *Orgyia pseudotsugata* (Douglas-fir tussock moth) NPV (products known as Virtuss), B.4.18 *Phthorimaea operculella* (tobacco leaf miner) GV (products known as Matapol), B.4.19 *Pieris rapae* (small white) GV, B.4.20 *Plutella xylostella* (diamondback moth) GV (products known as Plutec), B.4.21 *Spodoptera albula* (gray-streaked armywom moth) mNPV (products known as VPN 82), B.4.22 *Spodoptera exempta* (true armyworm) mNPV (products known as Spodec), B.4.23 *Spodoptera exigua* (sugarbeet armyworm) mNPV (products known as Spexit from Andermatt Biocontrol), B.4.24 *Spodoptera frugiperda* (fall armyworm) mNPV (products known as Baculovirus VPN), B.4.25 *Spodoptera littoralis* (tobacco cutworm) NPV (procucts known as Spodoptrin from NPP Calliope France), and B.4.26 *Spodoptera litura* (oriental leafworm moth) NPV (products known as Littovir).

5) Entomopathogenic Nematodes

According to the invention biological control agents that are summarized under the term "entomopathogenic nematodes" are (the numbering is used in the complete description):

B.5.1 *Abbreviata caucasica*, B.5.2 *Acuaria* spp., B.5.3 *Agamermis decaudata*, B.5.4 *Allantonema* spp., B.5.5 *Amphimermis* spp., B.5.6 *Beddingia* (=*Deladenus*) *siridicola*, B.5.7 *Bovienema* spp., B.5.7a *Cameronia* spp., B.5.8 *Chitwoodiella ovofilamenta*, B.5.9 *Contortylenchus* spp., B.5.10 *Culicimermis* spp., B.5.11 *Diplotriaena* spp., B.5.12 *Empidomermis* spp., B.5.13 *Filipjevimermis leipsandra*, B.5.14 *Gastromermis* spp., B.5.15 *Gongylonema* spp., B.5.16 *Gynopoecilia pseudovipara*, B.5.17 *Heterorhabditis* spp., in particular *Heterorhabditis bacteriophora* (products known as B-Green), or *Heterorhabditis baujardi*, or *Heterorhabditis heliothidis* (products known as Nematon), or *Heterorhabditis indica*, *Heterorhabditis marelatus*, *Heterorhabditis megidis*, *Heterorhabditis zealandica*, B.5.18 *Hexamermis* spp., B.5.19 *Hydromermis* spp., B.5.20 *Isomermis* spp., B.5.21 *Limnomermis* spp., B.5.22 *Maupasina weissi*, B.5.23 *Mermis nigrescens*, B.5.24 *Mesomermis* spp., B.5.25 *Neomesomermis* spp., B.5.26 *Neoparasitylenchus rugulosi*, B.5.27 *Octomyomermis* spp., B.5.28 *Parasitaphelenchus* spp., B.5.29 *Parasitorhabditis* spp., B.5.30 *Parasitylenchus* spp., B.5.31 *Perutilimermis culicis*, B.5.32 *Phasmarhabditis hermaphrodita*, B.5.33 *Physaloptera* spp., B.5.34 *Protrellatus* spp., B.5.35 *Pterygodermatites* spp., B.5.36 *Romanomermis* spp., B.5.37 *Seuratum cadarachense*, B.5.38 *Sphaerulariopsis* spp., B.5.39 *Spirura guianensis*, B.5.40 *Steinernema* spp. (=*Neoaplectana* spp.), in particular *Steinernema carpocapsae* (products known as Biocontrol), or *Steinernema feltiae* (=*Neoaplectana carpocapsae*), (products known as Nemasys®), or *Steinernema glaseri* (products known as Biotopia), or *Steinernema kraussei* (products known as Larvesure), or *Steinernema riobrave* (products known as Biovector), or *Steinernema scapterisci* (products known as Nematac S), or *Steinernema scarabaei*, or *Steinernema siamkayai*, B.5.41 *Strelkovimermis peterseni*, B.5.42 *Subulura* spp., B.5.43 *Sulphuretylenchus elongatus*, and B.5.44 *Tetrameres* spp.

Within the meaning of the present invention the at least one biological control agent (B) comprises not only the isolated, pure cultures of the respective microorganisms, but also their suspensions in a whole broth culture or a metabolite-containing supernatant or a purified metabolite obtained from whole broth culture of the strain. "Whole broth culture" refers to a liquid culture containing both cells and media. "Supernatant" refers to the liquid broth remaining when cells grown in broth are removed by centrifugation, filtration, sedimentation, or other means well known in the art.

The above-mentioned metabolites produced by the non-pathogenic microorganisms include antibiotics, enzymes, siderophores and growth promoting agents, for example zwittermicin-A, kanosamine, polyoxine, enzymes such as α-amylase, chitinases, and pektinases, phytohormones and precursors thereof, such as auxines, gibberlin-like substacnes, cytokinin-like compounds, lipopeptides such as iturins, plipastatins or surfactins, e.g. agrastatin A, bacillomycin D, bacilysin, difficidin, macrolactin, fengycin, bacilysin and bacilaene. Preferred metabolites of the above listed lipopeptides are in particular produced by *Bacillus pumilus* (NRRL Accession No. B-30087), *Bacillus subtilis* AQ713 (NRRL Accession No. B-21661), *Bacillus subtilis* strain AQ30002 (aka QST30002; NRRL Accession No. B-50421), or *Bacillus subtilis* strain AQ30004 (aka QST30004; NRRL Accession No. B-50455,).

According to the invention, the biological control agent may be employed or used in any physiologic state such as active or dormant.

The combinations according to the present invention are particularly suitable in the use for controlling bacterial harmful organisms. According to the present invention bacterial harmful organisms include inter alia bacteria causing damage to plants or to a part of a plant.

Bacteria include inter alia *Actinobacteria* and *Proteobacteria* and are selected from the families of the Burkholderiaceae, Xanthomonadaceae, Pseudomonadaceae, Enterobacteriaceae, Microbacteriaceae, and Rhizobiaceae.

According to the present invention the bacterial harmful organisms are particularly selected from the group consisting of:

*Acidovorax avenae* (=*Pseudomonas avenae, Pseudomonas avenae* subsp. *avenae, Pseudomonas rubrilineans*), including e.g. *Acidovorax avenae* subsp. *avenae* (=*Pseudomonas avenae* subsp. *avenae*), *Acidovorax avenae* subsp. *cattleyae* (=*Pseudomonas cattleyae*), *Acidovorax avenae* subsp. *citrulli* (=*Pseudomonas pseudoalcaligenes* subsp. *citrulli, Pseudomonas avenae* subsp. *citrulli*)); *Burkholderia* spec., including e.g. *Burkholderia andropogonis* (=*Pseudomonas andropogonis, Pseudomonas woodsii*), *Burkholderia caryophylli* (=*Pseudomonas caryophylli*), *Burkholderia cepacia* (=*Pseudomonas cepacia*), *Burkholderia gladioli* (=*Pseudomonas gladioli*), *Burkholderia gladioli* pv. *agaricicola* (=*Pseudomnas gladioli* pv. *agaricicola*), *Burkholderia gladioli* pv. *alliicola* (=*Pseusomonas gladioli* pv. *alliicola*), *Burkholderia gladioli* pv. *gladioli* (=*Pseudomonas gladioli, Pseudomonas gladioli* pv. *gladioli*), *Burkholderia glumae* (=*Pseudomonas glumae*), *Burkholderia plantarii* (=*Pseudomonas plantarii*) *Burkholderia solanacearum* (=*Ralstonia solanacearum*), and *Ralstonia* spp.;

*Liberibacter* spp., including *Candidatus Liberibacter* spec., including e.g. *Liberibacter africanus* (Laf), *Liberibacter americanus* (Lam), *Liberibacter asiaticus* (Las), *Liberibacter europaeus* (Leu), *Liberibacter solanacearum* (Lso); *Corynebacterium*, including e.g. *Corynebacterium fascians, Corynebacterium flaccumfaciens* pv. *flaccumfaciens, Corynebacterium michiganensis, Corynebacterium michiganense* pv. *tritici, Corynebacterium michiganense* pv. *nebraskense, Corynebacterium sepedonicum*;

*Erwinia spec.* including e.g. *Erwinia amylovora, Erwinia ananas, Erwinia carotovora* (=*Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia dissolvens, Erwinia herbicola, Erwinia rhapontic, Erwinia stewartiii, Erwinia tracheiphila, Erwinia uredovora; Pseudomonas syringae*, including e.g. *Pseudomonas syringae* pv. *actinidiae* (Psa), *Pseudomonas syringae* pv. *atrofaciens, Pseudomonas syringae* pv. *coronafaciens, Pseudomonas syringae* pv. *glycinea, Pseudomonas syringae* pv. *lachrymans, Pseudomonas syringae* pv. *maculicola Pseudomonas syringae* pv. *papulans, Pseudomonas syringae* pv. *striafaciens, Pseudomonas syringae* pv. *syringae, Pseudomonas syringae* pv. *tomato, Pseudomonas syringae* pv. *tabaci*;

*Streptomyces* ssp., including e.g. *Streptomyces acidiscabies, Streptomyces albidoflavus, Streptomyces candidus* (=*Actinomyces candidus*), *Streptomyces caviscabies, Streptomyces collinus, Streptomyces europaeiscabiei, Streptomyces intermedius, Streptomyces ipomoeae, Streptomyces luridiscabiei, Streptomyces niveiscabiei, Streptomyces puniciscabiei, Streptomyces retuculiscabiei, Streptomyces scabiei, Streptomyces scabies, Streptomyces setonii, Streptomyces steliiscabiei, Streptomyces turgidiscabies, Streptomyces wedmorensis*;

*Xanthomonas axonopodis*, including e.g. *Xanthomonas axonopodis* pv. *alfalfae* (=*Xanthomonas alfalfae*), *Xanthomonas axonopodis* pv. *aurantifolii* (=*Xanthomonas fuscans* subsp. *aurantifolii*), *Xanthomonas axonopodis* pv. *allii* (=*Xanthomonas campestris* pv. *allii*), *Xanthomonas axonopodis* pv. *axonopodis, Xanthomonas axonopodis* pv. *bauhiniae* (=*Xanthomonas campestris* pv. *bauhiniae*), *Xanthomonas axonopodis* pv. *begoniae* (=*Xanthomonas campestris* pv. *begoniae*), *Xanthomonas axonopodis* pv. *betlicola* (=*Xanthomonas campestris* pv. *betlicola*), *Xanthomonas axonopodis* pv. *biophyti* (=*Xanthomonas campestris* pv. *biophyti*), *Xanthomonas axonopodis* pv. *cajani* (=*Xanthomonas campestris* pv. *cajani*), *Xanthomonas axonopodis* pv. *cassavae* (=*Xanthomonas cassavae, Xanthomonas campestris* pv. *cassavae*), *Xanthomonas axonopodis* pv. *cassiae* (=*Xanthomonas campestris* pv. *cassiae*), *Xanthomonas axonopodis* pv. *citri* (=*Xanthomonas citri*), *Xanthomonas axonopodis* pv. *citrumelo* (=*Xanthomonas alfalfae* subsp. *citrumelonis*), *Xanthomonas axonopodis* pv. *clitoriae* (=*Xanthomonas campestris* pv. *clitoriae*), *Xanthomonas axonopodis* pv. *coracanae* (=*Xanthomonas campestris* pv. *coracanae*), *Xanthomonas axonopodis* pv. *cyamopsidis* (=*Xanthomonas campestris* pv. *cyamopsidis*), *Xanthomonas axonopodis* pv. *desmodii* (=*Xanthomonas campestris* pv. *desmodii*), *Xanthomonas axonopodis* pv. *desmodiigangetici* (=*Xanthomonas campestris* pv. *desmodiigangetici*), *Xanthomonas axonopodis* pv. *desmodiilaxiflori* (=*Xanthomonas campestris* pv. *desmodiilaxiflori*), *Xanthomonas axonopodis* pv. *desmodiirotundifolii* (=*Xanthomonas campestris* pv. *desmodiirotundifolii*), *Xanthomonas axonopodis* pv. *dieffenbachiae* (=*Xanthomonas campestris* pv. *dieffenbachiae*), *Xanthomonas axonopodis* pv. *erythrinae* (=*Xanthomonas campestris* pv. *erythrinae*), *Xanthomonas axonopodis* pv. *fascicularis* (=*Xanthomonas campestris* pv. *fasciculari*), *Xanthomonas axonopodis* pv. *glycines* (=*Xanthomonas campestris* pv. *glycines*), *Xanthomonas axonopodis* pv. *khayae* (=*Xanthomonas campestris* pv. *khayae*), *Xanthomonas axonopodis* pv. *lespedezae* (=*Xanthomonas campestris* pv. *lespedezae*), *Xanthomonas axonopodis* pv. *maculifoliigardeniae* (=*Xanthomonas campestris* pv. *maculifoliigardeniae*), *Xanthomonas axonopodis* pv. *malvacearum* (=*Xanthomonas citri* subsp. *malvacearum*), *Xanthomonas axonopodis* pv. *manihotis* (=*Xanthomonas campestris* pv. *manihotis*), *Xanthomonas axonopodis* pv. *martyniicola* (=*Xanthomonas campestris* pv. *martyniicola*), *Xanthomonas axonopodis* pv. *melhusii* (=*Xanthomonas campestris* pv. *melhusii*), *Xanthomonas axonopodis* pv. *nakataecorchori* (=*Xanthomonas campestris* pv. *nakataecorchori*), *Xanthomonas axonopodis* pv. *passiflorae* (=*Xanthomonas campestris* pv. *passiflorae*), *Xanthomonas axonopodis* pv. *patelii* (=*Xanthomonas campestris* pv. *patelii*), *Xanthomonas axonopodis* pv. *pedalii* (=*Xanthomonas campestris* pv. *pedalii*), *Xanthomonas axonopodis* pv. *phaseoli* (=*Xanthomonas campestris* pv. *phaseoli, Xanthomonas phaseoli*), *Xanthomonas axonopodis* pv. *phaseoli* var. *fuscans* (=*Xanthomonas fuscans*), *Xanthomonas axonopodis* pv. *phyllanthi* (=*Xanthomonas campestris* pv. *phyllanthi*), *Xanthomonas axonopodis* pv. *physalidicola* (=*Xanthomonas campestris* pv. *physalidicola*), *Xanthomonas axonopodis* pv. *poinsettiicola* (=*Xanthomonas campestris* pv. *poinsettiicola*), *Xanthomonas axonopodis* pv. *punicae* (=*Xanthomonas campestris* pv. *punicae*), *Xanthomonas axonopodis* pv. *rhynchosiae* (=*Xanthomonas campestris* pv. *rhynchosiae*), *Xanthomonas axonopodis* pv. *ricini* (=*Xanthomonas campestris* pv. *ricini*), *Xanthomonas axonopodis* pv. *sesbaniae* (=*Xanthomonas campestris* pv. *sesbaniae*), *Xanthomonas axonopodis* pv. *tamarindi* (=*Xanthomonas campestris* pv. *tamarindi*), *Xanthomonas axonopodis* pv. *vasculorum* (=*Xanthomonas campestris* pv. *vasculorum*), *Xanthomonas axonopodis* pv. *vesicatoria* (=*Xanthomonas campestris* pv. *vesicatoria, Xanthomonas vesicatoria*), *Xanthomonas axonopodis* pv. *vignaeradiatae* (=*Xanthomonas campestris* pv. *vignaeradiatae*), *Xanthomonas axonopodis* pv. *vignicola* (=*Xanthomonas campestris* pv. *vignicola*), *Xanthomonas axonopodis* pv. *vitians* (=*Xanthomonas campestris* pv. *vitians*); *Xanthomonas campestris* pv. *musacearum, Xanthomonas campestris* pv. *pruni* (=*Xanthomonas arboricola* pv. *pruni*), *Xanthomonasfragariae; Xanthomonas translucens* (=*Xanthomonas campestris* pv. *hordei*) including e.g. *Xanthomonas translucens* pv. *arrhenatheri* (=*Xanthomonas campestris* pv. *arrhenatheri*), *Xanthomonas translucens* pv. *cerealis* (=*Xanthomonas campestris* pv. *cerealis*), *Xanthomonas translucens* pv. *graminis* (=*Xanthomonas campestris* pv. *graminis*), *Xanthomonas translucens* pv. *phlei* (=*Xanthomonas campestris* pv. *phlei*), *Xanthomonas translucens* pv. *phleipratensis* (=*Xanthomonas campestris* pv. *phleipratensis*), *Xanthomonas translucens* pv. *poae* (=*Xanthomonas campestris* pv. *poae*), *Xanthomonas translucens* pv. *secalis* (=*Xanthomonas campestris* pv. *secalis*), *Xanthomonas translucens* pv. *translucens* (=*Xanthomonas campestris* pv. *translucens*), *Xanthomonas translucens* pv. *undulosa* (=*Xanthomonas campestris* pv. *undulosa*).

*Xanthomonas oryzae, Xanthomonas oryzae* pv. *oryzae* (=*Xanthomonas campestris* pv. *oryzae*), *Xanthomonas oryzae* pv. *oryzicola* (=*Xanthomonas campestris* pv. *oryzicola*).

*Xylella fastidiosa* from the family of *Xanthomona daceae*.

Preferably, the bacterial harmful organisms are selected from the group consisting of:

*Acidovorax avenae* subsp. *avenae* (=*Pseudomonas avenae* subsp. *avenae*), *Acidovorax avenae* subsp. *citrulli* (=*Pseudomonas pseudoalcaligenes* subsp. *citrulli, Pseudomonas avenae* subsp. *citrulli*), *Burkholderia glumae* (=*Pseudomonas glumae*), *Burkholderia solanacearum* (=*Ralstonia solanacearum*), *Corynebacterium michiganense* pv. *nebraskense, Erwinia amylovora, Erwinia carotovora* (=*Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia herbicola, Erwinia stewartiii, Erwinia uredovora, Liberibacter* spp., *Candidatus Liberibacter* spec. as defined above, *Pseudomonas syringae, Pseudomonas syringae* pv. *actinidiae* (Psa), *Pseudomonas syringae* pv. *glycinea, Pseudomonas syringae* pv. *lachrymans, Pseudomonas syringae* pv. *papulans, Pseudomonas syringae* pv. *syringae, Pseudomonas syringae* pv. tomato, *Pseudomonas syringae* pv. *tabaci, Ralstonia* spp., *Streptomyces* scabies, *Xanthomonas axonopodis* pv. *citri, Xanthomonas axonopodis* pv. *glycines* (=*Xanthomonas campestris* pv. *glycines*), *Xanthomonas axonopodis* pv. *punicae* (=*Xanthomonas campestris* pv. *punicae*), *Xanthomonas axonopodis* pv. *vesicatoria* (=*Xanthomonas campestris* pv. *vesicatoria, Xanthomonas vesicatoria*), *Xanthomonas campestris, Xanthomonas campestris* pv. *musacearum, Xanthomonas campestris* pv. *pruni* (=*Xanthomonas arboricola* pv. *pruni*), *Xanthomonas fragariae, Xanthomonas translucens* pv. *translucens* (=*Xanthomonas campestris* pv. *translucens*), *Xanthomonas oryzae* pv. *oryzae* (=*Xanthomonas campestris* pv. *oryzae*), *Xylella fastidiosa.*

In a more preferred aspect of the present invention the bacterial harmful organisms are selected from the group consisting of:

*Acidovorax avenae* (=*Pseudomonas avenae, Pseudomonas avenae* subsp. *avenae, Pseudomonas rubrilineans*) as defined above, *Burkholderia* spec. as defined above, *Burkholderia glumae, Corynebacterium* as defined above, *Erwinia* spec. as defined above, *Erwinia amylovora, Erwinia carotovora* (=*Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia herbicola, Erwinia stewartiii, Erwinia uredovora, Liberibacter* spp., *Candidatus Liberibacter* spec. as defined above, *Pseudomonas syringae* as defined above, *Pseudomonas syringae* pv. *actinidae, Pseudomonas syringae* pv. *glycinea, Pseudomonas syringae* pv. tomato, *Pseudomonas syringae* pv. *lachrymans, Ralstonia* spp., *Streptomyces* spp., *Streptomyces scabies, Xanthomonas* spp., *Xanthomonas axonopodis* as defined above, *Xanthomonas axonopodis* pv. *citri, Xanthomonas axonopodis* pv. *glycines, Xanthomonas campestris, Xanthomonas campestris* pv. *musacearum, Xanthomonas campestris* pv. *pruni* (=*Xanthomonas arboricola* pv. *pruni*), *Xanthomonasfragariae, Xanthomonas translucens* (=*Xanthomonas campestris* pv. *hordei*), *Xanthomonas oryzae* pv. *oryzae* (=*Xanthomonas campestris* pv. *oryzae*) and *Xylella fastidiosa* as defined above.

Even more preferred is a selection consisting of:

*Acidovorax avenae, Burkholderia* spec., *Burkholderia glumae, Corynebacterium, Erwinia* spec., *Liberibacter* spp., *Candidatus Liberibacter* spec., *Pseudomonas syringae, Pseudomonas syringae* pv. *actinidae, Pseudomonas syringae* pv. *glycinea, Pseudomonas syringae* pv. tomato, *Pseudomonas syringae* pv. *lachrymans, Ralstonia* spp., *Streptomyces* spp., *Xanthomonas* spp., *Xanthomonas axonopodis, Xanthomonas axonopodis* pv. *citri, Xanthomonas axonopodis* pv. *glycines, Xanthomonas campestris, Xanthomonas campestris* pv. *musacearum, Xanthomonas campestris* pv. *pruni, Xanthomonas fragariae, Xanthomonas transluscens, Xanthomonas oryzae* pv. *oryzae* (=*Xanthomonas campestris* pv. *oryzae*) and *Xylella fastidiosa.*

In an even more preferred aspect of the present invention the bacterial harmful organisms are selected from the group consisting of:

*Acidovorax avenae, Burkholderia* spec., *Burkholderia glumae, Corynebacterium, Erwinia amylovora, Erwinia carotovora, Erwinia carotovora* subsp. *atroseptica, Erwinia carotovora* subsp. *carotovora, Erwinia chrysanthemi, Erwinia chrysanthemi* pv. *zeae, Erwinia herbicola, Erwinia stewartiii, Erwinia uredovora, Liberibacter* spp., *Candidatus Liberibacter* spec., *Pseudomonas syringae, Pseudomonas syringae* pv. *actinidae, Pseudomonas syringae* pv. *glycinea, Pseudomonas syringae* pv. *lachrymans, Pseudomonas syringae* pv. tomato, *Ralstonia* spp., *Streptomyces scabies, Xanthomonas axonopodis, Xanthomonas axonopodis* pv. *citri, Xanthomonas axonopodis* pv. *glycines, Xanthomonas campestris, Xanthomonas campestris* pv. *musacearum, Xanthomonas campestris* pv. *pruni, Xanthomonas fragariae, Xanthomonas translucens, Xanthomonas oryzae* pv. *oryzae* (=*Xanthomonas campestris* pv. *oryzae*) and *Xylella fastidiosa.*

The most preferred selection comprises the group consisting of:

*Burkholderia glumae, Liberibacter* spp., *Candidatus Liberibacter* spec., *Xanthomonas axonopodis* pv. *citri, Pseudomonas syringae, Pseudomonas syringae* pv. *actinidae, Pseudomonas syringae* pv. *glycinea, Pseudomonas syringae* pv. *lachrymans, Pseudomonas syringae* pv. tomato, *Ralstonia* spp., *Streptomyces scabies, Xanthomonas axonopodis* pv. *glycines, Xanthomonas campestris* pv. *pruni, Xanthomonas campestris, Xanthomonas oryzae* pv. *oryzae* (=*Xanthomonas campestris* pv. *oryzae*) and *Xylella fastidiosa.*

The combination according to the present invention can therefore be employed for protecting plants against attack by the abovementioned pathogens within a certain post-treatment period. The period within which protection is afforded generally extends from 1 to 10 days, preferably 1 to 7 days, after the treatment of the plants with the active compounds. Depending on the form of application, the accessibility of the active compounds to the plant can be controlled in a targeted manner.

The good plant tolerance of the combinations at the concentrations of the host defense inducer and the biological control agent required for controlling plant diseases permits a treatment of aerial and subterranean plant parts, of vegetative propagation material, and of the soil.

The combinations according to the present invention are also suitable for increasing the yield, show low toxicity and are well tolerated by plants. The combinations are particularly suitable for reducing overall damage of plants and plant parts as well as losses in harvested fruits or vegetables caused by phytopathogenic bacteria In the context of the present invention, on application to plants an advantageous effect was observed.

In accordance with the invention, all plants may be treated. Plants are, in the present context, understood as meaning all plant parts and plant populations, such as desired and undesired wild plants or crop plants (including naturally occurring crop plants). Crop plants may be plants which can be obtained by traditional breeding and optimization methods or else by biotechnological and recombinant methods, or combinations of these methods, including the transgenic plants and including the plant varieties capable or not of being protected by Plant Breeders' Rights. Such methods are, for example, doubled haploids, protoplast fusion, random or targeted mutagenesis and also molecular or genetic markers.

Plant parts are intended to mean all aerial and subterranean parts and organs of the plants, such as herb, pseudostem, shoot, leaf, bract, leaf sheaths, petiole, lamina, flower and root, examples which may be mentioned being leaves, needles, stalks, stems, flowers, fruiting bodies, fruit, banana hand, bunches and seeds, and also roots, tubers, rhizomes, offshoots, suckers, secondary growth. The plant parts also include crop material and vegetative and generative propagation material, for example cuttings, tubers, rhizomes, slips and seeds.

As has already been mentioned above, all plants can be treated in accordance with the invention. In a preferred embodiment, plant species and plant varieties, and their parts, which are found in the wild or which are obtained by conventional biological breeding methods, such as hybridization, meristem cultures, micropropagation, somatic embryogenesis, direct organogenesis or protoplast fusion, are treated. In a further preferred embodiment, transgenic plants and plant varieties which have been obtained by recombinant methods, if appropriate in combination with traditional methods (genetically modified organisms), are treated, such as, for example, transformation by means of *Agrobacterium* or particle bombardment of embryogenic cells, and micropropagation. Plants include all plant parts as mentioned above.

It is especially preferred to treat, in accordance with the invention, plants of those plant varieties which are in each case commercially available or in use. Plant varieties are understood as meaning plants with new properties ("traits") which have been obtained by conventional breeding, by mutagenesis or else by recombinant DNA techniques. They may be varieties, breeds, biotypes and genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference [RNAi] technology). A heterologous gene that is located in the genome is also called a transgene. A transgene that is defined by its particular location in the plant genome is called a transformation or transgenic event.

Plants and plant varieties which are preferably to be treated according to the invention include all plants which have genetic material which imparts particularly advantageous, useful traits to these plants (whether obtained by breeding and/or biotechnological means).

Plants that may be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants which can be treated in accordance with the invention and which may be mentioned are the following: cotton, flax, grapevine, vegetables and fruits (for example kiwi, pineapple), such as Rosaceae sp. (for example pome fruits such as apples and pears, but also stone fruits such as apricots, cherries, almonds and peaches, and soft fruits such as strawberries), or pomegranate from the genus of Punica, Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana plants and banana plantations as well as plantains), Rubiaceae sp. (for example coffee), Theaceae sp., Sterculiceae sp., Rutaceae sp. (for example citrus, lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumbers, melons, cucurbits, pumpkins), Alliaceae sp. (for example leeks, onions), Papilionaceae sp. (for example peas); major crop plants such as Gramineae sp. (for example corn, maize, turf, cereals such as wheat, rye, rice, barley, oats, sorghum, millet and triticale), Asteraceae sp. (for example sunflower), Brassicaceae sp. (for example cabbage such as white cabbage and red cabbage, broccoli, cauliflower, Brussels sprouts, pak choi, kohlrabi, small radishes, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, Swiss chard, beetroot); useful plants and ornamental plants in gardens and forests; and in each case genetically modified types of these plants.

Preferably, the combinations of the present invention are used for the treatment in plants selected from the group consisting of:

vegetables and fruits (for example kiwi, melon, pineapple), such as Rosaceae sp. (for example pome fruits such as apples and pears, but also stone fruits such as apricots, cherries, almonds and peaches, and soft fruits such as strawberries), or pomegranate from the genus of Punica, Musaceae sp. (for example banana plants and banana plantations as well as plantains), Rutaceae sp. (for example citrus, lemons, oranges and grapefruit); vegetables, such as Solanaceae sp. (for example tomatoes), Cucurbitaceae sp. (for example cucumbers, melons, cucurbits, pumpkins), major crop plants such as Gramineae sp. (for example corn, maize, turf, cereals such as wheat, rye, rice, barley, oats, sorghum, millet and triticale), Brassicaceae sp. (for example cabbage such as white cabbage and red cabbage, broccoli, cauliflower, Brussels sprouts, pak choi, kohlrabi, small radishes, and also oilseed rape, mustard, horseradish and cress), Papilionaceae sp. (for example soya beans), Solanaceae sp. (for example potatoes); and in each case genetically modified types of these plants.

Even more preferred is the treatment of plants selected from the group consisting of: fruits, vegetables, potatoes, cereals, corn, rice and soybeans.

Therefrom a further preferred selection relates to the group consisting of:
kiwi, melon, pineapple, pome fruits such as apples, pears and pomegranate, stone fruits such as peaches, soft fruits such as strawberries, banana plants and banana plantations as well as plantains, citrus, lemons, oranges and grapefruit; tomatoes, cucumbers, melons, cucurbits, corn, cereals such as wheat, rice, cabbage, cauliflower, soya beans, potatoes; and in each case genetically modified types of these plants.

The most preferred selection of useful plants to be treated in accordance with the present invention relates to: apples, bananas, citrus, kiwi, melons, peaches, pears, pineapple, pome fruit, pomegranate, cabbage, cauliflower, cucumbers, cucurbits, tomatoes, potatoes, wheat, rice and soybeans.

And further to: citrus, kiwi, peaches, cucumbers, tomatoes, potatoes, wheat, rice and soybeans.

A further preferred aspect of the present invention relates to the use of the combinations comprising at least one host defense inducer and at least one biological control agent for controlling at least one of:
*Acidovorax avenae, Burkholderia glumae* and/or *Xanthomonas campestris* pv. *oryzae* in rice; *Candidatus Liberibacter* spec. and/or *Xanthomonas axonopodis* pv. *citri* in citrus; *Corynebacterium* in corn; *Pseudomonas syringae* pv. *actinidae* in Kiwi; *Xanthomonas campestris* in peaches, bananas and/or plantains; *Xanthomonas axonopodis* in pomegranate; *Pseudomonas syringae* pv. *glycinea* and/or *Xanthomonas axonopodis* in soybeans; *Burkholderia* spec. and/or *Xanthomonas transluscens* in cereals (preferably in wheat); *Pseudomonas syringae, Pseudomonas syringae* pv. tomato and/or *Xanthomonas campestris* in tomatoes; *Pseudomonas syringae* and/or *Pseudomonas syringae* pv. *lachrymans* in cucumbers; *Erwinia carotovora, Erwinia carotovora* subsp. *atroseptica* and/or *Streptomyces scabies* in potatoes; *Erwinia carotovora* in bananas and/or plantains; and *Xylella fastidiosa* in citrus.

Therein it is more preferred to use the combinations comprising at least one host defense inducer and at least one biological control agent for controlling at least one of:
*Acidovorax avenae, Burkholderia* spec. (preferably *Burkholderia glumae*) and/or *Xanthomonas campestris* pv. *oryzae* in rice; *Candidatus Liberibacter* spec. and/or *Xanthomonas axonopodis* (preferably *Xanthomonas axonopodis* pv. *citri*) and/or *Xylella fastidiosa* in citrus; *Pseudomonas syringae* (preferably *Pseudomonas syringae* pv. *actinidae*) in Kiwi; *Xanthomonas campestris* and/or *Xanthomonas campestris* pv. *pruni* in peaches; *Pseudomonas syringae* (preferably *Pseudomonas syringae* pv. *glycinea*) and/or *Xanthomonas axonopodis* (preferably *Xanthomonas axonopodis* pv. *glycines* (=*Xanthomonas campestris* pv. *glycines*) in soybeans; *Burkholderia* spec. and/or *Xanthomonas transluscens* in cereals; *Pseudomonas syringae* (preferably *Pseudomonas syringae* pv. tomato) and/or *Xanthomonas campestris* in tomatoes; *Pseudomonas syringae* and/or *Pseudomonas syringae* pv. *lachrymans* in cucumbers; as well as *Erwinia atroseptica, Erwinia carotovora* and/or *Streptomyces scabies* in potatoes.

Most preferred is to use the combinations comprising at least one host defense inducer and at least one biological control agent for controlling *Burkholderia glumae* and/or *Xanthomonas campestris* pv. *oryzae* in rice, *Liberibacter* spec. and/or *Xanthomonas axonopodis* pv. *citri* and/or *Xylella fastidiosa* in citrus, *Pseudomonas syringae* pv. *actinidiae* (Psa) in kiwi, *Pseudomonas syringae* pv. *glycinea* and/or *Xanthomonas axonopodis* pv. *glycines* in soybeans, *Pseudomonas syringae* and/or *Pseudomonas syringae* pv. tomato in tomato and *Xanthomonas campestris* and/or *Xanthomonas campestris* pv. *pruni* in peaches, *Pseudomonas syringae Pseudomonas syringae* pv. *lachrymans* in cucumbers and/or *Streptomyces scabies* in potatoes.

Combinations/Formulations

The combinations of the present invention, comprising at least one host defense inducer (A) and at least one biological control agent (B) may further comprise at least one compound (C) selected from the group consisting of antimicrobial agents such as bactericides, further (conventional) antibiotics, fungicides, acaricides, nematicides, insecticides, herbicides, micronutrients and micronutrient-containing compounds, safeners, lipochito-oligosaccharide compounds (LCO) and soil-improvement products or products for reducing plant stress, in order to widen the spectrum of action or to prevent the development of resistance, for example. Within the meaning of the present invention the group of additional compounds (C) comprises compounds, which do not belong to the group of biological control agents (B) as defined herein, and also do not belong to the group of host defense inducer (A) as defined herein.

Accordingly, within the meaning of the present invention compounds (C), which are selected from the group of known or conventional antibiotics, comprise C1.1 kasugamycin, C1.2 streptomycin, C1.3 oxytetracyclin, validamycin, gentamycin, aureofungin, blasticidin-S, cycloheximide, griseofulvin, moroxydine, natamycin, polyoxins, polyoxorim and combinations thereof.

Preferred conventional antibiotics are C1.1 kasugamycin, C1.2 streptomycin, and C1.3 oxytetracyclin or combinations thereof.

Within the meaning of the present invention compounds (C), which are selected from the group of known or conventional fungicides, comprise:
(a) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl) cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(b) inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, C.2.2 penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(c) inhibitors of the respiratory chain at complex III, for example ametoctradin, amisulbrom, C.2.4 azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, C.2.3 trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(d) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(e) Compounds capable to have a multisite action, for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(f) Compounds capable to induce a host defense, for example acibenzolar-S-methyl, isotianil, probenazole and tiadinil.

(g) Inhibitors of the amino acid and/or protein biosynthesis, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(h) Inhibitors of the ATP production, for example fentin acetate, fentin chloride, fentin hydroxide and silthiofam.

(i) Inhibitors of the cell wall synthesis, for example benthiavalicarb, dimethomorph, flumorph, iprovalicarb, mandipropamid, polyoxins, polyoxorim, validamycin A and valifenalate.

(j) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(k) Inhibitors of the melanine biosynthesis, for example carpropamid, diclocymet, fenoxanil, phthalide, pyroquilon, tricyclazole and 2,2,2-trifluoroethyl {3-methyl-1-[(4-methylbenzoyl)amino]butan-2-yl}carbamate.

(l) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(m) Inhibitors of the signal transduction, for example chlozolinate, fenpiclonil, fludioxonil, iprodione, procymidone, quinoxyfen and vinclozolin.

(n) Compounds capable to act as an uncoupler, for example binapacryl, dinocap, ferimzone, fluazinam and meptyldinocap.

(o) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, C.2.1 fosetyl-aluminium (fosetyl-Al), fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrine, tebufloquin, tecloftalam, tolnifanide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(p) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate, and combinations thereof.

Preferred conventional fungicides are selected from the group consisting of C.2.1 fosetyl-Al, C.2.2 penflufen, strobilurins, particularly C.2.3 trifloxystrobin and C.2.4 azoxystrobin.

More preferred conventional fungicides are selected from the group consisting of C 2.1 fosetyl-Al and C.2.3 trifloxystrobin.

Within the meaning of the present invention compounds (C), which are selected from the group of known or conventional acaricides, nematicides and insecticides, comprise
(a) Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, and Vamidothion.

(b) GABA-gated chloride channel antagonists, for example cyclodiene organochlorines, e.g. Chlordane and Endosulfan; or phenylpyrazoles (fiproles), e.g. Ethiprole and Fipronil.

(c) Sodium channel modulators/voltage-dependent sodium channel blockers, for example pyrethroids, e.g. Acrinathrin, Allethrin, d-cis-trans Allethrin, d-trans Allethrin, C.3.5 Betacyfluthrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], C.3.6 Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, and Transfluthrin; or DDT; or Methoxychlor.

(d) Nicotinic acetylcholine receptor (nAChR) agonists, for example neonicotinoids (CNI's), e.g. C.3.1 Acetamiprid, C.3.2 Clothianidin, Dinotefuran, C.3.3 Imidacloprid, Nitenpyram, C.3.4 Thiacloprid, and Thiamethoxam; or Nicotine.

(e) Nicotinic acetylcholine receptor (nAChR) allosteric activators, for example spinosyns, e.g. Spinetoram and Spinosad.

(f) Chloride channel activators, for example avermectins/milbemycins, e.g. Abamectin, Emamectin benzoate, Lepimectin, and Milbemectin.

(g) Juvenile hormone mimics, for example juvenile hormon analogues, e.g. Hydroprene, Kinoprene, and Methoprene; or Fenoxycarb; or Pyriproxyfen.

(h) Miscellaneous non-specific (multi-site) inhibitors, for example alkyl halides, e.g. Methyl bromide and other alkyl halides; or Chloropicrin; or Sulfuryl fluoride; or Borax; or Tartar emetic.

(i) Selective homopteran feeding blockers, e.g. Pymetrozine; or Flonicamid.

(j) Mite growth inhibitors, e.g. Clofentezine, Hexythiazox, and Diflovidazin; or Etoxazole.

(k) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(l) Inhibitors of mitochondrial ATP synthase, for example Diafenthiuron; or organotin miticides, e.g. Azocyclotin, Cyhexatin, and Fenbutatin oxide; or Propargite; or Tetradifon.

(m) Uncouplers of oxidative phoshorylation via disruption of the proton gradient, for example Chlorfenapyr, DNOC, and Sulfluramid.

(n) Nicotinic acetylcholine receptor (nAChR) channel blockers, for example Bensultap, Cartap hydrochloride, Thiocyclam, and Thiosultap-sodium.

(o) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

(p) Inhibitors of chitin biosynthesis, type 1, for example Buprofezin.

(q) Moulting disruptors, for example Cyromazine.

(r) Ecdysone receptor agonists, for example Chromafenozide, Halofenozide, Methoxyfenozide, and Tebufenozide.

(s) Octopamine receptor agonists, for example Amitraz.

(t) Mitochondrial complex III electron transport inhibitors, for example Hydramethylnon; or Acequinocyl; or Fluacrypyrim.

(u) Mitochondrial complex I electron transport inhibitors, for example METI acaricides, e.g. Fenazaquin, Fenpyroximate, Pyrimidifen, Pyridaben, Tebufenpyrad, and Tolfenpyrad; or Rotenone (Derris).

(v) Voltage-dependent sodium channel blockers, e.g. Indoxacarb; or Metaflumizone.

(w) Inhibitors of acetyl CoA carboxylase, for example tetronic and tetramic acid derivatives, e.g. ketoenols such as particularly C.3.7 Spirotetramat, C.3.8 Spiromesifen, and C.3.9 Spirodiclofen.

(x) Mitochondrial complex IV electron transport inhibitors, for example phosphines, e.g. Aluminium phosphide, Calcium phosphide, Phosphine, and Zinc phosphide; or Cyanide.

(y) Mitochondrial complex II electron transport inhibitors, for example Cyenopyrafen.

(z) Ryanodine receptor modulators, for example diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl] phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2 (5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), C.3.10 Flupyradifurone, 4-{[(6-chlor-5-fluoropyridin-3-yl)methyl](methyl)amino}furan-2 (5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5- fluoropyridin-3-yl)methyl](cyclopropyl)amino}furan-2 (5H)-one (known from WO2007/115643), 4-{[(6-chloropyridin-3-yl)methyl](cyclopropyl)amino}furan-2 (5H)-one (known from EP-A-0 539 588), 4-{[(6-chlorpyridin-3-yl)methyl](methyl)amino}furan-2(5H)-one (known from EP-A-0 539 588), {[1-(6-chloropyridin-3-yl) ethyl](methyl)oxido-λ4-sulfanylidene}cyanamide (known from WO2007/149134) and its diastereomers {[(1R)-1-(6-chloropyridin-3-yl)ethyl](methyl)oxido-λ4-sulfanylidene}cyanamide (A) and {[(1S)-1-(6-chloropyridin-3-yl)ethyl](methyl)oxido-λ4-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-24-sulfanylidene]cyanamide (A1) and [(S)-methyl(oxido){(1S)-1-[6-(trifluoromethyl)pyridin-3-yl]ethyl}-24-sulfanylidene] cyanamide (A2), referred to as group of diastereomers A (known from WO2010/074747, WO2010/074751), [(R)-methyl(oxido){(1S)-1-[6-(trifluoromethyl)pyridin-3-yl] ethyl}-24-sulfanylidene]cyanamide (B1) and [(S)-methyl (oxido) {(1R)-1-[6-(trifluoromethyl)pyridin-3-yl]ethyl}-24-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5] dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H, 11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2, 3-dimethylphenyl)-2-(3,5-dimethylphenyl)ethyl]-4,5-dihydro-1,3-thiazol-2-amine (known from WO2008/ 104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/ 106457), 3-(2,5-dimethylphenyl)-4-hydroxy-8-methoxy-1, 8-diazaspiro[4.5]dec-3-en-2-one (known from WO2009/ 049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/ 099160), (2,2,3,3,4,4,5,5-octafluoropentyl)(3,3,3-trifluoropropyl)malononitrile (known from WO2005/063094), (2,2, 3,3,4,4,5,5-octafluoropentyl)(3,3,4,4,4-pentafluorobutyl) malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg.No. 1204776-60-2) (known from JP2010/ 018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/ 075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2 (5H)-one, 4-{[(6-chloropyridin-3-yl)methyl](ethyl)amino}-1,3-oxazol-2(5H)-one, 4-{[(6-chloropyridin-3-yl)methyl] (methyl)amino}-1,3-oxazol-2(5H)-one (all known from WO2010/005692), NNI-0711 (known from WO2002/ 096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/ 096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), (5RS,7RS; 5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/ 006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl) ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), and methyl 2-[3, 5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/ 049233), and combinations thereof.

Preferred compounds (C), are selected from the group of (conventional) insecticides, preferably from the groups consisting of neonicotinoids (CNI's) as particularly C.3.1 acetamiprid, C.3.2 clothianidin, C.3.3 imidacloprid and C.3.4 thiacloprid; pyrethroids as particularly C.3.5 betacyfluthrin and C.3.6 deltamethrin; ketoenols as particularly C.3.7 spirotetramat, C.3.8 spiromesifen and C.3.9 spirodiclofen; C.3.10 flupyradifurone; and combinations thereof, particularly combinations of CNI's and pyrethroids.

More preferred conventional insecticides are selected from the group consisting of C.3.3 imidacloprid, C.3.4 thiacloprid, C.3.5 betacyfluthrin, C.3.6 deltamethrin, C.3.10 flupyradifurone, and combinations thereof.

Within the meaning of the present invention compounds (C), which are selected from the group of micronutrients and micronutrient-containing compounds, comprise compounds selected from the group consisting of active ingredients containing at least one metal ion selected from the group consisting of zinc, manganese, molybdenum, iron and copper or the micronutrient boron. More preferably these micronutrients and micronutrient-containing compounds are selected from the group consisting of the zinc containing compounds Propineb, Polyoxin Z (zinc salt), Zineb, Ziram, zinc thiodazole, zinc naphthenate and Mancozeb (also containing manganese), the manganese containing compounds Maneb, Metiram and Mancopper (also containing copper), the iron containing compound Ferbam, copper (Cu) and the copper containing compounds Bordeaux mixture, Burgundy mixture, Cheshunt mixture, copper oxychloride, copper sulphate, basic copper sulphate (e.g. tribasic copper sulphate), copper oxide, copper octanoate, copper hydroxide, oxine-copper, copper ammonium acetate, copper naphthenate, chelated copper (e.g. as amino acid chelates), mancopper, acypetacs-copper, copper acetate, basic copper carbonate, copper oleate, copper silicate, copper zinc chromate, cufraneb, cuprobam, saisentong, and thiodiazole-copper, and combinations thereof.

Preferably the micronutrients and micronutrient-containing compounds are selected from the group consisting of C.4.1 copper (Cu), C.4.2 copper-hydroxyde, C.4.3 copper-sulphate, C.4.4 copper-oxychloride, C.4.5 Propineb and C.4.6 Mancozeb. More preferably the micronutrients and micronutrient-containing compounds are selected from the group consisting of C.4.2 copper-hydroxyde, C.4.3 copper-sulphate, C.4.5 Propineb and C.4.6 Mancozeb. Most preferred are C.4.5 Propineb and C.4.6 Mancozeb.

Within the meaning of the present invention compounds (C), which are selected from the group of lipochito-oligosaccharide compounds (LCO), comprise compounds having the general LCO structure, i.e. an oligomeric backbone of 0-1,4-linked N-acetyl-D-glucosamine residues with a N-linked fatty acyl chain at the non-reducing end, as described in U.S. Pat. No. 5,549,718; U.S. Pat. No. 5,646,018; U.S. Pat. No. 5,175,149; and U.S. Pat. No. 5,321,011. This basic structure may contain modifications or substitutions found in naturally occurring LCO's, such as those described in Spaink, Critical Reviews in Plant Sciences 54: 257-288, 2000; D'Haeze and Holsters, Glycobiology 12: 79R-105R, 2002. Naturally occurring LCO's are defined as compounds which can be found in nature. This basic structure may also contain modifications or substitutions which have not been found so far in naturally occurring LCO's. Examples of such analogs for which the conjugated amide bond is mimicked by a benzamide bond or which contain a function of benzylamine type are the following compounds of formula (I) which are described in WO 2005/063784 and WO 2008/071672, the content of which is incorporated herein by reference. The LCO's compounds may be isolated directly from a particular culture of Rhizobiaceae bacterial strains, synthesized chemically, or obtained chemo-enzymatically. Via the latter method, the oligosaccharide skeleton may be formed by culturing of recombinant bacterial strains, such as *Escherichia coli*, in a fermenter, and the lipid chain may then be attached chemically. LCO's used in embodiments of the invention may be recovered from natural Rhizobiaceae bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), or from bacterial strains genetically engineered to produce LCO's. These methods are known in the art and have been described, for example, in U.S. Pat. Nos. 5,549,718 and 5,646,018, which are incorporated herein by reference. Hungria and Stacey (Soil Biol. Biochem. 29: 819-830, 1997) list specific LCO structures that are produced by different rhizobial species. LCO's may be utilized in various forms of purity and may be used alone or with *rhizobia*. Methods to provide only LCO's include simply removing the rhizobial cells from a mixture of LCOs and *rhizobia*, or continuing to isolate and purify the LCO molecules through LCO solvent phase separation followed by HPLC chromatography as described by Lerouge, et. al (U.S. Pat. No. 5,549,718). Purification can be enhanced by repeated HPLC, and the purified LCO molecules can be freeze-dried for long-term storage. This method is acceptable for the production of LCO's from all genera and species of the Rhizobiaceae. Commercial products containing LCO's are available, such as OPTIMIZE® (EMD Crop BioScience). LCO compounds, which can be identical or not to naturally occurring LCO's, may also be obtained by chemical synthesis and/or through genetic engineering. Synthesis of precursor oligosaccharide molecules for the construction of LCO by genetically engineered organisms is disclosed in Samain et al., Carbohydrate Research 302: 35-42, 1997. Preparation of numerous LCOs compounds wherein the oligosaccharide skeleton is obtained by culturing recombinant bacterial strains, such as recombinant *Escherichia coli* cells harboring heterologous gene from *rhizobia*, and wherein the lipid chain is chemically attached is disclosed in WO 2005/063784 and WO 2008/07167, the content of which is incorporated herein by reference. Examples of lipochito-oligosaccharide compounds include, but are not limited to LCO compounds specifically disclosed in WO 2010/125065.

Within the meaning of the present invention compounds (C), which are selected from the group of soil-improvement products or products for reducing plant stress, comprise for example C.5 Myconate.

Further, within the meaning of the present invention the compound (C) can be selected from at least one active compound selected from the group consisting of:

Acetic acid (e.g. naphthalene acetic acid), peracetic acid, organic acids (e.g. citric acid, lactic acid), amino acids (e.g. 1-arginine), humic acids, fulvic acids, boric acid, oxolinic acid, 1,2,3-Benzothiadiazole-7-thiocarboxylic acid-S-methyl-ester, 5-hydroxy-1,4-naphthalenedione, bromo-chloro-dimethylhydantoin, Trichloroisoyanuric acid, salicylic acid, dichlorophen, kanamycin, kasugamycin, streptomycin, strepromycin sulfate, oxytetracycline, gentamycin (e.g. gentamycin sulphate hydrate), imidacloprid, tebuconazole thiabendzole, thiram, teracep, octhilinone, quinoxyfen, azadirachtin, furanoflavone, forchlorfenuron, plant minerals (e.g. calcium, calcium calcium carbonate, hypochlorite, calcium EDTA), enzymes (e.g. protease, amylase, lipase), trace elements and chelated trace elements (e.g. as amino acid chelates), vitamins and plant extracts, salicylate derivatives, bioflavonoids and organic acids derived from vegetables and fruit, natural fruit extracted polyphenols, bitter orange oil, citrus extracts, chitosan, starch, seaweed extract, organosilicone, activated ionized silicon complex (Zumsil®), bee wax, urea, *Bacillus subtilis, Bacillus amyloliquefaciens, Pseudomonas fluorescens, Pseudomonas putida, Pantoea agglomerans, Trichoderma*

*koningii, Trichoderma harzianum*, chlorine and chlorine compounds (e.g. chlorinated water, chlorine dioxide, sodium chlorite, sodium hypochlorite, hypochlorous acid, ammonium chloride, didecyl dimethyl ammonium chloride, benzalkonium chloride), oxygen, hydrogen peroxide ($H_2O_2$) and peroxygen compounds, hydrogen cyanamide, nickel (III) sulphate, sodium persulphate, phosphites such as metal phosphite as particularly aluminium ethyl phosphite, phosphate, Trisodium phosphate, phosphoric acid, inorganic nitrogen, silver and silver containing compounds (e.g. colloidal silver), glutaraldehyde, rhamnolipid (Zonix®).

Thereunder, preference is given to phosphites such as metal phosphite as particularly aluminium ethyl phosphite.

Preferably the host defense inducers and biological control agents are present in a combination comprising at least one further compound (C), which is selected from the group consisting of (conventional) bactericides, (conventional) antibiotics, (conventional) fungicides, (conventional) insecticides, (conventional) herbicides, each not belonging to the group of biological control agents (B), micronutrients and micronutrient-containing compounds, and lipochito-oligosaccharide compounds (LCO), each as defined above.

Preferably, the at least one further compound (C) is selected from the group consisting of fosetyl-Al; metal phosphites, particularly aluminium ethyl phosphite; penflufen; strobilurins as particularly trifloxystrobin; neonicotinoids (CNI's) as particularly acetamiprid, clothianidin, imidacloprid and thiacloprid, pyrethroids as particularly betacyfluthrin and deltamethrin, flupyradifurone, ketoenols as particularly spirotetramat, spiromesifen and spirodiclofen; copper- and/or zinc-containing compounds as particularly copper hydroxyde, copper sulphate, propineb and mancozeb; lipochito-oligosaccharide compounds (LCO); and conventional antibiotics selected from the group consisting of kasugamycin, streptomycin, and oxytetraclyin.

More preferably, the at least one further compound (C) is selected from the group consisting of fosetyl-Al, aluminium ethyl phosphite; trifloxystrobin; imidacloprid, thiacloprid, betacyfluthrin, deltamethrin, flupyradifurone, and combinations thereof; conventional antibiotics selected from the group consisting of kasugamycin, streptomycin, and oxytetraclyin.

A particularly preferred embodiment of the present invention relates to the use of a combination, wherein
(A) the host defense inducer is isotianil,
(B) the biological control agent is selected from the group consisting of
  1) bacteria consisting of *Bacillus subtilis* strain QST713/AQ713 (NRRL Accession No. B21661), *Bacillus subtilis* strain AQ 153 (NRRL Accession No. 55614), *Bacillus* sp. strain AQ 175 (ATCC Accession No. 55608), *Bacillus* sp. strain AQ 177 (ATCC Accession No. 55609), and *Bacillus* sp. strain AQ178 (ATCC Accession No. 53522); and
  2) fungi consisting of *Pseudozyma aphidis*, and
(C) at least one further compound is selected from the group consisting of
  fosetyl-Al; aluminium ethyl phosphite; trifloxystrobin; imidacloprid, thiacloprid, betacyfluthrin, deltamethrin, flupyradifurone, and combinations thereof; further antibiotics selected from the group consisting of kasugamycin, streptomycin, and oxytetraclyin.

An even more preferred embodiment of the present invention relates to the use of a combination, wherein
(A) the host defense inducer is a combination of isotianil and acibenzolar-S-methyl,
(B) the biological control agent is selected from the group consisting of
  1) bacteria consisting of *Bacillus subtilis* strain QST713/AQ713 (NRRL Accession No. B21661), *Bacillus subtilis* strain AQ 153 (NRRL Accession No. 55614), *Bacillus* sp. strain AQ 175 (ATCC Accession No. 55608), *Bacillus* sp. strain AQ177 (ATCC Accession No. 55609), and *Bacillus* sp. strain AQ178 (ATCC Accession No. 53522); and
  2) fungi consisting of *Pseudozyma aphidis*, and
(C) at least one further compound is selected from the group consisting of
  fosetyl-Al; aluminium ethyl phosphite; trifloxystrobin; imidacloprid, thiacloprid, betacyfluthrin, deltamethrin, flupyradifurone, and combinations thereof; further antibiotics selected from the group consisting of kasugamycin, streptomycin, and oxytetraclyin.

According to the present invention, preference is given to the following binary combinations selected from the group consisting of:
(A.1)+(B.1.1), (A.2)+(B.1.1), (A.3)+(B.1.1), (A.4)+(B.1.1),
(A.1)+(B.1.2), (A.2)+(B.1.2), (A.3)+(B.1.2), (A.4)+(B.1.2),
(A.1)+(B.1.3), (A.2)+(B.1.3), (A.3)+(B.1.3), (A.4)+(B.1.3),
(A.1)+(B.1.4), (A.2)+(B.1.4), (A.3)+(B.1.4), (A.4)+(B.1.4),
(A.1)+(B.1.5), (A.2)+(B.1.5), (A.3)+(B.1.5), (A.4)+(B.1.5),
(A.1)+(B.1.6), (A.2)+(B.1.6), (A.3)+(B.1.6), (A.4)+(B.1.6),
(A.1)+(B.1.7), (A.2)+(B.1.7), (A.3)+(B.1.7), (A.4)+(B.1.7),
(A.1)+(B.1.8), (A.2)+(B.1.8), (A.3)+(B.1.8), (A.4)+(B.1.8),
(A.1)+(B.1.9), (A.2)+(B.1.9), (A.3)+(B.1.9), (A.4)+(B.1.9),
(A.1)+(B.1.10), (A.2)+(B.1.10), (A.3)+(B.1.10), (A.4)+(B.1.10), (A.1)+(B.1.11), (A.2)+(B.1.11), (A.3)+(B.1.11), (A.4)+(B.1.11), (A.1)+(B.1.12), (A.2)+(B.1.12), (A.3)+(B.1.12), (A.4)+(B.1.12), (A.1)+(B.1.13), (A.2)+(B.1.13), (A.3)+(B.1.13), (A.4)+(B.1.13), (A.1)+(B.1.14), (A.2)+(B.1.14), (A.3)+(B.1.14), (A.4)+(B.1.14), (A.1)+(B.1.15), (A.2)+(B.1.15), (A.3)+(B.1.15), (A.4)+(B.1.15), (A.1)+(B.1.16), (A.2)+(B.1.16), (A.3)+(B.1.16), (A.4)+(B.1.16), (A.1)+(B.1.17), (A.2)+(B.1.17), (A.3)+(B.1.17), (A.4)+(B.1.17),
(A.1)+(B.2.1), (A.2)+(B.2.1), (A.3)+(B.2.1), (A.4)+(B.2.1),
(A.1)+(B.2.2), (A.2)+(B.2.2), (A.3)+(B.2.2), (A.4)+(B.2.2),
(A.1)+(B.2.3), (A.2)+(B.2.3), (A.3)+(B.2.3), (A.4)+(B.2.3),
(A.1)+(B.2.4), (A.2)+(B.2.4), (A.3)+(B.2.4), (A.4)+(B.2.4),
(A.1)+(B.2.5), (A.2)+(B.2.5), (A.3)+(B.2.5), (A.4)+(B.2.5),
(A.1)+(B.2.6), (A.2)+(B.2.6), (A.3)+(B.2.6), (A.4)+(B.2.6),
(A.1)+(B.2.7), (A.2)+(B.2.7), (A.3)+(B.2.7), (A.4)+(B.2.7),
(A.1)+(B.2.8), (A.2)+(B.2.8), (A.3)+(B.2.8), (A.4)+(B.2.8).

Out of these the following combinations are even further preferred:
(A.1)+(B.1.1), (A.2)+(B.1.1), (A.1)+(B.1.2), (A.2)+(B.1.2),
(A.1)+(B.1.3), (A.2)+(B.1.3), (A.1)+(B.1.4), (A.2)+(B.1.4),
(A.1)+(B.1.5), (A.2)+(B.1.5), (A.1)+(B.1.6), (A.2)+(B.1.6),
(A.1)+(B.1.7), (A.2)+(B.1.7), (A.1)+(B.1.8), (A.2)+(B.1.8),
(A.1)+(B.1.9), (A.2)+(B.1.9), (A.1)+(B.1.10), (A.2)+(B.1.10), (A.1)+(B.1.11), (A.2)+(B.1.11),
(A.1)+(B.2.1), (A.2)+(B.2.1).

Most preference is given to the following combinations:
(A.1)+(B.1.1), (A.2)+(B.1.1), (A.1)+(B.1.2), (A.2)+(B.1.2),
(A.1)+(B.1.3), (A.2)+(B.1.3), (A.1)+(B.1.4), (A.2)+(B.1.4),
(A.1)+(B.1.5), (A.2)+(B.1.5),
(A.1)+(B.2.1), (A.2)+(B.2.1).

There from the combination (A.2)+(B.1.1) is even most preferred.

All binary combinations mentioned above can be combined with at least one further known bactericide, antibiotic, fungicide, acaricide, nematicide, herbicide, insecticide, micronutrients and micronutrient-containing compound, safener, lipochito-oligosaccharides (LCO), soil-improvement product or product for reducing plant stress, for example Myconate, in order to widen the spectrum of action or to prevent the development of resistance, for example.

According to the present invention, preference is given to the following ternary combinations selected from the group consisting of:
(A.1)+(A.2)+(B.1.1), (A.1)+(A.2)+(B.1.2), (A.1)+(A.2)+(B.1.3), (A.1)+(A.2)+(B.1.4), (A.1)+(A.2)+(B.1.5), (A.1)+(A.2)+(B.1.6), (A.1)+(A.2)+(B.1.7), (A.1)+(A.2)+(B.1.8), (A.1)+(A.2)+(B.1.9), (A.1)+(A.2)+(B.1.10), (A.1)+(A.2)+(B.1.11), (A.1)+(A.2)+(B.2.1.).

Preference is also given to the following quaternary combinations selected from the group consisting of:
(A.1)+(A.2)+(B.1.1)+(C.1.1), (A.1)+(A.2)+(B.1.1)+(C.1.2), (A.1)+(A.2)+(B.1.1)+(C.1.3), (A.1)+(A.2)+(B.1.1)+(C.2.1), (A.1)+(A.2)+(B.1.1)+(C.2.3), (A.1)+(A.2)+(B.1.1)+(C.3.3), (A.1)+(A.2)+(B.1.1)+(C.3.10), (A.1)+(A.2)+(B.1.1)+(C.4.5), (A.1)+(A.2)+(B.1.1)+(C.4.6), (A.1)+(A.2)+(B.1.1)+(C.5),
(A.1)+(A.2)+(B.1.2)+(C.1.1), (A.1)+(A.2)+(B.1.2)+(C.1.2), (A.1)+(A.2)+(B.1.2)+(C.1.3), (A.1)+(A.2)+(B.1.2)+(C.2.1), (A.1)+(A.2)+(B.1.2)+(C.2.3), (A.1)+(A.2)+(B.1.2)+(C.3.3), (A.1)+(A.2)+(B.1.2)+(C.3.10), (A.1)+(A.2)+(B.1.2)+(C.4.5), (A.1)+(A.2)+(B.1.2)+(C.4.6), (A.1)+(A.2)+(B.1.2)+(C.5),
(A.1)+(A.2)+(B.1.3)+(C.1.1), (A.1)+(A.2)+(B.1.3)+(C.1.2), (A.1)+(A.2)+(B.1.3)+(C.1.3), (A.1)+(A.2)+(B.1.3)+(C.2.1), (A.1)+(A.2)+(B.1.3)+(C.2.3), (A.1)+(A.2)+(B.1.3)+(C.3.3), (A.1)+(A.2)+(B.1.3)+(C.3.10), (A.1)+(A.2)+(B.1.3)+(C.4.5), (A.1)+(A.2)+(B.1.3)+(C.4.6), (A.1)+(A.2)+(B.1.3)+(C.5),
(A.1)+(A.2)+(B.1.4)+(C.1.1), (A.1)+(A.2)+(B.1.4)+(C.1.2), (A.1)+(A.2)+(B.1.4)+(C.1.3), (A.1)+(A.2)+(B.1.4)+(C.2.1), (A.1)+(A.2)+(B.1.4)+(C.2.3), (A.1)+(A.2)+(B.1.4)+(C.3.3), (A.1)+(A.2)+(B.1.4)+(C.3.10), (A.1)+(A.2)+(B.1.4)+(C.4.5), (A.1)+(A.2)+(B.1.4)+(C.4.6), (A.1)+(A.2)+(B.1.4)+(C.5),
(A.1)+(A.2)+(B.1.5)+(C.1.1), (A.1)+(A.2)+(B.1.5)+(C.1.2), (A.1)+(A.2)+(B.1.5)+(C.1.3), (A.1)+(A.2)+(B.1.5)+(C.2.1), (A.1)+(A.2)+(B.1.5)+(C.2.3), (A.1)+(A.2)+(B.1.5)+(C.3.3), (A.1)+(A.2)+(B.1.5)+(C.3.10), (A.1)+(A.2)+(B.1.5)+(C.4.5), (A.1)+(A.2)+(B.1.5)+(C.4.6), (A.1)+(A.2)+(B.1.5)+(C.5),
(A.1)+(A.2)+(B.1.6)+(C.1.1), (A.1)+(A.2)+(B.1.6)+(C.1.2), (A.1)+(A.2)+(B.1.6)+(C.1.3), (A.1)+(A.2)+(B.1.6)+(C.2.1), (A.1)+(A.2)+(B.1.6)+(C.2.3), (A.1)+(A.2)+(B.1.6)+(C.3.3), (A.1)+(A.2)+(B.1.6)+(C.3.10), (A.1)+(A.2)+(B.1.6)+(C.4.5), (A.1)+(A.2)+(B.1.6)+(C.4.6), (A.1)+(A.2)+(B.1.6)+(C.5),
(A.1)+(A.2)+(B.1.7)+(C.1.1), (A.1)+(A.2)+(B.1.7)+(C.1.2), (A.1)+(A.2)+(B.1.7)+(C.1.3), (A.1)+(A.2)+(B.1.7)+(C.2.1), (A.1)+(A.2)+(B.1.7)+(C.2.3), (A.1)+(A.2)+(B.1.7)+(C.3.3), (A.1)+(A.2)+(B.1.7)+(C.3.10), (A.1)+(A.2)+(B.1.7)+(C.4.5), (A.1)+(A.2)+(B.1.7)+(C.4.6), (A.1)+(A.2)+(B.1.7)+(C.5),
(A.1)+(A.2)+(B.1.8)+(C.1.1), (A.1)+(A.2)+(B.1.8)+(C.1.2), (A.1)+(A.2)+(B.1.8)+(C.1.3), (A.1)+(A.2)+(B.1.8)+(C.2.1), (A.1)+(A.2)+(B.1.8)+(C.2.3), (A.1)+(A.2)+(B.1.8)+(C.3.3), (A.1)+(A.2)+(B.1.8)+(C.3.10), (A.1)+(A.2)+(B.1.8)+(C.4.5), (A.1)+(A.2)+(B.1.8)+(C.4.6), (A.1)+(A.2)+(B.1.8)+(C.5),
(A.1)+(A.2)+(B.1.9)+(C.1.1), (A.1)+(A.2)+(B.1.9)+(C.1.2), (A.1)+(A.2)+(B.1.9)+(C.1.3), (A.1)+(A.2)+(B.1.9)+(C.2.1), (A.1)+(A.2)+(B.1.9)+(C.2.3), (A.1)+(A.2)+(B.1.9)+(C.3.3), (A.1)+(A.2)+(B.1.9)+(C.3.10), (A.1)+(A.2)+(B.1.9)+(C.4.5), (A.1)+(A.2)+(B.1.9)+(C.4.6), (A.1)+(A.2)+(B.1.9)+(C.5),
(A.1)+(A.2)+(B.1.10)+(C.1.1), (A.1)+(A.2)+(B.1.10)+(C.1.2), (A.1)+(A.2)+(B.1.10)+(C.1.3), (A.1)+(A.2)+(B.1.10)+(C.2.1), (A.1)+(A.2)+(B.1.10)+(C.2.3), (A.1)+(A.2)+(B.1.10)+(C.3.3), (A.1)+(A.2)+(B.1.10)+(C.3.10), (A.1)+(A.2)+(B.1.10)+(C.4.5), (A.1)+(A.2)+(B.1.10)+(C.4.6), (A.1)+(A.2)+(B.1.10)+(C.5),
(A.1)+(A.2)+(B.1.11)+(C.1.1), (A.1)+(A.2)+(B.1.11)+(C.1.2), (A.1)+(A.2)+(B.1.11)+(C.1.3), (A.1)+(A.2)+(B.1.11)+(C.2.1), (A.1)+(A.2)+(B.1.11)+(C.2.3), (A.1)+(A.2)+(B.1.11)+(C.3.3), (A.1)+(A.2)+(B.1.11)+(C.3.10), (A.1)+(A.2)+(B.1.11)+(C.4.5), (A.1)+(A.2)+(B.1.11)+(C.4.6), (A.1)+(A.2)+(B.1.11)+(C.5),
(A.1)+(A.2)+(B.2.1)+(C.1.1), (A.1)+(A.2)+(B.2.1)+(C.1.2), (A.1)+(A.2)+(B.2.1)+(C.1.3), (A.1)+(A.2)+(B.2.1)+(C.2.1), (A.1)+(A.2)+(B.2.1)+(C.2.3), (A.1)+(A.2)+(B.2.1)+(C.3.3), (A.1)+(A.2)+(B.2.1)+(C.3.10), (A.1)+(A.2)+(B.2.1)+(C.4.5), (A.1)+(A.2)+(B.2.1)+(C.4.6), (A.1)+(A.2)+(B.2.1)+(C.5), According to the present invention, preference is also given to the following ternary combinations selected from the group consisting of:
(A.1)+(B.1.1)+(C.1.1), (A.2)+(B.1.1)+(C.1.1), (A.3)+(B.1.1)+(C.1.1), (A.4)+(B.1.1)+(C.1.1), (A.1)+(B.1.2)+(C.1.1), (A.2)+(B.1.2)+(C.1.1), (A.3)+(B.1.2)+(C.1.1), (A.4)+(B.1.2)+(C.1.1), (A.1)+(B.1.3)+(C.1.1), (A.2)+(B.1.3)+(C.1.1), (A.3)+(B.1.3)+(C.1.1), (A.4)+(B.1.3)+(C.1.1), (A.1)+(B.1.4)+(C.1.1), (A.2)+(B.1.4)+(C.1.1), (A.3)+(B.1.4)+(C.1.1), (A.4)+(B.1.4)+(C.1.1), (A.1)+(B.1.5)+(C.1.1), (A.2)+(B.1.5)+(C.1.1), (A.3)+(B.1.5)+(C.1.1), (A.4)+(B.1.5)+(C.1.1), (A.1)+(B.1.6)+(C.1.1), (A.2)+(B.1.6)+(C.1.1), (A.3)+(B.1.6)+(C.1.1), (A.4)+(B.1.6)+(C.1.1), (A.1)+(B.1.7)+(C.1.1), (A.2)+(B.1.7)+(C.1.1), (A.3)+(B.1.7)+(C.1.1), (A.4)+(B.1.7)+(C.1.1), (A.1)+(B.1.8)+(C.1.1), (A.2)+(B.1.8)+(C.1.1), (A.3)+(B.1.8)+(C.1.1), (A.4)+(B.1.8)+(C.1.1), (A.1)+(B.1.9)+(C.1.1), (A.2)+(B.1.9)+(C.1.1), (A.3)+(B.1.9)+(C.1.1), (A.4)+(B.1.9)+(C.1.1), (A.1)+(B.1.10)+(C.1.1), (A.2)+(B.1.10)+(C.1.1), (A.3)+(B.1.10)+(C.1.1), (A.4)+(B.1.10)+(C.1.1), (A.1)+(B.1.11)+(C.1.1), (A.2)+(B.1.11)+(C.1.1), (A.3)+(B.1.11)+(C.1.1), (A.4)+(B.1.11)+(C.1.1), (A.1)+(B.1.12)+(C.1.1), (A.2)+(B.1.12)+(C.1.1), (A.3)+(B.1.12)+(C.1.1), (A.4)+(B.1.12)+(C.1.1), (A.1)+(B.1.13)+(C.1.1), (A.2)+(B.1.13)+(C.1.1), (A.3)+(B.1.13)+(C.1.1), (A.4)+(B.1.13)+(C.1.1), (A.1)+(B.1.14)+(C.1.1), (A.2)+(B.1.14)+(C.1.1), (A.3)+(B.1.14)+(C.1.1), (A.4)+(B.1.14)+(C.1.1), (A.1)+(B.1.15)+(C.1.1), (A.2)+(B.1.15)+(C.1.1), (A.3)+(B.1.15)+(C.1.1), (A.4)+(B.1.15)+(C.1.1), (A.1)+(B.1.16)+(C.1.1), (A.2)+(B.1.16)+(C.1.1), (A.3)+(B.1.16)+(C.1.1), (A.4)+(B.1.16)+(C.1.1), (A.1)+(B.1.17)+(C.1.1), (A.2)+(B.1.17)+(C.1.1), (A.3)+(B.1.17)+(C.1.1), (A.4)+(B.1.17)+(C.1.1),
(A.1)+(B.2.1)+(C.1.1), (A.2)+(B.2.1)+(C.1.1), (A.3)+(B.2.1)+(C.1.1), (A.4)+(B.2.1)+(C.1.1), (A.1)+(B.2.2)+(C.1.1), (A.2)+(B.2.2)+(C.1.1), (A.3)+(B.2.2)+(C.1.1), (A.4)+(B.2.2)+(C.1.1), (A.1)+(B.2.3)+(C.1.1), (A.2)+(B.2.3)+(C.1.1), (A.3)+(B.2.3)+(C.1.1), (A.4)+(B.2.3)+(C.1.1), (A.1)+(B.2.4)+(C.1.1), (A.2)+(B.2.4)+(C.1.1), (A.3)+(B.2.4)+(C.1.1), (A.4)+(B.2.4)+(C.1.1), (A.1)+(B.2.5)+(C.1.1), (A.2)+(B.2.5)+(C.1.1), (A.3)+(B.2.5)+(C.1.1), (A.4)+(B.2.5)+(C.1.1), (A.1)+(B.2.6)+(C.1.1), (A.2)+(B.2.6)+(C.1.1), (A.3)+(B.2.6)+(C.1.1), (A.4)+(B.2.6)+(C.1.1), (A.1)+(B.2.7)+(C.1.1), (A.2)+(B.2.7)+(C.1.1), (A.3)+(B.2.7)+(C.1.1), (A.4)+(B.2.7)+(C.1.1), (A.1)+(B.2.8)+(C.1.1), (A.2)+(B.2.8)+(C.1.1), (A.3)+(B.2.8)+(C.1.1), (A.4)+(B.2.8)+(C.1.1).

(A.1)+(B.1.1)+(C.1.2), (A.2)+(B.1.1)+(C.1.2), (A.3)+(B.1.1)+(C.1.2), (A.4)+(B.1.1)+(C.1.2), (A.1)+(B.1.2)+(C.1.2), (A.2)+(B.1.2)+(C.1.2), (A.3)+(B.1.2)+(C.1.2), (A.4)+(B.1.2)+(C.1.2), (A.1)+(B.1.3)+(C.1.2), (A.2)+(B.1.3)+(C.1.2), (A.3)+(B.1.3)+(C.1.2), (A.4)+(B.1.3)+(C.1.2), (A.1)+(B.1.4)+(C.1.2), (A.2)+(B.1.4)+(C.1.2), (A.3)+(B.1.4)+(C.1.2), (A.4)+(B.1.4)+(C.1.2), (A.1)+(B.1.5)+(C.1.2), (A.2)+(B.1.5)+(C.1.2), (A.3)+(B.1.5)+(C.1.2), (A.4)+(B.1.5)+(C.1.2), (A.1)+(B.1.6)+(C.1.2), (A.2)+(B.1.6)+(C.1.2), (A.3)+(B.1.6)+(C.1.2), (A.4)+(B.1.6)+(C.1.2), (A.1)+(B.1.7)+(C.1.2), (A.2)+(B.1.7)+(C.1.2), (A.3)+(B.1.7)+(C.1.2), (A.4)+(B.1.7)+(C.1.2), (A.1)+(B.1.8)+(C.1.2), (A.2)+(B.1.8)+(C.1.2), (A.3)+(B.1.8)+(C.1.2), (A.4)+(B.1.8)+(C.1.2), (A.1)+(B.1.9)+(C.1.2), (A.2)+(B.1.9)+(C.1.2), (A.3)+(B.1.9)+(C.1.2), (A.4)+(B.1.9)+(C.1.2), (A.1)+(B.1.10)+(C.1.2), (A.2)+(B.1.10)+(C.1.2), (A.3)+(B.1.10)+(C.1.2), (A.4)+(B.1.10)+(C.1.2), (A.1)+(B.1.11)+(C.1.2), (A.2)+(B.1.11)+(C.1.2), (A.3)+(B.1.11)+(C.1.2), (A.4)+(B.1.11)+(C.1.2), (A.1)+(B.1.12)+(C.1.2), (A.2)+(B.1.12)+(C.1.2), (A.3)+(B.1.12)+(C.1.2), (A.4)+(B.1.12)+(C.1.2), (A.1)+(B.1.13)+(C.1.2), (A.2)+(B.1.13)+(C.1.2), (A.3)+(B.1.13)+(C.1.2), (A.4)+(B.1.13)+(C.1.2), (A.1)+(B.1.14)+(C.1.2), (A.2)+(B.1.14)+(C.1.2), (A.3)+(B.1.14)+(C.1.2), (A.4)+(B.1.14)+(C.1.2), (A.1)+(B.1.15)+(C.1.2), (A.2)+(B.1.15)+(C.1.2), (A.3)+(B.1.15)+(C.1.2), (A.4)+(B.1.15)+(C.1.2), (A.1)+(B.1.16)+(C.1.2), (A.2)+(B.1.16)+(C.1.2), (A.3)+(B.1.16)+(C.1.2), (A.4)+(B.1.16)+(C.1.2), (A.1)+(B.1.17)+(C.1.2), (A.2)+(B.1.17)+(C.1.2), (A.3)+(B.1.17)+(C.1.2), (A.4)+(B.1.17)+(C.1.2), (A.1)+(B.2.1)+(C.1.2), (A.2)+(B.2.1)+(C.1.2), (A.3)+(B.2.1)+(C.1.2), (A.4)+(B.2.1)+(C.1.2), (A.1)+(B.2.2)+(C.1.2), (A.2)+(B.2.2)+(C.1.2), (A.3)+(B.2.2)+(C.1.2), (A.4)+(B.2.2)+(C.1.2), (A.1)+(B.2.3)+(C.1.2), (A.2)+(B.2.3)+(C.1.2), (A.3)+(B.2.3)+(C.1.2), (A.4)+(B.2.3)+(C.1.2), (A.1)+(B.2.4)+(C.1.2), (A.2)+(B.2.4)+(C.1.2), (A.3)+(B.2.4)+(C.1.2), (A.4)+(B.2.4)+(C.1.2), (A.1)+(B.2.5)+(C.1.2), (A.2)+(B.2.5)+(C.1.2), (A.3)+(B.2.5)+(C.1.2), (A.4)+(B.2.5)+(C.1.2), (A.1)+(B.2.6)+(C.1.2), (A.2)+(B.2.6)+(C.1.2), (A.3)+(B.2.6)+(C.1.2), (A.4)+(B.2.6)+(C.1.2), (A.1)+(B.2.7)+(C.1.2), (A.2)+(B.2.7)+(C.1.2), (A.3)+(B.2.7)+(C.1.2), (A.4)+(B.2.7)+(C.1.2), (A.1)+(B.2.8)+(C.1.2), (A.2)+(B.2.8)+(C.1.2), (A.3)+(B.2.8)+(C.1.2), (A.4)+(B.2.8)+(C.1.2).

(A.1)+(B.1.1)+(C.1.3), (A.2)+(B.1.1)+(C.1.3), (A.3)+(B.1.1)+(C.1.3), (A.4)+(B.1.1)+(C.1.3), (A.1)+(B.1.2)+(C.1.3), (A.2)+(B.1.2)+(C.1.3), (A.3)+(B.1.2)+(C.1.3), (A.4)+(B.1.2)+(C.1.3), (A.1)+(B.1.3)+(C.1.3), (A.2)+(B.1.3)+(C.1.3), (A.3)+(B.1.3)+(C.1.3), (A.4)+(B.1.3)+(C.1.3), (A.1)+(B.1.4)+(C.1.3), (A.2)+(B.1.4)+(C.1.3), (A.3)+(B.1.4)+(C.1.3), (A.4)+(B.1.4)+(C.1.3), (A.1)+(B.1.5)+(C.1.3), (A.2)+(B.1.5)+(C.1.3), (A.3)+(B.1.5)+(C.1.3), (A.4)+(B.1.5)+(C.1.3), (A.1)+(B.1.6)+(C.1.3), (A.2)+(B.1.6)+(C.1.3), (A.3)+(B.1.6)+(C.1.3), (A.4)+(B.1.6)+(C.1.3), (A.1)+(B.1.7)+(C.1.3), (A.2)+(B.1.7)+(C.1.3), (A.3)+(B.1.7)+(C.1.3), (A.4)+(B.1.7)+(C.1.3), (A.1)+(B.1.8)+(C.1.3), (A.2)+(B.1.8)+(C.1.3), (A.3)+(B.1.8)+(C.1.3), (A.4)+(B.1.8)+(C.1.3), (A.1)+(B.1.9)+(C.1.3), (A.2)+(B.1.9)+(C.1.3), (A.3)+(B.1.9)+(C.1.3), (A.4)+(B.1.9)+(C.1.3), (A.1)+(B.1.10)+(C.1.3), (A.2)+(B.1.10)+(C.1.3), (A.3)+(B.1.10)+(C.1.3), (A.4)+(B.1.10)+(C.1.3), (A.1)+(B.1.11)+(C.1.3), (A.2)+(B.1.11)+(C.1.3), (A.3)+(B.1.11)+(C.1.3), (A.4)+(B.1.11)+(C.1.3), (A.1)+(B.1.12)+(C.1.3), (A.2)+(B.1.12)+(C.1.3), (A.3)+(B.1.12)+(C.1.3), (A.4)+(B.1.12)+(C.1.3), (A.1)+(B.1.13)+(C.1.3), (A.2)+(B.1.13)+(C.1.3), (A.3)+(B.1.13)+(C.1.3), (A.4)+(B.1.13)+(C.1.3), (A.1)+(B.1.14)+(C.1.3), (A.2)+(B.1.14)+(C.1.3), (A.3)+(B.1.14)+(C.1.3), (A.4)+(B.1.14)+(C.1.3), (A.1)+(B.1.15)+(C.1.3), (A.2)+(B.1.15)+(C.1.3), (A.3)+(B.1.15)+(C.1.3), (A.4)+(B.1.15)+(C.1.3), (A.1)+(B.1.16)+(C.1.3), (A.2)+(B.1.16)+(C.1.3), (A.3)+(B.1.16)+(C.1.3), (A.4)+(B.1.16)+(C.1.3), (A.1)+(B.1.17)+(C.1.3), (A.2)+(B.1.17)+(C.1.3), (A.3)+(B.1.17)+(C.1.3), (A.4)+(B.1.17)+(C.1.3), (A.1)+(B.2.1)+(C.1.3), (A.2)+(B.2.1)+(C.1.3), (A.3)+(B.2.1)+(C.1.3), (A.4)+(B.2.1)+(C.1.3), (A.1)+(B.2.2)+(C.1.3), (A.2)+(B.2.2)+(C.1.3), (A.3)+(B.2.2)+(C.1.3), (A.4)+(B.2.2)+(C.1.3), (A.1)+(B.2.3)+(C.1.3), (A.2)+(B.2.3)+(C.1.3), (A.3)+(B.2.3)+(C.1.3), (A.4)+(B.2.3)+(C.1.3), (A.1)+(B.2.4)+(C.1.3), (A.2)+(B.2.4)+(C.1.3), (A.3)+(B.2.4)+(C.1.3), (A.4)+(B.2.4)+(C.1.3), (A.1)+(B.2.5)+(C.1.3), (A.2)+(B.2.5)+(C.1.3), (A.3)+(B.2.5)+(C.1.3), (A.4)+(B.2.5)+(C.1.3), (A.1)+(B.2.6)+(C.1.3), (A.2)+(B.2.6)+(C.1.3), (A.3)+(B.2.6)+(C.1.3), (A.4)+(B.2.6)+(C.1.3), (A.1)+(B.2.7)+(C.1.3), (A.2)+(B.2.7)+(C.1.3), (A.3)+(B.2.7)+(C.1.3), (A.4)+(B.2.7)+(C.1.3), (A.1)+(B.2.8)+(C.1.3), (A.2)+(B.2.8)+(C.1.3), (A.3)+(B.2.8)+(C.1.3), (A.4)+(B.2.8)+(C.1.3).

(A.1)+(B.1.1)+(C.2.1), (A.2)+(B.1.1)+(C.2.1), (A.3)+(B.1.1)+(C.2.1), (A.4)+(B.1.1)+(C.2.1), (A.1)+(B.1.2)+(C.2.1), (A.2)+(B.1.2)+(C.2.1), (A.3)+(B.1.2)+(C.2.1), (A.4)+(B.1.2)+(C.2.1), (A.1)+(B.1.3)+(C.2.1), (A.2)+(B.1.3)+(C.2.1), (A.3)+(B.1.3)+(C.2.1), (A.4)+(B.1.3)+(C.2.1), (A.1)+(B.1.4)+(C.2.1), (A.2)+(B.1.4)+(C.2.1), (A.3)+(B.1.4)+(C.2.1), (A.4)+(B.1.4)+(C.2.1), (A.1)+(B.1.5)+(C.2.1), (A.2)+(B.1.5)+(C.2.1), (A.3)+(B.1.5)+(C.2.1), (A.4)+(B.1.5)+(C.2.1), (A.1)+(B.1.6)+(C.2.1), (A.2)+(B.1.6)+(C.2.1), (A.3)+(B.1.6)+(C.2.1), (A.4)+(B.1.6)+(C.2.1), (A.1)+(B.1.7)+(C.2.1), (A.2)+(B.1.7)+(C.2.1), (A.3)+(B.1.7)+(C.2.1), (A.4)+(B.1.7)+(C.2.1), (A.1)+(B.1.8)+(C.2.1), (A.2)+(B.1.8)+(C.2.1), (A.3)+(B.1.8)+(C.2.1), (A.4)+(B.1.8)+(C.2.1), (A.1)+(B.1.9)+(C.2.1), (A.2)+(B.1.9)+(C.2.1), (A.3)+(B.1.9)+(C.2.1), (A.4)+(B.1.9)+(C.2.1), (A.1)+(B.1.10)+(C.2.1), (A.2)+(B.1.10)+(C.2.1), (A.3)+(B.1.10)+(C.2.1), (A.4)+(B.1.10)+(C.2.1), (A.1)+(B.1.11)+(C.2.1), (A.2)+(B.1.11)+(C.2.1), (A.3)+(B.1.11)+(C.2.1), (A.4)+(B.1.11)+(C.2.1), (A.1)+(B.1.12)+(C.2.1), (A.2)+(B.1.12)+(C.2.1), (A.3)+(B.1.12)+(C.2.1), (A.4)+(B.1.12)+(C.2.1), (A.1)+(B.1.13)+(C.2.1), (A.2)+(B.1.13)+(C.2.1), (A.3)+(B.1.13)+(C.2.1), (A.4)+(B.1.13)+(C.2.1), (A.1)+(B.1.14)+(C.2.1), (A.2)+(B.1.14)+(C.2.1), (A.3)+(B.1.14)+(C.2.1), (A.4)+(B.1.14)+(C.2.1), (A.1)+(B.1.15)+(C.2.1), (A.2)+(B.1.15)+(C.2.1), (A.3)+(B.1.15)+(C.2.1), (A.4)+(B.1.15)+(C.2.1), (A.1)+(B.1.16)+(C.2.1), (A.2)+(B.1.16)+(C.2.1), (A.3)+(B.1.16)+(C.2.1), (A.4)+(B.1.16)+(C.2.1), (A.1)+(B.1.17)+(C.2.1), (A.2)+(B.1.17)+(C.2.1), (A.3)+(B.1.17)+(C.2.1), (A.4)+(B.1.17)+(C.2.1), (A.1)+(B.2.1)+(C.2.1), (A.2)+(B.2.1)+(C.2.1), (A.3)+(B.2.1)+(C.2.1), (A.4)+(B.2.1)+(C.2.1), (A.1)+(B.2.2)+(C.2.1), (A.2)+(B.2.2)+(C.2.1), (A.3)+(B.2.2)+(C.2.1), (A.4)+(B.2.2)+(C.2.1), (A.1)+(B.2.3)+(C.2.1), (A.2)+(B.2.3)+(C.2.1), (A.3)+(B.2.3)+(C.2.1), (A.4)+(B.2.3)+(C.2.1), (A.1)+(B.2.4)+(C.2.1), (A.2)+(B.2.4)+(C.2.1), (A.3)+(B.2.4)+(C.2.1), (A.4)+(B.2.4)+(C.2.1), (A.1)+(B.2.5)+(C.2.1), (A.2)+(B.2.5)+(C.2.1), (A.3)+(B.2.5)+(C.2.1), (A.4)+(B.2.5)+(C.2.1), (A.1)+(B.2.6)+(C.2.1), (A.2)+(B.2.6)+(C.2.1), (A.3)+(B.2.6)+(C.2.1), (A.4)+(B.2.6)+(C.2.1), (A.1)+(B.2.7)+(C.2.1), (A.2)+(B.2.7)+(C.2.1), (A.3)+(B.2.7)+(C.2.1), (A.4)+(B.2.7)+(C.2.1), (A.1)+(B.2.8)+(C.2.1), (A.2)+(B.2.8)+(C.2.1), (A.3)+(B.2.8)+(C.2.1), (A.4)+(B.2.8)+(C.2.1).

(A.1)+(B.1.1)+(C.2.2), (A.2)+(B.1.1)+(C.2.2), (A.3)+(B.1.1)+(C.2.2), (A.4)+(B.1.1)+(C.2.2), (A.1)+(B.1.2)+(C.2.2), (A.2)+(B.1.2)+(C.2.2), (A.3)+(B.1.2)+(C.2.2), (A.4)+(B.1.2)+(C.2.2), (A.1)+(B.1.3)+(C.2.2), (A.2)+(B.1.3)+(C.2.2), (A.3)+(B.1.3)+(C.2.2), (A.4)+(B.1.3)+(C.2.2), (A.1)+(B.1.4)+(C.2.2), (A.2)+(B.1.4)+(C.2.2), (A.3)+(B.1.4)+(C.2.2), (A.4)+(B.1.4)+(C.2.2), (A.1)+(B.1.5)+(C.2.2), (A.2)+(B.1.5)+(C.2.2), (A.3)+(B.1.5)+(C.2.2), (A.4)+(B.1.5)+(C.2.2), (A.1)+(B.1.6)+(C.2.2), (A.2)+(B.1.6)+(C.2.2), (A.3)+(B.1.6)+(C.2.2), (A.4)+(B.1.6)+(C.2.2), (A.1)+(B.1.7)+(C.2.2), (A.2)+(B.1.7)+(C.2.2), (A.3)+(B.1.7)+(C.2.2), (A.4)+(B.1.7)+(C.2.2), (A.1)+(B.1.8)+(C.2.2), (A.2)+(B.1.8)+(C.2.2), (A.3)+(B.1.8)+(C.2.2), (A.4)+(B.1.8)+(C.2.2), (A.1)+(B.1.9)+(C.2.2), (A.2)+(B.1.9)+(C.2.2), (A.3)+(B.1.9)+(C.2.2), (A.4)+(B.1.9)+(C.2.2), (A.1)+(B.1.10)+(C.2.2), (A.2)+(B.1.10)+(C.2.2), (A.3)+(B.1.10)+(C.2.2), (A.4)+(B.1.10)+(C.2.2), (A.1)+(B.11.11)+(C.2.2), (A.2)+(B.11.11)+(C.2.2), (A.3)+(B.11.11)+(C.2.2), (A.4)+(B.1.11)+(C.2.2), (A.1)+(B.1.12)+(C.2.2), (A.2)+(B.1.12)+(C.2.2), (A.3)+(B.1.12)+(C.2.2), (A.4)+(B.1.12)+(C.2.2), (A.1)+(B.1.13)+(C.2.2), (A.2)+(B.1.13)+(C.2.2), (A.3)+(B.1.13)+(C.2.2), (A.4)+(B.1.13)+(C.2.2), (A.1)+(B.1.14)+(C.2.2), (A.2)+(B.1.14)+(C.2.2), (A.3)+(B.1.14)+(C.2.2), (A.4)+(B.1.14)+(C.2.2), (A.1)+(B.1.15)+(C.2.2), (A.2)+(B.1.15)+(C.2.2), (A.3)+(B.1.15)+(C.2.2), (A.4)+(B.1.15)+(C.2.2), (A.1)+(B.1.16)+(C.2.2), (A.2)+(B.1.16)+(C.2.2), (A.3)+(B.1.16)+(C.2.2), (A.4)+(B.1.16)+(C.2.2), (A.1)+(B.1.17)+(C.2.2), (A.2)+(B.1.17)+(C.2.2), (A.3)+(B.1.17)+(C.2.2), (A.4)+(B.1.17)+(C.2.2), (A1.1)+(B.2.1)+(C.2.2), (A.2)+(B.2.1)+(C.2.2), (A.3)+(B.2.1)+(C.2.2), (A.4)+(B.2.1)+(C.2.2), (A.1)+(B.2.2)+(C.2.2), (A.2)+(B.2.2)+(C.2.2), (A.3)+(B.2.2)+(C.2.2), (A.4)+(B.2.2)+(C.2.2), (A.1)+(B.2.3)+(C.2.2), (A.2)+(B.2.3)+(C.2.2), (A.3)+(B.2.3)+(C.2.2), (A.4)+(B.2.3)+(C.2.2), (A.1)+(B.2.4)+(C.2.2), (A.2)+(B.2.4)+(C.2.2), (A.3)+(B.2.4)+(C.2.2), (A.4)+(B.2.4)+(C.2.2), (A.1)+(B.2.5)+(C.2.2), (A.2)+(B.2.5)+(C.2.2), (A.3)+(B.2.5)+(C.2.2), (A.4)+(B.2.5)+(C.2.2), (A.1)+(B.2.6)+(C.2.2), (A.2)+(B.2.6)+(C.2.2), (A.3)+(B.2.6)+(C.2.2), (A.4)+(B.2.6)+(C.2.2), (A.1)+(B.2.7)+(C.2.2), (A.2)+(B.2.7)+(C.2.2), (A.3)+(B.2.7)+(C.2.2), (A.4)+(B.2.7)+(C.2.2), (A.1)+(B.2.8)+(C.2.2), (A.2)+(B.2.8)+(C.2.2), (A.3)+(B.2.8)+(C.2.2), (A.4)+(B.2.8)+(C.2.2).

(A.1)+(B.1.1)+(C.2.3), (A.2)+(B.1.1)+(C.2.3), (A.3)+(B.1.1)+(C.2.3), (A.4)+(B.1.1)+(C.2.3), (A.1)+(B.1.2)+(C.2.3), (A.2)+(B.1.2)+(C.2.3), (A.3)+(B.1.2)+(C.2.3), (A.4)+(B.1.2)+(C.2.3), (A.1)+(B.1.3)+(C.2.3), (A.2)+(B.1.3)+(C.2.3), (A.3)+(B.1.3)+(C.2.3), (A.4)+(B.1.3)+(C.2.3), (A.1)+(B.1.4)+(C.2.3), (A.2)+(B.1.4)+(C.2.3), (A.3)+(B.1.4)+(C.2.3), (A.4)+(B.1.4)+(C.2.3), (A.1)+(B.1.5)+(C.2.3), (A.2)+(B.1.5)+(C.2.3), (A.3)+(B.1.5)+(C.2.3), (A.4)+(B.1.5)+(C.2.3), (A.1)+(B.1.6)+(C.2.3), (A.2)+(B.1.6)+(C.2.3), (A.3)+(B.1.6)+(C.2.3), (A.4)+(B.1.6)+(C.2.3), (A.1)+(B.1.7)+(C.2.3), (A.2)+(B.1.7)+(C.2.3), (A.3)+(B.1.7)+(C.2.3), (A.4)+(B.1.7)+(C.2.3), (A.1)+(B.1.8)+(C.2.3), (A.2)+(B.1.8)+(C.2.3), (A.3)+(B.1.8)+(C.2.3), (A.4)+(B.1.8)+(C.2.3), (A.1)+(B.1.9)+(C.2.3), (A.2)+(B.1.9)+(C.2.3), (A.3)+(B.1.9)+(C.2.3), (A.4)+(B.1.9)+(C.2.3), (A.1)+(B.1.10)+(C.2.3), (A.2)+(B.1.10)+(C.2.3), (A.3)+(B.1.10)+(C.2.3), (A.4)+(B.1.10)+(C.2.3), (A.1)+(B.1.1)+(C.2.3), (A.2)+(B.1.1))+(C.2.3), (A.3)+(B.1.1))+(C.2.3), (A.4)+(B.1.11)+(C.2.3), (A.1)+(B.1.12)+(C.2.3), (A.2)+(B.1.12)+(C.2.3), (A.3)+(B.1.12)+(C.2.3), (A.4)+(B.1.12)+(C.2.3), (A.1)+(B.1.13)+(C.2.3), (A.2)+(B.1.13)+(C.2.3), (A.3)+(B.1.13)+(C.2.3), (A.4)+(B.1.13)+(C.2.3), (A.1)+(B.1.14)+(C.2.3), (A.2)+(B.1.14)+(C.2.3), (A.3)+(B.1.14)+(C.2.3), (A.4)+(B.1.14)+(C.2.3), (A.1)+(B.1.15)+(C.2.3), (A.2)+(B.1.15)+(C.2.3), (A.3)+(B.1.15)+(C.2.3), (A.4)+(B.1.15)+(C.2.3), (A.1)+(B.1.16)+(C.2.3), (A.2)+(B.1.16)+(C.2.3), (A.3)+(B.1.16)+(C.2.3), (A.4)+(B.1.16)+(C.2.3), (A.1)+(B.1.17)+(C.2.3), (A.2)+(B.1.17)+(C.2.3), (A.3)+(B.1.17)+(C.2.3), (A.4)+(B.1.17)+(C.2.3), (A1.1)+(B.2.1)+(C.2.3), (A.2)+(B.2.1)+(C.2.3), (A.3)+(B.2.1)+(C.2.3), (A.4)+(B.2.1)+(C.2.3), (A.1)+(B.2.2)+(C.2.3), (A.2)+(B.2.2)+(C.2.3), (A.3)+(B.2.2)+(C.2.3), (A.4)+(B.2.2)+(C.2.3), (A.1)+(B.2.3)+(C.2.3), (A.2)+(B.2.3)+(C.2.3), (A.3)+(B.2.3)+(C.2.3), (A.4)+(B.2.3)+(C.2.3), (A.1)+(B.2.4)+(C.2.3), (A.2)+(B.2.4)+(C.2.3), (A.3)+(B.2.4)+(C.2.3), (A.4)+(B.2.4)+(C.2.3), (A.1)+(B.2.5)+(C.2.3), (A.2)+(B.2.5)+(C.2.3), (A.3)+(B.2.5)+(C.2.3), (A.4)+(B.2.5)+(C.2.3), (A.1)+(B.2.6)+(C.2.3), (A.2)+(B.2.6)+(C.2.3), (A.3)+(B.2.6)+(C.2.3), (A.4)+(B.2.6)+(C.2.3), (A.1)+(B.2.7)+(C.2.3), (A.2)+(B.2.7)+(C.2.3), (A.3)+(B.2.7)+(C.2.3), (A.4)+(B.2.7)+(C.2.3), (A.1)+(B.2.8)+(C.2.3), (A.2)+(B.2.8)+(C.2.3), (A.3)+(B.2.8)+(C.2.3), (A.4)+(B.2.8)+(C.2.3).

(A.1)+(B.1.1)+(C.2.31), (A.2)+(B.1.1)+(C.2.31), (A.3)+(B.1.1)+(C.2.31), (A.4)+(B.1.1)+(C.2.31), (A.1)+(B.1.2)+(C.3.1), (A.2)+(B.1.2)+(C.3.1), (A.3)+(B.1.2)+(C.3.1), (A.4)+(B.1.2)+(C.3.1), (A.1)+(B.1.3)+(C.3.1), (A.2)+(B.1.3)+(C.3.1), (A.3)+(B.1.3)+(C.3.1), (A.4)+(B.1.3)+(C.3.1), (A.1)+(B.1.4)+(C.3.1), (A.2)+(B.1.4)+(C.3.1), (A.3)+(B.1.4)+(C.3.1), (A.4)+(B.1.4)+(C.3.1), (A.1)+(B.1.5)+(C.3.1), (A.2)+(B.1.5)+(C.3.1), (A.3)+(B.1.5)+(C.3.1), (A.4)+(B.1.5)+(C.3.1), (A.1)+(B.1.6)+(C.3.1), (A.2)+(B.1.6)+(C.3.1), (A.3)+(B.1.6)+(C.3.1), (A.4)+(B.1.6)+(C.3.1), (A.1)+(B.1.7)+(C.3.1), (A.2)+(B.1.7)+(C.3.1), (A.3)+(B.1.7)+(C.3.1), (A.4)+(B.1.7)+(C.3.1), (A.1)+(B.1.8)+(C.3.1), (A.2)+(B.1.8)+(C.3.1), (A.3)+(B.1.8)+(C.3.1), (A.4)+(B.1.8)+(C.3.1), (A.1)+(B.1.9)+(C.3.1), (A.2)+(B.1.9)+(C.3.1), (A.3)+(B.1.9)+(C.3.1), (A.4)+(B.1.9)+(C.3.1), (A.1)+(B.1.10)+(C.3.1), (A.2)+(B.1.10)+(C.3.1), (A.3)+(B.1.10)+(C.3.1), (A.4)+(B.1.10)+(C.3.1), (A.1)+(B.1.11)+(C.3.1), (A.2)+(B.1.11)+(C.3.1), (A.3)+(B.1.11)+(C.3.1), (A.4)+(B.1.11)+(C.3.1), (A.1)+(B.1.12)+(C.3.1), (A.2)+(B.1.12)+(C.3.1), (A.3)+(B.1.12)+(C.3.1), (A.4)+(B.1.12)+(C.3.1), (A.1)+(B.1.13)+(C.3.1), (A.2)+(B.1.13)+(C.3.1), (A.3)+(B.1.13)+(C.3.1), (A.4)+(B.1.13)+(C.3.1), (A.1)+(B.1.14)+(C.3.1), (A.2)+(B.1.14)+(C.3.1), (A.3)+(B.1.14)+(C.3.1), (A.4)+(B.1.14)+(C.3.1), (A.1)+(B.1.15)+(C.3.1), (A.2)+(B.1.15)+(C.3.1), (A.3)+(B.1.15)+(C.3.1), (A.4)+(B.1.15)+(C.3.1), (A.1)+(B.1.16)+(C.3.1), (A.2)+(B.1.16)+(C.3.1), (A.3)+(B.1.16)+(C.3.1), (A.4)+(B.1.16)+(C.3.1), (A.1)+(B.1.17)+(C.3.1), (A.2)+(B.1.17)+(C.3.1), (A.3)+(B.1.17)+(C.3.1), (A.4)+(B.1.17)+(C.3.1), (A1.1)+(B.2.1)+(C.3.1), (A.2)+(B.2.1)+(C.3.1), (A.3)+(B.2.1)+(C.3.1), (A.4)+(B.2.1)+(C.3.1), (A.1)+(B.2.2)+(C.3.1), (A.2)+(B.2.2)+(C.3.1), (A.3)+(B.2.2)+(C.3.1), (A.4)+(B.2.2)+(C.3.1), (A.1)+(B.2.3)+(C.3.1), (A.2)+(B.2.3)+(C.3.1), (A.3)+(B.2.3)+(C.3.1), (A.4)+(B.2.3)+(C.3.1), (A.1)+(B.2.4)+(C.3.1), (A.2)+(B.2.4)+(C.3.1), (A.3)+(B.2.4)+(C.3.1), (A.4)+(B.2.4)+(C.3.1), (A.1)+(B.2.5)+(C.3.1), (A.2)+(B.2.5)+(C.3.1), (A.3)+(B.2.5)+(C.3.1), (A.4)+(B.2.5)+(C.3.1), (A.1)+(B.2.6)+(C.3.1), (A.2)+(B.2.6)+(C.3.1), (A.3)+(B.2.6)+(C.3.1), (A.4)+(B.2.6)+(C.3.1), (A.1)+(B.2.7)+(C.3.1), (A.2)+(B.2.7)+(C.3.1), (A.3)+(B.2.7)+(C.3.1), (A.4)+(B.2.7)+(C.3.1), (A.1)+(B.2.8)+(C.3.1), (A.2)+(B.2.8)+(C.3.1), (A.3)+(B.2.8)+(C.3.1), (A.4)+(B.2.8)+(C.3.1).

(A.1)+(B.1.1)+(C.3.2), (A.2)+(B.1.1)+(C.3.2), (A.3)+(B.1.1)+(C.3.2), (A.4)+(B.1.1)+(C.3.2), (A.1)+(B.1.2)+

(C.3.2), (A.2)+(B.1.2)+(C.3.2), (A.3)+(B.1.2)+(C.3.2), (A.4)+(B.1.2)+(C.3.2), (A.1)+(B.1.3)+(C.3.2), (A.2)+(B.1.3)+(C.3.2), (A.3)+(B.1.3)+(C.3.2), (A.4)+(B.1.3)+(C.3.2), (A.1)+(B.1.4)+(C.3.2), (A.2)+(B.1.4)+(C.3.2), (A.3)+(B.1.4)+(C.3.2), (A.4)+(B.1.4)+(C.3.2), (A.1)+(B.1.5)+(C.3.2), (A.2)+(B.1.5)+(C.3.2), (A.3)+(B.1.5)+(C.3.2), (A.4)+(B.1.5)+(C.3.2), (A.1)+(B.1.6)+(C.3.2), (A.2)+(B.1.6)+(C.3.2), (A.3)+(B.1.6)+(C.3.2), (A.4)+(B.1.6)+(C.3.2), (A.1)+(B.1.7)+(C.3.2), (A.2)+(B.1.7)+(C.3.2), (A.3)+(B.1.7)+(C.3.2), (A.4)+(B.1.7)+(C.3.2), (A.1)+(B.1.8)+(C.3.2), (A.2)+(B.1.8)+(C.3.2), (A.3)+(B.1.8)+(C.3.2), (A.4)+(B.1.8)+(C.3.2), (A.1)+(B.1.9)+(C.3.2), (A.2)+(B.1.9)+(C.3.2), (A.3)+(B.1.9)+(C.3.2), (A.4)+(B.1.9)+(C.3.2), (A.1)+(B.1.10)+(C.3.2), (A.2)+(B.1.10)+(C.3.2), (A.3)+(B.1.10)+(C.3.2), (A.4)+(B.1.10)+(C.3.2), (A.1)+(B.1.11)+(C.3.2), (A.2)+(B.1.11)+(C.3.2), (A.3)+(B.1.11)+(C.3.2), (A.4)+(B.1.11)+(C.3.2), (A.1)+(B.1.12)+(C.3.2), (A.2)+(B.1.12)+(C.3.2), (A.3)+(B.1.12)+(C.3.2), (A.4)+(B.1.12)+(C.3.2), (A.1)+(B.1.13)+(C.3.2), (A.2)+(B.1.13)+(C.3.2), (A.3)+(B.1.13)+(C.3.2), (A.4)+(B.1.13)+(C.3.2), (A.1)+(B.1.14)+(C.3.2), (A.2)+(B.1.14)+(C.3.2), (A.3)+(B.1.14)+(C.3.2), (A.4)+(B.1.14)+(C.3.2), (A.1)+(B.1.15)+(C.3.2), (A.2)+(B.1.15)+(C.3.2), (A.3)+(B.1.15)+(C.3.2), (A.4)+(B.1.15)+(C.3.2), (A.1)+(B.1.16)+(C.3.2), (A.2)+(B.1.16)+(C.3.2), (A.3)+(B.1.16)+(C.3.2), (A.4)+(B.1.16)+(C.3.2), (A.1)+(B.1.17)+(C.3.2), (A.2)+(B.1.17)+(C.3.2), (A.3)+(B.1.17)+(C.3.2), (A.4)+(B.1.17)+(C.3.2), (A.1)+(B.2.1)+(C.3.2), (0.2)+(B.2.1)+(C.3.2), (A.3)+(B.2.1)+(C.3.2), (A.4)+(B.2.1)+(C.3.2), (A.1)+(B.2.2)+(C.3.2), (A.2)+(B.2.2)+(C.3.2), (A.3)+(B.2.2)+(C.3.2), (A.4)+(B.2.2)+(C.3.2), (A.1)+(B.2.3)+(C.3.2), (A.2)+(B.2.3)+(C.3.2), (A.3)+(B.2.3)+(C.3.2), (A.4)+(B.2.3)+(C.3.2), (A.1)+(B.2.4)+(C.3.2), (A.2)+(B.2.4)+(C.3.2), (A.3)+(B.2.4)+(C.3.2), (A.4)+(B.2.4)+(C.3.2), (A.1)+(B.2.5)+(C.3.2), (A.2)+(B.2.5)+(C.3.2), (A.3)+(B.2.5)+(C.3.2), (A.4)+(B.2.5)+(C.3.2), (A.1)+(B.2.6)+(C.3.2), (A.2)+(B.2.6)+(C.3.2), (A.3)+(B.2.6)+(C.3.2), (A.4)+(B.2.6)+(C.3.2), (A.1)+(B.2.7)+(C.3.2), (A.2)+(B.2.7)+(C.3.2), (A.3)+(B.2.7)+(C.3.2), (A.4)+(B.2.7)+(C.3.2), (A.1)+(B.2.8)+(C.3.2), (A.2)+(B.2.8)+(C.3.2), (A.3)+(B.2.8)+(C.3.2), (A.4)+(B.2.8)+(C.3.2).

(A.1)+(B.1.1)+(C.3.3), (A.2)+(B.1.1)+(C.3.3), (A.3)+(B.1.1)+(C.3.3), (A.4)+(B.1.1)+(C.3.3), (A.1)+(B.1.2)+(C.3.3), (A.2)+(B.1.2)+(C.3.3), (A.3)+(B.1.2)+(C.3.3), (A.4)+(B.1.2)+(C.3.3), (A.1)+(B.1.3)+(C.3.3), (A.2)+(B.1.3)+(C.3.3), (A.3)+(B.1.3)+(C.3.3), (A.4)+(B.1.3)+(C.3.3), (A.1)+(B.1.4)+(C.3.3), (A.2)+(B.1.4)+(C.3.3), (A.3)+(B.1.4)+(C.3.3), (A.4)+(B.1.4)+(C.3.3), (A.1)+(B.1.5)+(C.3.3), (A.2)+(B.1.5)+(C.3.3), (A.3)+(B.1.5)+(C.3.3), (A.4)+(B.1.5)+(C.3.3), (A.1)+(B.1.6)+(C.3.3), (A.2)+(B.1.6)+(C.3.3), (A.3)+(B.1.6)+(C.3.3), (A.4)+(B.1.6)+(C.3.3), (A.1)+(B.1.7)+(C.3.3), (A.2)+(B.1.7)+(C.3.3), (A.3)+(B.1.7)+(C.3.3), (A.4)+(B.1.7)+(C.3.3), (A.1)+(B.1.8)+(C.3.3), (A.2)+(B.1.8)+(C.3.3), (A.3)+(B.1.8)+(C.3.3), (A.4)+(B.1.8)+(C.3.3), (A.1)+(B.1.9)+(C.3.3), (A.2)+(B.1.9)+(C.3.3), (A.3)+(B.1.9)+(C.3.3), (A.4)+(B.1.9)+(C.3.3), (A.1)+(B.1.10)+(C.3.3), (A.2)+(B.1.10)+(C.3.3), (A.3)+(B.1.10)+(C.3.3), (A.4)+(B.1.10)+(C.3.3), (A.1)+(B.1.11)+(C.3.3), (A.2)+(B.1.11)+(C.3.3), (A.3)+(B.1.11)+(C.3.3), (A.4)+(B.1.11)+(C.3.3), (A.1)+(B.1.12)+(C.3.3), (A.2)+(B.1.12)+(C.3.3), (A.3)+(B.1.12)+(C.3.3), (A.4)+(B.1.12)+(C.3.3), (A.1)+(B.1.13)+(C.3.3), (A.2)+(B.1.13)+(C.3.3), (A.3)+(B.1.13)+(C.3.3), (A.4)+(B.1.13)+(C.3.3), (A.1)+(B.1.14)+(C.3.3), (A.2)+(B.1.14)+(C.3.3), (A.3)+(B.1.14)+(C.3.3), (A.4)+(B.1.14)+(C.3.3), (A.1)+(B.1.15)+(C.3.3), (A.2)+(B.1.15)+(C.3.3), (A.3)+(B.1.15)+(C.3.3), (A.4)+(B.1.15)+(C.3.3), (A.1)+(B.1.16)+(C.3.3), (A.2)+(B.1.16)+(C.3.3), (A.3)+(B.1.16)+(C.3.3), (A.4)+(B.1.16)+(C.3.3), (A.1)+(B.1.17)+(C.3.3), (A.2)+(B.1.17)+(C.3.3), (A.3)+(B.1.17)+(C.3.3), (A.4)+(B.1.17)+(C.3.3), (A1.1)+(B.2.1)+(C.3.3), (A.2)+(B.2.1)+(C.3.3), (A.3)+(B.2.1)+(C.3.3), (A.4)+(B.2.1)+(C.3.3), (A.1)+(B.2.2)+(C.3.3), (A.2)+(B.2.2)+(C.3.3), (A.3)+(B.2.2)+(C.3.3), (A.4)+(B.2.2)+(C.3.3), (A.1)+(B.2.3)+(C.3.3), (A.2)+(B.2.3)+(C.3.3), (A.3)+(B.2.3)+(C.3.3), (A.4)+(B.2.3)+(C.3.3), (A.1)+(B.2.4)+(C.3.3), (A.2)+(B.2.4)+(C.3.3), (A.3)+(B.2.4)+(C.3.3), (A.4)+(B.2.4)+(C.3.3), (A.1)+(B.2.5)+(C.3.3), (A.2)+(B.2.5)+(C.3.3), (A.3)+(B.2.5)+(C.3.3), (A.4)+(B.2.5)+(C.3.3), (A.1)+(B.2.6)+(C.3.3), (A.2)+(B.2.6)+(C.3.3), (A.3)+(B.2.6)+(C.3.3), (A.4)+(B.2.6)+(C.3.3), (A.1)+(B.2.7)+(C.3.3), (A.2)+(B.2.7)+(C.3.3), (A.3)+(B.2.7)+(C.3.3), (A.4)+(B.2.7)+(C.3.3), (A.1)+(B.2.8)+(C.3.3), (A.2)+(B.2.8)+(C.3.3), (A.3)+(B.2.8)+(C.3.3), (A.4)+(B.2.8)+(C.3.3).

(A.1)+(B.1.1)+(C.3.4), (A.2)+(B.1.1)+(C.3.4), (A.3)+(B.1.1)+(C.3.4), (A.4)+(B.1.1)+(C.3.4), (A.1)+(B.1.2)+(C.3.4), (A.2)+(B.1.2)+(C.3.4), (A.3)+(B.1.2)+(C.3.4), (A.4)+(B.1.2)+(C.3.4), (A.1)+(B.1.3)+(C.3.4), (A.2)+(B.1.3)+(C.3.4), (A.3)+(B.1.3)+(C.3.4), (A.4)+(B.1.3)+(C.3.4), (A.1)+(B.1.4)+(C.3.4), (A.2)+(B.1.4)+(C.3.4), (A.3)+(B.1.4)+(C.3.4), (A.4)+(B.1.4)+(C.3.4), (A.1)+(B.1.5)+(C.3.4), (A.2)+(B.1.5)+(C.3.4), (A.3)+(B.1.5)+(C.3.4), (A.4)+(B.1.5)+(C.3.4), (A.1)+(B.1.6)+(C.3.4), (A.2)+(B.1.6)+(C.3.4), (A.3)+(B.1.6)+(C.3.4), (A.4)+(B.1.6)+(C.3.4), (A.1)+(B.1.7)+(C.3.4), (A.2)+(B.1.7)+(C.3.4), (A.3)+(B.1.7)+(C.3.4), (A.4)+(B.1.7)+(C.3.4), (A.1)+(B.1.8)+(C.3.4), (A.2)+(B.1.8)+(C.3.4), (A.3)+(B.1.8)+(C.3.4), (A.4)+(B.1.8)+(C.3.4), (A.1)+(B.1.9)+(C.3.4), (A.2)+(B.1.9)+(C.3.4), (A.3)+(B.1.9)+(C.3.4), (A.4)+(B.1.9)+(C.3.4), (A.1)+(B.1.10)+(C.3.4), (A.2)+(B.1.10)+(C.3.4), (A.3)+(B.1.10)+(C.3.4), (A.4)+(B.1.10)+(C.3.4), (A.1)+(B.1.1)+(C.3.4), (A.2)+(B.1.1))+(C.3.4), (A.3)+(B.1.1))+(C.3.4), (A.4)+(B.1.11)+(C.3.4), (A.1)+(B.1.12)+(C.3.4), (A.2)+(B.1.12)+(C.3.4), (A.3)+(B.1.12)+(C.3.4), (A.4)+(B.1.12)+(C.3.4), (A.1)+(B.1.13)+(C.3.4), (A.2)+(B.1.13)+(C.3.4), (A.3)+(B.1.13)+(C.3.4), (A.4)+(B.1.13)+(C.3.4), (A.1)+(B.1.14)+(C.3.4), (A.2)+(B.1.14)+(C.3.4), (A.3)+(B.1.14)+(C.3.4), (A.4)+(B.1.14)+(C.3.4), (A.1)+(B.1.15)+(C.3.4), (A.2)+(B.1.15)+(C.3.4), (A.3)+(B.1.15)+(C.3.4), (A.4)+(B.1.15)+(C.3.4), (A.1)+(B.1.16)+(C.3.4), (A.2)+(B.1.16)+(C.3.4), (A.3)+(B.1.16)+(C.3.4), (A.4)+(B.1.16)+(C.3.4), (A.1)+(B.1.17)+(C.3.4), (A.2)+(B.1.17)+(C.3.4), (A.3)+(B.1.17)+(C.3.4), (A.4)+(B.1.17)+(C.3.4), (A.1)+(B.2.1)+(C.3.4), (A.2)+(B.2.1)+(C.3.4), (A.3)+(B.2.1)+(C.3.4), (A.4)+(B.2.1)+(C.3.4), (A.1)+(B.2.2)+(C.3.4), (A.2)+(B.2.2)+(C.3.4), (A.3)+(B.2.2)+(C.3.4), (A.4)+(B.2.2)+(C.3.4), (A.1)+(B.2.3)+(C.3.4), (A.2)+(B.2.3)+(C.3.4), (A.3)+(B.2.3)+(C.3.4), (A.4)+(B.2.3)+(C.3.4), (A.1)+(B.2.4)+(C.3.4), (A.2)+(B.2.4)+(C.3.4), (A.3)+(B.2.4)+(C.3.4), (A.4)+(B.2.4)+(C.3.4), (A.1)+(B.2.5)+(C.3.4), (A.2)+(B.2.5)+(C.3.4), (A.3)+(B.2.5)+(C.3.4), (A.4)+(B.2.5)+(C.3.4), (A.1)+(B.2.6)+(C.3.4), (A.2)+(B.2.6)+(C.3.4), (A.3)+(B.2.6)+(C.3.4), (A.4)+(B.2.6)+(C.3.4), (A.1)+(B.2.7)+(C.3.4), (A.2)+(B.2.7)+(C.3.4), (A.3)+(B.2.7)+(C.3.4), (A.4)+(B.2.7)+(C.3.4), (A.1)+(B.2.8)+(C.3.4), (A.2)+(B.2.8)+(C.3.4), (A.3)+(B.2.8)+(C.3.4), (A.4)+(B.2.8)+(C.3.4).

(A.1)+(B.1.1)+(C.3.5), (A.2)+(B.1.1)+(C.3.5), (A.3)+(B.1.1)+(C.3.5), (A.4)+(B.1.1)+(C.3.5), (A.1)+(B.1.2)+(C.3.5), (A.2)+(B.1.2)+(C.3.5), (A.3)+(B.1.2)+(C.3.5), (A.4)+(B.1.2)+(C.3.5), (A.1)+(B.1.3)+(C.3.5), (A.2)+

(B.1.3)+(C.3.5), (A.3)+(B.1.3)+(C.3.5), (A.4)+(B.1.3)+(C.3.5), (A.1)+(B.1.4)+(C.3.5), (A.2)+(B.1.4)+(C.3.5), (A.3)+(B.1.4)+(C.3.5), (A.4)+(B.1.4)+(C.3.5), (A.1)+(B.1.5)+(C.3.5), (A.2)+(B.1.5)+(C.3.5), (A.3)+(B.1.5)+(C.3.5), (A.4)+(B.1.5)+(C.3.5), (A.1)+(B.1.6)+(C.3.5), (A.2)+(B.1.6)+(C.3.5), (A.3)+(B.1.6)+(C.3.5), (A.4)+(B.1.6)+(C.3.5), (A.1)+(B.1.7)+(C.3.5), (A.2)+(B.1.7)+(C.3.5), (A.3)+(B.1.7)+(C.3.5), (A.4)+(B.1.7)+(C.3.5), (A.1)+(B.1.8)+(C.3.5), (A.2)+(B.1.8)+(C.3.5), (A.3)+(B.1.8)+(C.3.5), (A.4)+(B.1.8)+(C.3.5), (A.1)+(B.1.9)+(C.3.5), (A.2)+(B.1.9)+(C.3.5), (A.3)+(B.1.9)+(C.3.5), (A.4)+(B.1.9)+(C.3.5), (A.1)+(B.1.10)+(C.3.5), (A.2)+(B.1.10)+(C.3.5), (A.3)+(B.1.10)+(C.3.5), (A.4)+(B.1.10)+(C.3.5), (A.1)+(B.1.1)+(C.3.5), (A.2)+(B.1.1))+(C.3.5), (A.3)+(B.1.1))+(C.3.5), (A.4)+(B.1.11)+(C.3.5), (A.1)+(B.1.12)+(C.3.5), (A.2)+(B.1.12)+(C.3.5), (A.3)+(B.1.12)+(C.3.5), (A.4)+(B.1.12)+(C.3.5), (A.1)+(B.1.13)+(C.3.5), (A.2)+(B.1.13)+(C.3.5), (A.3)+(B.1.13)+(C.3.5), (A.4)+(B.1.13)+(C.3.5), (A.1)+(B.1.14)+(C.3.5), (A.2)+(B.1.14)+(C.3.5), (A.3)+(B.1.14)+(C.3.5), (A.4)+(B.1.14)+(C.3.5), (A.1)+(B.1.15)+(C.3.5), (A.2)+(B.1.15)+(C.3.5), (A.3)+(B.1.15)+(C.3.5), (A.4)+(B.1.15)+(C.3.5), (A.1)+(B.1.16)+(C.3.5), (A.2)+(B.1.16)+(C.3.5), (A.3)+(B.1.16)+(C.3.5), (A.4)+(B.1.16)+(C.3.5), (A.1)+(B.1.17)+(C.3.5), (A.2)+(B.1.17)+(C.3.5), (A.3)+(B.1.17)+(C.3.5), (A.4)+(B.1.17)+(C.3.5),
(A.1)+(B.2.1)+(C.3.5), (A.2)+(B.2.1)+(C.3.5), (A.3)+(B.2.1)+(C.3.5), (A.4)+(B.2.1)+(C.3.5), (A.1)+(B.2.2)+(C.3.5), (A.2)+(B.2.2)+(C.3.5), (A.3)+(B.2.2)+(C.3.5), (A.4)+(B.2.2)+(C.3.5), (A.1)+(B.2.3)+(C.3.5), (A.2)+(B.2.3)+(C.3.5), (A.3)+(B.2.3)+(C.3.5), (A.4)+(B.2.3)+(C.3.5), (A.1)+(B.2.4)+(C.3.5), (A.2)+(B.2.4)+(C.3.5), (A.3)+(B.2.4)+(C.3.5), (A.4)+(B.2.4)+(C.3.5), (A.1)+(B.2.5)+(C.3.5), (A.2)+(B.2.5)+(C.3.5), (A.3)+(B.2.5)+(C.3.5), (A.4)+(B.2.5)+(C.3.5), (A.1)+(B.2.6)+(C.3.5), (A.2)+(B.2.6)+(C.3.5), (A.3)+(B.2.6)+(C.3.5), (A.4)+(B.2.6)+(C.3.5), (A.1)+(B.2.7)+(C.3.5), (A.2)+(B.2.7)+(C.3.5), (A.3)+(B.2.7)+(C.3.5), (A.4)+(B.2.7)+(C.3.5), (A.1)+(B.2.8)+(C.3.5), (A.2)+(B.2.8)+(C.3.5), (A.3)+(B.2.8)+(C.3.5), (A.4)+(B.2.8)+(C.3.5).

(A.1)+(B.1.1)+(C.3.6), (A.2)+(B.1.1)+(C.3.6), (A.3)+(B.1.1)+(C.3.6), (A.4)+(B.1.1)+(C.3.6), (A.1)+(B.1.2)+(C.3.6), (A.2)+(B.1.2)+(C.3.6), (A.3)+(B.1.2)+(C.3.6), (A.4)+(B.1.2)+(C.3.6), (A.1)+(B.1.3)+(C.3.6), (A.2)+(B.1.3)+(C.3.6), (A.3)+(B.1.3)+(C.3.6), (A.4)+(B.1.3)+(C.3.6), (A.1)+(B.1.4)+(C.3.6), (A.2)+(B.1.4)+(C.3.6), (A.3)+(B.1.4)+(C.3.6), (A.4)+(B.1.4)+(C.3.6), (A.1)+(B.1.5)+(C.3.6), (A.2)+(B.1.5)+(C.3.6), (A.3)+(B.1.5)+(C.3.6), (A.4)+(B.1.5)+(C.3.6), (A.1)+(B.1.6)+(C.3.6), (A.2)+(B.1.6)+(C.3.6), (A.3)+(B.1.6)+(C.3.6), (A.4)+(B.1.6)+(C.3.6), (A.1)+(B.1.7)+(C.3.6), (A.2)+(B.1.7)+(C.3.6), (A.3)+(B.1.7)+(C.3.6), (A.4)+(B.1.7)+(C.3.6), (A.1)+(B.1.8)+(C.3.6), (A.2)+(B.1.8)+(C.3.6), (A.3)+(B.1.8)+(C.3.6), (A.4)+(B.1.8)+(C.3.6), (A.1)+(B.1.9)+(C.3.6), (A.2)+(B.1.9)+(C.3.6), (A.3)+(B.1.9)+(C.3.6), (A.4)+(B.1.9)+(C.3.6), (A.1)+(B.1.10)+(C.3.6), (A.2)+(B.1.10)+(C.3.6), (A.3)+(B.1.10)+(C.3.6), (A.4)+(B.1.10)+(C.3.6), (A.1)+(B.1.11)+(C.3.6), (A.2)+(B.1.11)+(C.3.6), (A.3)+(B.1.11))+(C.3.6), (A.4)+(B.1.11)+(C.3.6), (A.1)+(B.1.12)+(C.3.6), (A.2)+(B.1.12)+(C.3.6), (A.3)+(B.1.12)+(C.3.6), (A.4)+(B.1.12)+(C.3.6), (A.1)+(B.1.13)+(C.3.6), (A.2)+(B.1.13)+(C.3.6), (A.3)+(B.1.13)+(C.3.6), (A.4)+(B.1.13)+(C.3.6), (A.1)+(B.1.14)+(C.3.6), (A.2)+(B.1.14)+(C.3.6), (A.3)+(B.1.14)+(C.3.6), (A.4)+(B.1.14)+(C.3.6), (A.1)+(B.1.15)+(C.3.6), (A.2)+(B.1.15)+(C.3.6), (A.3)+(B.1.15)+(C.3.6), (A.4)+(B.1.15)+(C.3.6), (A.1)+(B.1.16)+(C.3.6), (A.2)+(B.1.16)+(C.3.6), (A.3)+(B.1.16)+(C.3.6), (A.4)+(B.1.16)+(C.3.6), (A.1)+(B.1.17)+(C.3.6), (A.2)+(B.1.17)+(C.3.6), (A.3)+(B.1.17)+(C.3.6), (A.4)+(B.1.17)+(C.3.6),
(A.1)+(B.2.1)+(C.3.6), (A.2)+(B.2.1)+(C.3.6), (A.3)+(B.2.1)+(C.3.6), (A.4)+(B.2.1)+(C.3.6), (A.1)+(B.2.2)+(C.3.6), (A.2)+(B.2.2)+(C.3.6), (A.3)+(B.2.2)+(C.3.6), (A.4)+(B.2.2)+(C.3.6), (A.1)+(B.2.3)+(C.3.6), (A.2)+(B.2.3)+(C.3.6), (A.3)+(B.2.3)+(C.3.6), (A.4)+(B.2.3)+(C.3.6), (A.1)+(B.2.4)+(C.3.6), (A.2)+(B.2.4)+(C.3.6), (A.3)+(B.2.4)+(C.3.6), (A.4)+(B.2.4)+(C.3.6), (A.1)+(B.2.5)+(C.3.6), (A.2)+(B.2.5)+(C.3.6), (A.3)+(B.2.5)+(C.3.6), (A.4)+(B.2.5)+(C.3.6), (A.1)+(B.2.6)+(C.3.6), (A.2)+(B.2.6)+(C.3.6), (A.3)+(B.2.6)+(C.3.6), (A.4)+(B.2.6)+(C.3.6), (A.1)+(B.2.7)+(C.3.6), (A.2)+(B.2.7)+(C.3.6), (A.3)+(B.2.7)+(C.3.6), (A.4)+(B.2.7)+(C.3.6), (A.1)+(B.2.8)+(C.3.6), (A.2)+(B.2.8)+(C.3.6), (A.3)+(B.2.8)+(C.3.6), (A.4)+(B.2.8)+(C.3.6).

(A.1)+(B.1.1)+(C.3.7), (A.2)+(B.1.1)+(C.3.7), (A.3)+(B.1.1)+(C.3.7), (A.4)+(B.1.1)+(C.3.7), (A.1)+(B.1.2)+(C.3.7), (A.2)+(B.1.2)+(C.3.7), (A.3)+(B.1.2)+(C.3.7), (A.4)+(B.1.2)+(C.3.7), (A.1)+(B.1.3)+(C.3.7), (A.2)+(B.1.3)+(C.3.7), (A.3)+(B.1.3)+(C.3.7), (A.4)+(B.1.3)+(C.3.7), (A.1)+(B.1.4)+(C.3.7), (A.2)+(B.1.4)+(C.3.7), (A.3)+(B.1.4)+(C.3.7), (A.4)+(B.1.4)+(C.3.7), (A.1)+(B.1.5)+(C.3.7), (A.2)+(B.1.5)+(C.3.7), (A.3)+(B.1.5)+(C.3.7), (A.4)+(B.1.5)+(C.3.7), (A.1)+(B.1.6)+(C.3.7), (A.2)+(B.1.6)+(C.3.7), (A.3)+(B.1.6)+(C.3.7), (A.4)+(B.1.6)+(C.3.7), (A.1)+(B.1.7)+(C.3.7), (A.2)+(B.1.7)+(C.3.7), (A.3)+(B.1.7)+(C.3.7), (A.4)+(B.1.7)+(C.3.7), (A.1)+(B.1.8)+(C.3.7), (A.2)+(B.1.8)+(C.3.7), (A.3)+(B.1.8)+(C.3.7), (A.4)+(B.1.8)+(C.3.7), (A.1)+(B.1.9)+(C.3.7), (A.2)+(B.1.9)+(C.3.7), (A.3)+(B.1.9)+(C.3.7), (A.4)+(B.1.9)+(C.3.7), (A.1)+(B.1.10)+(C.3.7), (A.2)+(B.1.10)+(C.3.7), (A.3)+(B.1.10)+(C.3.7), (A.4)+(B.1.10)+(C.3.7), (A.1)+(B.1.1)+(C.3.7), (A.2)+(B.1.1)+(C.3.7), (A.3)+(B.1.1))+(C.3.7), (A.4)+(B.1.11)+(C.3.7), (A.1)+(B.1.12)+(C.3.7), (A.2)+(B.1.12)+(C.3.7), (A.3)+(B.1.12)+(C.3.7), (A.4)+(B.1.12)+(C.3.7), (A.1)+(B.1.13)+(C.3.7), (A.2)+(B.1.13)+(C.3.7), (A.3)+(B.1.13)+(C.3.7), (A.4)+(B.1.13)+(C.3.7), (A.1)+(B.1.14)+(C.3.7), (A.2)+(B.1.14)+(C.3.7), (A.3)+(B.1.14)+(C.3.7), (A.4)+(B.1.14)+(C.3.7), (A.1)+(B.1.15)+(C.3.7), (A.2)+(B.1.15)+(C.3.7), (A.3)+(B.1.15)+(C.3.7), (A.4)+(B.1.15)+(C.3.7), (A.1)+(B.1.16)+(C.3.7), (A.2)+(B.1.16)+(C.3.7), (A.3)+(B.1.16)+(C.3.7), (A.4)+(B.1.16)+(C.3.7), (A.1)+(B.1.17)+(C.3.7), (A.2)+(B.1.17)+(C.3.7), (A.3)+(B.1.17)+(C.3.7), (A.4)+(B.1.17)+(C.3.7),
(A1.1)+(B.2.1)+(C.3.7), (A.2)+(B.2.1)+(C.3.7), (A.3)+(B.2.1)+(C.3.7), (A.4)+(B.2.1)+(C.3.7), (A.1)+(B.2.2)+(C.3.7), (A.2)+(B.2.2)+(C.3.7), (A.3)+(B.2.2)+(C.3.7), (A.4)+(B.2.2)+(C.3.7), (A.1)+(B.2.3)+(C.3.7), (A.2)+(B.2.3)+(C.3.7), (A.3)+(B.2.3)+(C.3.7), (A.4)+(B.2.3)+(C.3.7), (A.1)+(B.2.4)+(C.3.7), (A.2)+(B.2.4)+(C.3.7), (A.3)+(B.2.4)+(C.3.7), (A.4)+(B.2.4)+(C.3.7), (A.1)+(B.2.5)+(C.3.7), (A.2)+(B.2.5)+(C.3.7), (A.3)+(B.2.5)+(C.3.7), (A.4)+(B.2.5)+(C.3.7), (A.1)+(B.2.6)+(C.3.7), (A.2)+(B.2.6)+(C.3.7), (A.3)+(B.2.6)+(C.3.7), (A.4)+(B.2.6)+(C.3.7), (A.1)+(B.2.7)+(C.3.7), (A.2)+(B.2.7)+(C.3.7), (A.3)+(B.2.7)+(C.3.7), (A.4)+(B.2.7)+(C.3.7), (A.1)+(B.2.8)+(C.3.7), (A.2)+(B.2.8)+(C.3.7), (A.3)+(B.2.8)+(C.3.7), (A.4)+(B.2.8)+(C.3.7).

(A.1)+(B.1.1)+(C.3.8), (A.2)+(B.1.1)+(C.3.8), (A.3)+(B.1.1)+(C.3.8), (A.4)+(B.1.1)+(C.3.8), (A.1)+(B.1.2)+(C.3.8), (A.2)+(B.1.2)+(C.3.8), (A.3)+(B.1.2)+(C.3.8), (A.4)+(B.1.2)+(C.3.8), (A.1)+(B.1.3)+(C.3.8), (A.2)+(B.1.3)+(C.3.8), (A.3)+(B.1.3)+(C.3.8), (A.4)+(B.1.3)+(C.3.8), (A.1)+(B.1.4)+(C.3.8), (A.2)+(B.1.4)+(C.3.8), (A.3)+(B.1.4)+(C.3.8), (A.4)+(B.1.4)+(C.3.8), (A.1)+(B.1.5)+(C.3.8), (A.2)+(B.1.5)+(C.3.8), (A.3)+(B.1.5)+(C.3.8), (A.4)+(B.1.5)+(C.3.8), (A.1)+(B.1.6)+(C.3.8), (A.2)+(B.1.6)+(C.3.8), (A.3)+(B.1.6)+(C.3.8), (A.4)+(B.1.6)+(C.3.8), (A.1)+(B.1.7)+(C.3.8), (A.2)+(B.1.7)+(C.3.8), (A.3)+(B.1.7)+(C.3.8), (A.4)+(B.1.7)+(C.3.8), (A.1)+(B.1.8)+(C.3.8), (A.2)+(B.1.8)+(C.3.8), (A.3)+(B.1.8)+(C.3.8), (A.4)+(B.1.8)+(C.3.8), (A.1)+(B.1.9)+(C.3.8), (A.2)+(B.1.9)+(C.3.8), (A.3)+(B.1.9)+(C.3.8), (A.4)+(B.1.9)+(C.3.8), (A.1)+(B.1.10)+(C.3.8), (A.2)+(B.1.10)+(C.3.8), (A.3)+(B.1.10)+(C.3.8), (A.4)+(B.1.10)+(C.3.8), (A.1)+(B.1.11)+(C.3.8), (A.2)+(B.1.11)+(C.3.8), (A.3)+(B.1.11)+(C.3.8), (A.4)+(B.1.11)+(C.3.8), (A.1)+(B.1.12)+(C.3.8), (A.2)+(B.1.12)+(C.3.8), (A.3)+(B.1.12)+(C.3.8), (A.4)+(B.1.12)+(C.3.8), (A.1)+(B.1.13)+(C.3.8), (A.2)+(B.1.13)+(C.3.8), (A.3)+(B.1.13)+(C.3.8), (A.4)+(B.1.13)+(C.3.8), (A.1)+(B.1.14)+(C.3.8), (A.2)+(B.1.14)+(C.3.8), (A.3)+(B.1.14)+(C.3.8), (A.4)+(B.1.14)+(C.3.8), (A.1)+(B.1.15)+(C.3.8), (A.2)+(B.1.15)+(C.3.8), (A.3)+(B.1.15)+(C.3.8), (A.4)+(B.1.15)+(C.3.8), (A.1)+(B.1.16)+(C.3.8), (A.2)+(B.1.16)+(C.3.8), (A.3)+(B.1.16)+(C.3.8), (A.4)+(B.1.16)+(C.3.8), (A.1)+(B.1.17)+(C.3.8), (A.2)+(B.1.17)+(C.3.8), (A.3)+(B.1.17)+(C.3.8), (A.4)+(B.1.17)+(C.3.8), (A.1)+(B.2.1)+(C.3.8), (A.2)+(B.2.1)+(C.3.8), (A.3)+(B.2.1)+(C.3.8), (A.4)+(B.2.1)+(C.3.8), (A.1)+(B.2.2)+(C.3.8), (A.2)+(B.2.2)+(C.3.8), (A.3)+(B.2.2)+(C.3.8), (A.4)+(B.2.2)+(C.3.8), (A.1)+(B.2.3)+(C.3.8), (A.2)+(B.2.3)+(C.3.8), (A.3)+(B.2.3)+(C.3.8), (A.4)+(B.2.3)+(C.3.8), (A.1)+(B.2.4)+(C.3.8), (A.2)+(B.2.4)+(C.3.8), (A.3)+(B.2.4)+(C.3.8), (A.4)+(B.2.4)+(C.3.8), (A.1)+(B.2.5)+(C.3.8), (A.2)+(B.2.5)+(C.3.8), (A.3)+(B.2.5)+(C.3.8), (A.4)+(B.2.5)+(C.3.8), (A.1)+(B.2.6)+(C.3.8), (A.2)+(B.2.6)+(C.3.8), (A.3)+(B.2.6)+(C.3.8), (A.4)+(B.2.6)+(C.3.8), (A.1)+(B.2.7)+(C.3.8), (A.2)+(B.2.7)+(C.3.8), (A.3)+(B.2.7)+(C.3.8), (A.4)+(B.2.7)+(C.3.8), (A.1)+(B.2.8)+(C.3.8), (A.2)+(B.2.8)+(C.3.8), (A.3)+(B.2.8)+(C.3.8), (A.4)+(B.2.8)+(C.3.8).

(A.1)+(B.1.1)+(C.3.9), (A.2)+(B.1.1)+(C.3.9), (A.3)+(B.1.1)+(C.3.9), (A.4)+(B.1.1)+(C.3.9), (A.1)+(B.1.2)+(C.3.9), (A.2)+(B.1.2)+(C.3.9), (A.3)+(B.1.2)+(C.3.9), (A.4)+(B.1.2)+(C.3.9), (A.1)+(B.1.3)+(C.3.9), (A.2)+(B.1.3)+(C.3.9), (A.3)+(B.1.3)+(C.3.9), (A.4)+(B.1.3)+(C.3.9), (A.1)+(B.1.4)+(C.3.9), (A.2)+(B.1.4)+(C.3.9), (A.3)+(B.1.4)+(C.3.9), (A.4)+(B.1.4)+(C.3.9), (A.1)+(B.1.5)+(C.3.9), (A.2)+(B.1.5)+(C.3.9), (A.3)+(B.1.5)+(C.3.9), (A.4)+(B.1.5)+(C.3.9), (A.1)+(B.1.6)+(C.3.9), (A.2)+(B.1.6)+(C.3.9), (A.3)+(B.1.6)+(C.3.9), (A.4)+(B.1.6)+(C.3.9), (A.1)+(B.1.7)+(C.3.9), (A.2)+(B.1.7)+(C.3.9), (A.3)+(B.1.7)+(C.3.9), (A.4)+(B.1.7)+(C.3.9), (A.1)+(B.1.8)+(C.3.9), (A.2)+(B.1.8)+(C.3.9), (A.3)+(B.1.8)+(C.3.9), (A.4)+(B.1.8)+(C.3.9), (A.1)+(B.1.9)+(C.3.9), (A.2)+(B.1.9)+(C.3.9), (A.3)+(B.1.9)+(C.3.9), (A.4)+(B.1.9)+(C.3.9), (A.1)+(B.1.10)+(C.3.9), (A.2)+(B.1.10)+(C.3.9), (A.3)+(B.1.10)+(C.3.9), (A.4)+(B.1.10)+(C.3.9), (A.1)+(B.1.1)+(C.3.9), (A.2)+(B.1.1))+(C.3.9), (A.3)+(B.1.1))+(C.3.9), (A.4)+(B.1.11)+(C.3.9), (A.1)+(B.1.12)+(C.3.9), (A.2)+(B.1.12)+(C.3.9), (A.3)+(B.1.12)+(C.3.9), (A.4)+(B.1.12)+(C.3.9), (A.1)+(B.1.13)+(C.3.9), (A.2)+(B.1.13)+(C.3.9), (A.3)+(B.1.13)+(C.3.9), (A.4)+(B.1.13)+(C.3.9), (A.1)+(B.1.14)+(C.3.9), (A.2)+(B.1.14)+(C.3.9), (A.3)+(B.1.14)+(C.3.9), (A.4)+(B.1.14)+(C.3.9), (A.1)+(B.1.15)+(C.3.9), (A.2)+(B.1.15)+(C.3.9), (A.3)+(B.1.15)+(C.3.9), (A.4)+(B.1.15)+(C.3.9), (A.1)+(B.1.16)+(C.3.9), (A.2)+(B.1.16)+(C.3.9), (A.3)+(B.1.16)+(C.3.9), (A.4)+(B.1.16)+(C.3.9), (A.1)+(B.1.17)+(C.3.9), (A.2)+(B.1.17)+(C.3.9), (A.3)+(B.1.17)+(C.3.9), (A.4)+(B.1.17)+(C.3.9), (A.1)+(B.2.1)+(C.3.9), (A.2)+(B.2.1)+(C.3.9), (A.3)+(B.2.1)+(C.3.9), (A.4)+(B.2.1)+(C.3.9), (A.1)+(B.2.2)+(C.3.9), (A.2)+(B.2.2)+(C.3.9), (A.3)+(B.2.2)+(C.3.9), (A.4)+(B.2.2)+(C.3.9), (A.1)+(B.2.3)+(C.3.9), (A.2)+(B.2.3)+(C.3.9), (A.3)+(B.2.3)+(C.3.9), (A.4)+(B.2.3)+(C.3.9), (A.1)+(B.2.4)+(C.3.9), (A.2)+(B.2.4)+(C.3.9), (A.3)+(B.2.4)+(C.3.9), (A.4)+(B.2.4)+(C.3.9), (A.1)+(B.2.5)+(C.3.9), (A.2)+(B.2.5)+(C.3.9), (A.3)+(B.2.5)+(C.3.9), (A.4)+(B.2.5)+(C.3.9), (A.1)+(B.2.6)+(C.3.9), (A.2)+(B.2.6)+(C.3.9), (A.3)+(B.2.6)+(C.3.9), (A.4)+(B.2.6)+(C.3.9), (A.1)+(B.2.7)+(C.3.9), (A.2)+(B.2.7)+(C.3.9), (A.3)+(B.2.7)+(C.3.9), (A.4)+(B.2.7)+(C.3.9), (A.1)+(B.2.8)+(C.3.9), (A.2)+(B.2.8)+(C.3.9), (A.3)+(B.2.8)+(C.3.9), (A.4)+(B.2.8)+(C.3.9).

(A.1)+(B.1.1)+(C.3.10), (A.2)+(B.1.1)+(C.3.10), (A.3)+(B.1.1)+(C.3.10), (A.4)+(B.1.1)+(C.3.10), (A.1)+(B.1.2)+(C.3.10), (A.2)+(B.1.2)+(C.3.10), (A.3)+(B.1.2)+(C.3.10), (A.4)+(B.1.2)+(C.3.10), (A.1)+(B.1.3)+(C.3.10), (A.2)+(B.1.3)+(C.3.10), (A.3)+(B.1.3)+(C.3.10), (A.4)+(B.1.3)+(C.3.10), (A.1)+(B.1.4)+(C.3.10), (A.2)+(B.1.4)+(C.3.10), (A.3)+(B.1.4)+(C.3.10), (A.4)+(B.1.4)+(C.3.10), (A.1)+(B.1.5)+(C.3.10), (A.2)+(B.1.5)+(C.3.10), (A.3)+(B.1.5)+(C.3.10), (A.4)+(B.1.5)+(C.3.10), (A.1)+(B.1.6)+(C.3.10), (A.2)+(B.1.6)+(C.3.10), (A.3)+(B.1.6)+(C.3.10), (A.4)+(B.1.6)+(C.3.10), (A.1)+(B.1.7)+(C.3.10), (A.2)+(B.1.7)+(C.3.10), (A.3)+(B.1.7)+(C.3.10), (A.4)+(B.1.7)+(C.3.10), (A.1)+(B.1.8)+(C.3.10), (A.2)+(B.1.8)+(C.3.10), (A.3)+(B.1.8)+(C.3.10), (A.4)+(B.1.8)+(C.3.10), (A.1)+(B.1.9)+(C.3.10), (A.2)+(B.1.9)+(C.3.10), (A.3)+(B.1.9)+(C.3.10), (A.4)+(B.1.9)+(C.3.10), (A.1)+(B.1.10)+(C.3.10), (A.2)+(B.1.10)+(C.3.10), (A.3)+(B.1.10)+(C.3.10), (A.4)+(B.1.10)+(C.3.10), (A.1)+(B.1.11)+(C.3.10), (A.2)+(B.1.11)+(C.3.10), (A.3)+(B.1.11)+(C.3.10), (A.4)+(B.1.11)+(C.3.10), (A.1)+(B.1.12)+(C.3.10), (A.2)+(B.1.12)+(C.3.10), (A.3)+(B.1.12)+(C.3.10), (A.4)+(B.1.12)+(C.3.10), (A.1)+(B.1.13)+(C.3.10), (A.2)+(B.1.13)+(C.3.10), (A.3)+(B.1.13)+(C.3.10), (A.4)+(B.1.13)+(C.3.10), (A.1)+(B.1.14)+(C.3.10), (A.2)+(B.1.14)+(C.3.10), (A.3)+(B.1.14)+(C.3.10), (A.4)+(B.1.14)+(C.3.10), (A.1)+(B.1.15)+(C.3.10), (A.2)+(B.1.15)+(C.3.10), (A.3)+(B.1.15)+(C.3.10), (A.4)+(B.1.15)+(C.3.10), (A.1)+(B.1.16)+(C.3.10), (A.2)+(B.1.16)+(C.3.10), (A.3)+(B.1.16)+(C.3.10), (A.4)+(B.1.16)+(C.3.10), (A.1)+(B.1.17)+(C.3.10), (A.2)+(B.1.17)+(C.3.10), (A.3)+(B.1.17)+(C.3.10), (A.4)+(B.1.17)+(C.3.10), (A.1)+(B.2.1)+(C.3.10), (A.2)+(B.2.1)+(C.3.10), (A.3)+(B.2.1)+(C.3.10), (A.4)+(B.2.1)+(C.3.10), (A.1)+(B.2.2)+(C.3.10), (A.2)+(B.2.2)+(C.3.10), (A.3)+(B.2.2)+(C.3.10), (A.4)+(B.2.2)+(C.3.10), (A.1)+(B.2.3)+(C.3.10), (A.2)+(B.2.3)+(C.3.10), (A.3)+(B.2.3)+(C.3.10), (A.4)+(B.2.3)+(C.3.10), (A.1)+(B.2.4)+(C.3.10), (A.2)+(B.2.4)+(C.3.10), (A.3)+(B.2.4)+(C.3.10), (A.4)+(B.2.4)+(C.3.10), (A.1)+(B.2.5)+(C.3.10), (A.2)+(B.2.5)+(C.3.10), (A.3)+(B.2.5)+(C.3.10), (A.4)+(B.2.5)+(C.3.10), (A.1)+(B.2.6)+(C.3.10), (A.2)+(B.2.6)+(C.3.10), (A.3)+(B.2.6)+(C.3.10), (A.4)+(B.2.6)+(C.3.10), (A.1)+(B.2.7)+(C.3.10), (A.2)+(B.2.7)+(C.3.10), (A.3)+(B.2.7)+(C.3.10), (A.4)+(B.2.7)+(C.3.10), (A.1)+(B.2.8)+(C.3.10), (A.2)+(B.2.8)+(C.3.10), (A.3)+(B.2.8)+(C.3.10), (A.4)+(B.2.8)+(C.3.10).

(A.1)+(B.1.1)+(C.4.1), (A.2)+(B.1.1)+(C.4.1), (A.3)+(B.1.1)+(C.4.1), (A.4)+(B.1.1)+(C.4.1), (A.1)+(B.1.2)+(C.4.1), (A.2)+(B.1.2)+(C.4.1), (A.3)+(B.1.2)+(C.4.1), (A.4)+(B.1.2)+(C.4.1), (A.1)+(B.1.3)+(C.4.1), (A.2)+(B.1.3)+(C.4.1), (A.3)+(B.1.3)+(C.4.1), (A.4)+(B.1.3)+

(C.4.1), (A.1)+(B.1.4)+(C.4.1), (A.2)+(B.1.4)+(C.4.1), (A.3)+(B.1.4)+(C.4.1), (A.4)+(B.1.4)+(C.4.1), (A.1)+(B.1.5)+(C.4.1), (A.2)+(B.1.5)+(C.4.1), (A.3)+(B.1.5)+(C.4.1), (A.4)+(B.1.5)+(C.4.1), (A.1)+(B.1.6)+(C.4.1), (A.2)+(B.1.6)+(C.4.1), (A.3)+(B.1.6)+(C.4.1), (A.4)+(B.1.6)+(C.4.1), (A.1)+(B.1.7)+(C.4.1), (A.2)+(B.1.7)+(C.4.1), (A.3)+(B.1.7)+(C.4.1), (A.4)+(B.1.7)+(C.4.1), (A.1)+(B.1.8)+(C.4.1), (A.2)+(B.1.8)+(C.4.1), (A.3)+(B.1.8)+(C.4.1), (A.4)+(B.1.8)+(C.4.1), (A.1)+(B.1.9)+(C.4.1), (A.2)+(B.1.9)+(C.4.1), (A.3)+(B.1.9)+(C.4.1), (A.4)+(B.1.9)+(C.4.1), (A.1)+(B.1.10)+(C.4.1), (A.2)+(B.1.10)+(C.4.1), (A.3)+(B.1.10)+(C.4.1), (A.4)+(B.1.10)+(C.4.1), (A.1)+(B.1.11)+(C.4.1), (A.2)+(B.1.11)+(C.4.1), (A.3)+(B.1.11)+(C.4.1), (A.4)+(B.1.11)+(C.4.1), (A.1)+(B.1.12)+(C.4.1), (A.2)+(B.1.12)+(C.4.1), (A.3)+(B.1.12)+(C.4.1), (A.4)+(B.1.12)+(C.4.1), (A.1)+(B.1.13)+(C.4.1), (A.2)+(B.1.13)+(C.4.1), (A.3)+(B.1.13)+(C.4.1), (A.4)+(B.1.13)+(C.4.1), (A.1)+(B.1.14)+(C.4.1), (A.2)+(B.1.14)+(C.4.1), (A.3)+(B.1.14)+(C.4.1), (A.4)+(B.1.14)+(C.4.1), (A.1)+(B.1.15)+(C.4.1), (A.2)+(B.1.15)+(C.4.1), (A.3)+(B.1.15)+(C.4.1), (A.4)+(B.1.15)+(C.4.1), (A.1)+(B.1.16)+(C.4.1), (A.2)+(B.1.16)+(C.4.1), (A.3)+(B.1.16)+(C.4.1), (A.4)+(B.1.16)+(C.4.1), (A.1)+(B.1.17)+(C.4.1), (A.2)+(B.1.17)+(C.4.1), (A.3)+(B.1.17)+(C.4.1), (A.4)+(B.1.17)+(C.4.1), (A1.1)+(B.2.1)+(C.4.1), (A.2)+(B.2.1)+(C.4.1), (A.3)+(B.2.1)+(C.4.1), (A.4)+(B.2.1)+(C.4.1), (A.1)+(B.2.2)+(C.4.1), (A.2)+(B.2.2)+(C.4.1), (A.3)+(B.2.2)+(C.4.1), (A.4)+(B.2.2)+(C.4.1), (A.1)+(B.2.3)+(C.4.1), (A.2)+(B.2.3)+(C.4.1), (A.3)+(B.2.3)+(C.4.1), (A.4)+(B.2.3)+(C.4.1), (A.1)+(B.2.4)+(C.4.1), (A.2)+(B.2.4)+(C.4.1), (A.3)+(B.2.4)+(C.4.1), (A.4)+(B.2.4)+(C.4.1), (A.1)+(B.2.5)+(C.4.1), (A.2)+(B.2.5)+(C.4.1), (A.3)+(B.2.5)+(C.4.1), (A.4)+(B.2.5)+(C.4.1), (A.1)+(B.2.6)+(C.4.1), (A.2)+(B.2.6)+(C.4.1), (A.3)+(B.2.6)+(C.4.1), (A.4)+(B.2.6)+(C.4.1), (A.1)+(B.2.7)+(C.4.1), (A.2)+(B.2.7)+(C.4.1), (A.3)+(B.2.7)+(C.4.1), (A.4)+(B.2.7)+(C.4.1), (A.1)+(B.2.8)+(C.4.1), (A.2)+(B.2.8)+(C.4.1), (A.3)+(B.2.8)+(C.4.1), (A.4)+(B.2.8)+(C.4.1).

(A.1)+(B.1.1)+(C.4.2), (A.2)+(B.1.1)+(C.4.2), (A.3)+(B.1.1)+(C.4.2), (A.4)+(B.1.1)+(C.4.2), (A.1)+(B.1.2)+(C.4.2), (A.2)+(B.1.2)+(C.4.2), (A.3)+(B.1.2)+(C.4.2), (A.4)+(B.1.2)+(C.4.2), (A.1)+(B.1.3)+(C.4.2), (A.2)+(B.1.3)+(C.4.2), (A.3)+(B.1.3)+(C.4.2), (A.4)+(B.1.3)+(C.4.2), (A.1)+(B.1.4)+(C.4.2), (A.2)+(B.1.4)+(C.4.2), (A.3)+(B.1.4)+(C.4.2), (A.4)+(B.1.4)+(C.4.2), (A.1)+(B.1.5)+(C.4.2), (A.2)+(B.1.5)+(C.4.2), (A.3)+(B.1.5)+(C.4.2), (A.4)+(B.1.5)+(C.4.2), (A.1)+(B.1.6)+(C.4.2), (A.2)+(B.1.6)+(C.4.2), (A.3)+(B.1.6)+(C.4.2), (A.4)+(B.1.6)+(C.4.2), (A.1)+(B.1.7)+(C.4.2), (A.2)+(B.1.7)+(C.4.2), (A.3)+(B.1.7)+(C.4.2), (A.4)+(B.1.7)+(C.4.2), (A.1)+(B.1.8)+(C.4.2), (A.2)+(B.1.8)+(C.4.2), (A.3)+(B.1.8)+(C.4.2), (A.4)+(B.1.8)+(C.4.2), (A.1)+(B.1.9)+(C.4.2), (A.2)+(B.1.9)+(C.4.2), (A.3)+(B.1.9)+(C.4.2), (A.4)+(B.1.9)+(C.4.2), (A.1)+(B.1.10)+(C.4.2), (A.2)+(B.1.10)+(C.4.2), (A.3)+(B.1.10)+(C.4.2), (A.4)+(B.1.10)+(C.4.2), (A.1)+(B.1.1)+(C.4.2), (A.2)+(B.1.1))+(C.4.2), (A.3)+(B.1.1))+(C.4.2), (A.4)+(B.1.11)+(C.4.2), (A.1)+(B.1.12)+(C.4.2), (A.2)+(B.1.12)+(C.4.2), (A.3)+(B.1.12)+(C.4.2), (A.4)+(B.1.12)+(C.4.2), (A.1)+(B.1.13)+(C.4.2), (A.2)+(B.1.13)+(C.4.2), (A.3)+(B.1.13)+(C.4.2), (A.4)+(B.1.13)+(C.4.2), (A.1)+(B.1.14)+(C.4.2), (A.2)+(B.1.14)+(C.4.2), (A.3)+(B.1.14)+(C.4.2), (A.4)+(B.1.14)+(C.4.2), (A.1)+(B.1.15)+(C.4.2), (A.2)+(B.1.15)+(C.4.2), (A.3)+(B.1.15)+(C.4.2), (A.4)+(B.1.15)+(C.4.2), (A.1)+(B.1.16)+(C.4.2), (A.2)+(B.1.16)+(C.4.2), (A.3)+(B.1.16)+(C.4.2), (A.4)+(B.1.16)+(C.4.2), (A.1)+(B.1.17)+(C.4.2), (A.2)+(B.1.17)+(C.4.2), (A.3)+(B.1.17)+(C.4.2), (A.4)+(B.1.17)+(C.4.2), (A.1)+(B.2.1)+(C.4.2), (0.2)+(B.2.1)+(C.4.2), (A.3)+(B.2.1)+(C.4.2), (A.4)+(B.2.1)+(C.4.2), (A.1)+(B.2.2)+(C.4.2), (A.2)+(B.2.2)+(C.4.2), (A.3)+(B.2.2)+(C.4.2), (A.4)+(B.2.2)+(C.4.2), (A.1)+(B.2.3)+(C.4.2), (A.2)+(B.2.3)+(C.4.2), (A.3)+(B.2.3)+(C.4.2), (A.4)+(B.2.3)+(C.4.2), (A.1)+(B.2.4)+(C.4.2), (A.2)+(B.2.4)+(C.4.2), (A.3)+(B.2.4)+(C.4.2), (A.4)+(B.2.4)+(C.4.2), (A.1)+(B.2.5)+(C.4.2), (A.2)+(B.2.5)+(C.4.2), (A.3)+(B.2.5)+(C.4.2), (A.4)+(B.2.5)+(C.4.2), (A.1)+(B.2.6)+(C.4.2), (A.2)+(B.2.6)+(C.4.2), (A.3)+(B.2.6)+(C.4.2), (A.4)+(B.2.6)+(C.4.2), (A.1)+(B.2.7)+(C.4.2), (A.2)+(B.2.7)+(C.4.2), (A.3)+(B.2.7)+(C.4.2), (A.4)+(B.2.7)+(C.4.2), (A.1)+(B.2.8)+(C.4.2), (A.2)+(B.2.8)+(C.4.2), (A.3)+(B.2.8)+(C.4.2), (A.4)+(B.2.8)+(C.4.2).

(A.1)+(B.1.1)+(C.4.3), (A.2)+(B.1.1)+(C.4.3), (A.3)+(B.1.1)+(C.4.3), (A.4)+(B.1.1)+(C.4.3), (A.1)+(B.1.2)+(C.4.3), (A.2)+(B.1.2)+(C.4.3), (A.3)+(B.1.2)+(C.4.3), (A.4)+(B.1.2)+(C.4.3), (A.1)+(B.1.3)+(C.4.3), (A.2)+(B.1.3)+(C.4.3), (A.3)+(B.1.3)+(C.4.3), (A.4)+(B.1.3)+(C.4.3), (A.1)+(B.1.4)+(C.4.3), (A.2)+(B.1.4)+(C.4.3), (A.3)+(B.1.4)+(C.4.3), (A.4)+(B.1.4)+(C.4.3), (A.1)+(B.1.5)+(C.4.3), (A.2)+(B.1.5)+(C.4.3), (A.3)+(B.1.5)+(C.4.3), (A.4)+(B.1.5)+(C.4.3), (A.1)+(B.1.6)+(C.4.3), (A.2)+(B.1.6)+(C.4.3), (A.3)+(B.1.6)+(C.4.3), (A.4)+(B.1.6)+(C.4.3), (A.1)+(B.1.7)+(C.4.3), (A.2)+(B.1.7)+(C.4.3), (A.3)+(B.1.7)+(C.4.3), (A.4)+(B.1.7)+(C.4.3), (A.1)+(B.1.8)+(C.4.3), (A.2)+(B.1.8)+(C.4.3), (A.3)+(B.1.8)+(C.4.3), (A.4)+(B.1.8)+(C.4.3), (A.1)+(B.1.9)+(C.4.3), (A.2)+(B.1.9)+(C.4.3), (A.3)+(B.1.9)+(C.4.3), (A.4)+(B.1.9)+(C.4.3), (A.1)+(B.1.10)+(C.4.3), (A.2)+(B.1.10)+(C.4.3), (A.3)+(B.1.10)+(C.4.3), (A.4)+(B.1.10)+(C.4.3), (A.1)+(B.1.1)+(C.4.3), (A.2)+(B.1.1))+(C.4.3), (A.3)+(B.1.1))+(C.4.3), (A.4)+(B.1.11)+(C.4.3), (A.1)+(B.1.12)+(C.4.3), (A.2)+(B.1.12)+(C.4.3), (A.3)+(B.1.12)+(C.4.3), (A.4)+(B.1.12)+(C.4.3), (A.1)+(B.1.13)+(C.4.3), (A.2)+(B.1.13)+(C.4.3), (A.3)+(B.1.13)+(C.4.3), (A.4)+(B.1.13)+(C.4.3), (A.1)+(B.1.14)+(C.4.3), (A.2)+(B.1.14)+(C.4.3), (A.3)+(B.1.14)+(C.4.3), (A.4)+(B.1.14)+(C.4.3), (A.1)+(B.1.15)+(C.4.3), (A.2)+(B.1.15)+(C.4.3), (A.3)+(B.1.15)+(C.4.3), (A.4)+(B.1.15)+(C.4.3), (A.1)+(B.1.16)+(C.4.3), (A.2)+(B.1.16)+(C.4.3), (A.3)+(B.1.16)+(C.4.3), (A.4)+(B.1.16)+(C.4.3), (A.1)+(B.1.17)+(C.4.3), (A.2)+(B.1.17)+(C.4.3), (A.3)+(B.1.17)+(C.4.3), (A.4)+(B.1.17)+(C.4.3), (A.1)+(B.2.1)+(C.4.3), (0.2)+(B.2.1)+(C.4.3), (A.3)+(B.2.1)+(C.4.3), (A.4)+(B.2.1)+(C.4.3), (A.1)+(B.2.2)+(C.4.3), (A.2)+(B.2.2)+(C.4.3), (A.3)+(B.2.2)+(C.4.3), (A.4)+(B.2.2)+(C.4.3), (A.1)+(B.2.3)+(C.4.3), (A.2)+(B.2.3)+(C.4.3), (A.3)+(B.2.3)+(C.4.3), (A.4)+(B.2.3)+(C.4.3), (A.1)+(B.2.4)+(C.4.3), (A.2)+(B.2.4)+(C.4.3), (A.3)+(B.2.4)+(C.4.3), (A.4)+(B.2.4)+(C.4.3), (A.1)+(B.2.5)+(C.4.3), (A.2)+(B.2.5)+(C.4.3), (A.3)+(B.2.5)+(C.4.3), (A.4)+(B.2.5)+(C.4.3), (A.1)+(B.2.6)+(C.4.3), (A.2)+(B.2.6)+(C.4.3), (A.3)+(B.2.6)+(C.4.3), (A.4)+(B.2.6)+(C.4.3), (A.1)+(B.2.7)+(C.4.3), (A.2)+(B.2.7)+(C.4.3), (A.3)+(B.2.7)+(C.4.3), (A.4)+(B.2.7)+(C.4.3), (A.1)+(B.2.8)+(C.4.3), (A.2)+(B.2.8)+(C.4.3), (A.3)+(B.2.8)+(C.4.3), (A.4)+(B.2.8)+(C.4.3).

(A.1)+(B.1.1)+(C.4.4), (A.2)+(B.1.1)+(C.4.4), (A.3)+(B.1.1)+(C.4.4), (A.4)+(B.1.1)+(C.4.4), (A.1)+(B.1.2)+(C.4.4), (A.2)+(B.1.2)+(C.4.4), (A.3)+(B.1.2)+(C.4.4), (A.4)+(B.1.2)+(C.4.4), (A.1)+(B.1.3)+(C.4.4), (A.2)+(B.1.3)+(C.4.4), (A.3)+(B.1.3)+(C.4.4), (A.4)+(B.1.3)+(C.4.4), (A.1)+(B.1.4)+(C.4.4), (A.2)+(B.1.4)+(C.4.4), (A.3)+(B.1.4)+(C.4.4), (A.4)+(B.1.4)+(C.4.4), (A.1)+(B.1.5)+(C.4.4), (A.2)+(B.1.5)+(C.4.4), (A.3)+(B.1.5)+(C.4.4), (A.4)+(B.1.5)+(C.4.4), (A.1)+(B.1.6)+(C.4.4), (A.2)+(B.1.6)+(C.4.4), (A.3)+(B.1.6)+(C.4.4), (A.4)+(B.1.6)+(C.4.4), (A.1)+(B.1.7)+(C.4.4), (A.2)+(B.1.7)+(C.4.4), (A.3)+(B.1.7)+(C.4.4), (A.4)+(B.1.7)+(C.4.4), (A.1)+(B.1.8)+(C.4.4), (A.2)+(B.1.8)+(C.4.4), (A.3)+(B.1.8)+(C.4.4), (A.4)+(B.1.8)+(C.4.4), (A.1)+(B.1.9)+(C.4.4), (A.2)+(B.1.9)+(C.4.4), (A.3)+(B.1.9)+(C.4.4), (A.4)+(B.1.9)+(C.4.4), (A.1)+(B.1.10)+(C.4.4), (A.2)+(B.1.10)+(C.4.4), (A.3)+(B.1.10)+(C.4.4), (A.4)+(B.1.10)+(C.4.4), (A.1)+(B.1.11)+(C.4.4), (A.2)+(B.1.11)+(C.4.4), (A.3)+(B.1.11)+(C.4.4), (A.4)+(B.1.11)+(C.4.4), (A.1)+(B.1.12)+(C.4.4), (A.2)+(B.1.12)+(C.4.4), (A.3)+(B.1.12)+(C.4.4), (A.4)+(B.1.12)+(C.4.4), (A.1)+(B.1.13)+(C.4.4), (A.2)+(B.1.13)+(C.4.4), (A.3)+(B.1.13)+(C.4.4), (A.4)+(B.1.13)+(C.4.4), (A.1)+(B.1.14)+(C.4.4), (A.2)+(B.1.14)+(C.4.4), (A.3)+(B.1.14)+(C.4.4), (A.4)+(B.1.14)+(C.4.4), (A.1)+(B.1.15)+(C.4.4), (A.2)+(B.1.15)+(C.4.4), (A.3)+(B.1.15)+(C.4.4), (A.4)+(B.1.15)+(C.4.4), (A.1)+(B.1.16)+(C.4.4), (A.2)+(B.1.16)+(C.4.4), (A.3)+(B.1.16)+(C.4.4), (A.4)+(B.1.16)+(C.4.4), (A.1)+(B.1.17)+(C.4.4), (A.2)+(B.1.17)+(C.4.4), (A.3)+(B.1.17)+(C.4.4), (A.4)+(B.1.17)+(C.4.4), (A1.1)+(B.2.1)+(C.4.4), (A.2)+(B.2.1)+(C.4.4), (A.3)+(B.2.1)+(C.4.4), (A.4)+(B.2.1)+(C.4.4), (A.1)+(B.2.2)+(C.4.4), (A.2)+(B.2.2)+(C.4.4), (A.3)+(B.2.2)+(C.4.4), (A.4)+(B.2.2)+(C.4.4), (A.1)+(B.2.3)+(C.4.4), (A.2)+(B.2.3)+(C.4.4), (A.3)+(B.2.3)+(C.4.4), (A.4)+(B.2.3)+(C.4.4), (A.1)+(B.2.4)+(C.4.4), (A.2)+(B.2.4)+(C.4.4), (A.3)+(B.2.4)+(C.4.4), (A.4)+(B.2.4)+(C.4.4), (A.1)+(B.2.5)+(C.4.4), (A.2)+(B.2.5)+(C.4.4), (A.3)+(B.2.5)+(C.4.4), (A.4)+(B.2.5)+(C.4.4), (A.1)+(B.2.6)+(C.4.4), (A.2)+(B.2.6)+(C.4.4), (A.3)+(B.2.6)+(C.4.4), (A.4)+(B.2.6)+(C.4.4), (A.1)+(B.2.7)+(C.4.4), (A.2)+(B.2.7)+(C.4.4), (A.3)+(B.2.7)+(C.4.4), (A.4)+(B.2.7)+(C.4.4), (A.1)+(B.2.8)+(C.4.4), (A.2)+(B.2.8)+(C.4.4), (A.3)+(B.2.8)+(C.4.4), (A.4)+(B.2.8)+(C.4.4).

(A.1)+(B.1.1)+(C.4.5), (A.2)+(B.1.1)+(C.4.5), (A.3)+(B.1.1)+(C.4.5), (A.4)+(B.1.1)+(C.4.5), (A.1)+(B.1.2)+(C.4.5), (A.2)+(B.1.2)+(C.4.5), (A.3)+(B.1.2)+(C.4.5), (A.4)+(B.1.2)+(C.4.5), (A.1)+(B.1.3)+(C.4.5), (A.2)+(B.1.3)+(C.4.5), (A.3)+(B.1.3)+(C.4.5), (A.4)+(B.1.3)+(C.4.5), (A.1)+(B.1.4)+(C.4.5), (A.2)+(B.1.4)+(C.4.5), (A.3)+(B.1.4)+(C.4.5), (A.4)+(B.1.4)+(C.4.5), (A.1)+(B.1.5)+(C.4.5), (A.2)+(B.1.5)+(C.4.5), (A.3)+(B.1.5)+(C.4.5), (A.4)+(B.1.5)+(C.4.5), (A.1)+(B.1.6)+(C.4.5), (A.2)+(B.1.6)+(C.4.5), (A.3)+(B.1.6)+(C.4.5), (A.4)+(B.1.6)+(C.4.5), (A.1)+(B.1.7)+(C.4.5), (A.2)+(B.1.7)+(C.4.5), (A.3)+(B.1.7)+(C.4.5), (A.4)+(B.1.7)+(C.4.5), (A.1)+(B.1.8)+(C.4.5), (A.2)+(B.1.8)+(C.4.5), (A.3)+(B.1.8)+(C.4.5), (A.4)+(B.1.8)+(C.4.5), (A.1)+(B.1.9)+(C.4.5), (A.2)+(B.1.9)+(C.4.5), (A.3)+(B.1.9)+(C.4.5), (A.4)+(B.1.9)+(C.4.5), (A.1)+(B.1.10)+(C.4.5), (A.2)+(B.1.10)+(C.4.5), (A.3)+(B.1.10)+(C.4.5), (A.4)+(B.1.10)+(C.4.5), (A.1)+(B.1.1)+(C.4.5), (A.2)+(B.1.1))+(C.4.5), (A.3)+(B.1.1))+(C.4.5), (A.4)+(B.1.11)+(C.4.5), (A.1)+(B.1.12)+(C.4.5), (A.2)+(B.1.12)+(C.4.5), (A.3)+(B.1.12)+(C.4.5), (A.4)+(B.1.12)+(C.4.5), (A.1)+(B.1.13)+(C.4.5), (A.2)+(B.1.13)+(C.4.5), (A.3)+(B.1.13)+(C.4.5), (A.4)+(B.1.13)+(C.4.5), (A.1)+(B.1.14)+(C.4.5), (A.2)+(B.1.14)+(C.4.5), (A.3)+(B.1.14)+(C.4.5), (A.4)+(B.1.14)+(C.4.5), (A.1)+(B.1.15)+(C.4.5), (A.2)+(B.1.15)+(C.4.5), (A.3)+(B.1.15)+(C.4.5), (A.4)+(B.1.15)+(C.4.5), (A.1)+(B.1.16)+(C.4.5), (A.2)+(B.1.16)+(C.4.5), (A.3)+(B.1.16)+(C.4.5), (A.4)+(B.1.16)+(C.4.5), (A.1)+(B.1.17)+(C.4.5), (A.2)+(B.1.17)+(C.4.5), (A.3)+(B.1.17)+(C.4.5), (A.4)+(B.1.17)+(C.4.5), (A.1)+(B.2.1)+(C.4.5), (A.2)+(B.2.1)+(C.4.5), (A.3)+(B.2.1)+(C.4.5), (A.4)+(B.2.1)+(C.4.5), (A.1)+(B.2.2)+(C.4.5), (A.2)+(B.2.2)+(C.4.5), (A.3)+(B.2.2)+(C.4.5), (A.4)+(B.2.2)+(C.4.5), (A.1)+(B.2.3)+(C.4.5), (A.2)+(B.2.3)+(C.4.5), (A.3)+(B.2.3)+(C.4.5), (A.4)+(B.2.3)+(C.4.5), (A.1)+(B.2.4)+(C.4.5), (A.2)+(B.2.4)+(C.4.5), (A.3)+(B.2.4)+(C.4.5), (A.4)+(B.2.4)+(C.4.5), (A.1)+(B.2.5)+(C.4.5), (A.2)+(B.2.5)+(C.4.5), (A.3)+(B.2.5)+(C.4.5), (A.4)+(B.2.5)+(C.4.5), (A.1)+(B.2.6)+(C.4.5), (A.2)+(B.2.6)+(C.4.5), (A.3)+(B.2.6)+(C.4.5), (A.4)+(B.2.6)+(C.4.5), (A.1)+(B.2.7)+(C.4.5), (A.2)+(B.2.7)+(C.4.5), (A.3)+(B.2.7)+(C.4.5), (A.4)+(B.2.7)+(C.4.5), (A.1)+(B.2.8)+(C.4.5), (A.2)+(B.2.8)+(C.4.5), (A.3)+(B.2.8)+(C.4.5), (A.4)+(B.2.8)+(C.4.5).

(A.1)+(B.1.1)+(C.4.6), (A.2)+(B.1.1)+(C.4.6), (A.3)+(B.1.1)+(C.4.6), (A.4)+(B.1.1)+(C.4.6), (A.1)+(B.1.2)+(C.4.6), (A.2)+(B.1.2)+(C.4.6), (A.3)+(B.1.2)+(C.4.6), (A.4)+(B.1.2)+(C.4.6), (A.1)+(B.1.3)+(C.4.6), (A.2)+(B.1.3)+(C.4.6), (A.3)+(B.1.3)+(C.4.6), (A.4)+(B.1.3)+(C.4.6), (A.1)+(B.1.4)+(C.4.6), (A.2)+(B.1.4)+(C.4.6), (A.3)+(B.1.4)+(C.4.6), (A.4)+(B.1.4)+(C.4.6), (A.1)+(B.1.5)+(C.4.6), (A.2)+(B.1.5)+(C.4.6), (A.3)+(B.1.5)+(C.4.6), (A.4)+(B.1.5)+(C.4.6), (A.1)+(B.1.6)+(C.4.6), (A.2)+(B.1.6)+(C.4.6), (A.3)+(B.1.6)+(C.4.6), (A.4)+(B.1.6)+(C.4.6), (A.1)+(B.1.7)+(C.4.6), (A.2)+(B.1.7)+(C.4.6), (A.3)+(B.1.7)+(C.4.6), (A.4)+(B.1.7)+(C.4.6), (A.1)+(B.1.8)+(C.4.6), (A.2)+(B.1.8)+(C.4.6), (A.3)+(B.1.8)+(C.4.6), (A.4)+(B.1.8)+(C.4.6), (A.1)+(B.1.9)+(C.4.6), (A.2)+(B.1.9)+(C.4.6), (A.3)+(B.1.9)+(C.4.6), (A.4)+(B.1.9)+(C.4.6), (A.1)+(B.1.10)+(C.4.6), (A.2)+(B.1.10)+(C.4.6), (A.3)+(B.1.10)+(C.4.6), (A.4)+(B.1.10)+(C.4.6), (A.1)+(B.1.1)+(C.4.6), (A.2)+(B.1.1))+(C.4.6), (A.3)+(B.1.1))+(C.4.6), (A.4)+(B.1.11)+(C.4.6), (A.1)+(B.1.12)+(C.4.6), (A.2)+(B.1.12)+(C.4.6), (A.3)+(B.1.12)+(C.4.6), (A.4)+(B.1.12)+(C.4.6), (A.1)+(B.1.13)+(C.4.6), (A.2)+(B.1.13)+(C.4.6), (A.3)+(B.1.13)+(C.4.6), (A.4)+(B.1.13)+(C.4.6), (A.1)+(B.1.14)+(C.4.6), (A.2)+(B.1.14)+(C.4.6), (A.3)+(B.1.14)+(C.4.6), (A.4)+(B.1.14)+(C.4.6), (A.1)+(B.1.15)+(C.4.6), (A.2)+(B.1.15)+(C.4.6), (A.3)+(B.1.15)+(C.4.6), (A.4)+(B.1.15)+(C.4.6), (A.1)+(B.1.16)+(C.4.6), (A.2)+(B.1.16)+(C.4.6), (A.3)+(B.1.16)+(C.4.6), (A.4)+(B.1.16)+(C.4.6), (A.1)+(B.1.17)+(C.4.6), (A.2)+(B.1.17)+(C.4.6), (A.3)+(B.1.17)+(C.4.6), (A.4)+(B.1.17)+(C.4.6), (A.1)+(B.2.1)+(C.4.6), (A.2)+(B.2.1)+(C.4.6), (A.3)+(B.2.1)+(C.4.6), (A.4)+(B.2.1)+(C.4.6), (A.1)+(B.2.2)+(C.4.6), (A.2)+(B.2.2)+(C.4.6), (A.3)+(B.2.2)+(C.4.6), (A.4)+(B.2.2)+(C.4.6), (A.1)+(B.2.3)+(C.4.6), (A.2)+(B.2.3)+(C.4.6), (A.3)+(B.2.3)+(C.4.6), (A.4)+(B.2.3)+(C.4.6), (A.1)+(B.2.4)+(C.4.6), (A.2)+(B.2.4)+(C.4.6), (A.3)+(B.2.4)+(C.4.6), (A.4)+(B.2.4)+(C.4.6), (A.1)+(B.2.5)+(C.4.6), (A.2)+(B.2.5)+(C.4.6), (A.3)+(B.2.5)+(C.4.6), (A.4)+(B.2.5)+(C.4.6), (A.1)+(B.2.6)+(C.4.6), (A.2)+(B.2.6)+(C.4.6), (A.3)+(B.2.6)+(C.4.6), (A.4)+(B.2.6)+(C.4.6), (A.1)+(B.2.7)+(C.4.6), (A.2)+(B.2.7)+(C.4.6), (A.3)+(B.2.7)+(C.4.6), (A.4)+(B.2.7)+(C.4.6), (A.1)+(B.2.8)+(C.4.6), (A.2)+(B.2.8)+(C.4.6), (A.3)+(B.2.8)+(C.4.6), (A.4)+(B.2.8)+(C.4.6).

(A.1)+(B.1.1)+(C.5), (A.2)+(B.1.1)+(C.5), (A.3)+(B.1.1)+(C.5), (A.4)+(B.1.1)+(C.5), (A.1)+(B.1.2)+(C.5), (A.2)+(B.1.2)+(C.5), (A.3)+(B.1.2)+(C.5), (A.4)+(B.1.2)+(C.5), (A.1)+(B.1.3)+(C.5), (A.2)+(B.1.3)+(C.5), (A.3)+(B.1.3)+(C.5), (A.4)+(B.1.3)+(C.5), (A.1)+(B.1.4)+(C.5), (A.2)+(B.1.4)+(C.5), (A.3)+(B.1.4)+(C.5), (A.4)+(B.1.4)+(C.5), (A.1)+(B.1.5)+(C.5), (A.2)+(B.1.5)+(C.5), (A.3)+(B.1.5)+(C.5), (A.4)+(B.1.5)+(C.5), (A.1)+(B.1.6)+(C.5), (A.2)+(B.1.6)+(C.5), (A.3)+(B.1.6)+(C.5), (A.4)+(B.1.6)+(C.5), (A.1)+(B.1.7)+(C.5), (A.2)+(B.1.7)+(C.5), (A.3)+(B.1.7)+(C.5), (A.4)+(B.1.7)+(C.5), (A.1)+(B.1.8)+(C.5), (A.2)+(B.1.8)+(C.5), (A.3)+(B.1.8)+(C.5), (A.4)+(B.1.8)+(C.5), (A.1)+(B.1.9)+(C.5), (A.2)+(B.1.9)+(C.5), (A.3)+(B.1.9)+(C.5), (A.4)+(B.1.9)+(C.5), (A.1)+(B.1.10)+(C.5), (A.2)+(B.1.10)+(C.5), (A.3)+(B.1.10)+(C.5), (A.4)+(B.1.10)+(C.5), (A.1)+(B.1.11)+(C.5), (A.2)+(B.1.11)+(C.5), (A.3)+(B.1.11)+(C.5), (A.4)+(B.1.11)+(C.5), (A.1)+(B.1.12)+(C.5), (A.2)+(B.1.12)+(C.5), (A.3)+(B.1.12)+(C.5), (A.4)+(B.1.12)+(C.5), (A.1)+(B.1.13)+(C.5), (A.2)+(B.1.13)+(C.5), (A.3)+(B.1.13)+(C.5), (A.4)+(B.1.13)+(C.5), (A.1)+(B.1.14)+(C.5), (A.2)+(B.1.14)+(C.5), (A.3)+(B.1.14)+(C.5), (A.4)+(B.1.14)+(C.5), (A.1)+(B.1.15)+(C.5), (A.2)+(B.1.15)+(C.5), (A.3)+(B.1.15)+(C.5), (A.4)+(B.1.15)+(C.5), (A.1)+(B.1.16)+(C.5), (A.2)+(B.1.16)+(C.5), (A.3)+(B.1.16)+(C.5), (A.4)+(B.1.16)+(C.5), (A.1)+(B.1.17)+(C.5), (A.2)+(B.1.17)+(C.5), (A.3)+(B.1.17)+(C.5), (A.4)+(B.1.17)+(C.5), (A.1)+(B.2.1)+(C.5), (A.2)+(B.2.1)+(C.5), (A.3)+(B.2.1)+(C.5), (A.4)+(B.2.1)+(C.5), (A.1)+(B.2.2)+(C.5), (A.2)+(B.2.2)+(C.5), (A.3)+(B.2.2)+(C.5), (A.4)+(B.2.2)+(C.5), (A.1)+(B.2.3)+(C.5), (A.2)+(B.2.3)+(C.5), (A.3)+(B.2.3)+(C.5), (A.4)+(B.2.3)+(C.5), (A.1)+(B.2.4)+(C.5), (A.2)+(B.2.4)+(C.5), (A.3)+(B.2.4)+(C.5), (A.4)+(B.2.4)+(C.5), (A.1)+(B.2.5)+(C.5), (A.2)+(B.2.5)+(C.5), (A.3)+(B.2.5)+(C.5), (A.4)+(B.2.5)+(C.5), (A.1)+(B.2.6)+(C.5), (A.2)+(B.2.6)+(C.5), (A.3)+(B.2.6)+(C.5), (A.4)+(B.2.6)+(C.5), (A.1)+(B.2.7)+(C.5), (A.2)+(B.2.7)+(C.5), (A.3)+(B.2.7)+(C.5), (A.4)+(B.2.7)+(C.5), (A.1)+(B.2.8)+(C.5), (A.2)+(B.2.8)+(C.5), (A.3)+(B.2.8)+(C.5), (A.4)+(B.2.8)+(C.5).

Out of these the following combinations are even further preferred:

(A.1)+(B.1.1)+(C.1.1), (A.2)+(B.1.1)+(C.1.1), (A.1)+(B.1.2)+(C.1.1), (A.2)+(B.1.2)+(C.1.1), (A.1)+(B.1.3)+(C.1.1), (A.2)+(B.1.3)+(C.1.1), (A.1)+(B.1.4)+(C.1.1), (A.2)+(B.1.4)+(C.1.1), (A.1)+(B.1.5)+(C.1.1), (A.2)+(B.1.5)+(C.1.1), (A.1)+(B.1.6)+(C.1.1), (A.2)+(B.1.6)+(C.1.1), (A.1)+(B.1.7)+(C.1.1), (A.2)+(B.1.7)+(C.1.1), (A.1)+(B.1.8)+(C.1.1), (A.2)+(B.1.8)+(C.1.1), (A.1)+(B.1.9)+(C.1.1), (A.2)+(B.1.9)+(C.1.1), (A.1)+(B.1.10)+(C.1.1), (A.2)+(B.1.10)+(C.1.1), (A.1)+(B.1.11)+(C.1.1), (A.2)+(B.1.11)+(C.1.1), (A.1)+(B.2.1)+(C.1.1), (A.2)+(B.2.1)+(C.1.1).

(A.1)+(B.1.1)+(C.1.2), (A.2)+(B.1.1)+(C.1.2), (A.1)+(B.1.2)+(C.1.2), (A.2)+(B.1.2)+(C.1.2), (A.1)+(B.1.3)+(C.1.2), (A.2)+(B.1.3)+(C.1.2), (A.1)+(B.1.4)+(C.1.2), (A.2)+(B.1.4)+(C.1.2), (A.1)+(B.1.5)+(C.1.2), (A.2)+(B.1.5)+(C.1.2), (A.1)+(B.1.6)+(C.1.2), (A.2)+(B.1.6)+(C.1.2), (A.1)+(B.1.7)+(C.1.2), (A.2)+(B.1.7)+(C.1.2), (A.1)+(B.1.8)+(C.1.2), (A.2)+(B.1.8)+(C.1.2), (A.1)+(B.1.9)+(C.1.2), (A.2)+(B.1.9)+(C.1.2), (A.1)+(B.1.10)+(C.1.2), (A.2)+(B.1.10)+(C.1.2), (A.1)+(B.1.11)+(C.1.2), (A.2)+(B.1.11)+(C.1.2), (A.1)+(B.2.1)+(C.1.2), (A.2)+(B.2.1)+(C.1.2).

(A.1)+(B.1.1)+(C.1.3), (A.2)+(B.1.1)+(C.1.3), (A.1)+(B.1.2)+(C.1.3), (A.2)+(B.1.2)+(C.1.3), (A.1)+(B.1.3)+(C.1.3), (A.2)+(B.1.3)+(C.1.3), (A.1)+(B.1.4)+(C.1.3), (A.2)+(B.1.4)+(C.1.3), (A.1)+(B.1.5)+(C.1.3), (A.2)+(B.1.5)+(C.1.3), (A.1)+(B.1.6)+(C.1.3), (A.2)+(B.1.6)+(C.1.3), (A.1)+(B.1.7)+(C.1.3), (A.2)+(B.1.7)+(C.1.3), (A.1)+(B.1.8)+(C.1.3), (A.2)+(B.1.8)+(C.1.3), (A.1)+(B.1.9)+(C.1.3), (A.2)+(B.1.9)+(C.1.3), (A.1)+(B.1.10)+(C.1.3), (A.2)+(B.1.10)+(C.1.3), (A.1)+(B.1.11)+(C.1.3), (A.2)+(B.1.11)+(C.1.3), (A.1)+(B.2.1)+(C.1.3), (A.2)+(B.2.1)+(C.1.3).

(A.1)+(B.1.1)+(C.2.1), (A.2)+(B.1.1)+(C.2.1), (A.1)+(B.1.2)+(C.2.1), (A.2)+(B.1.2)+(C.2.1), (A.1)+(B.1.3)+(C.2.1), (A.2)+(B.1.3)+(C.2.1), (A.1)+(B.1.4)+(C.2.1), (A.2)+(B.1.4)+(C.2.1), (A.1)+(B.1.5)+(C.2.1), (A.2)+(B.1.5)+(C.2.1), (A.1)+(B.1.6)+(C.2.1), (A.2)+(B.1.6)+(C.2.1), (A.1)+(B.1.7)+(C.2.1), (A.2)+(B.1.7)+(C.2.1), (A.1)+(B.1.8)+(C.2.1), (A.2)+(B.1.8)+(C.2.1), (A.1)+(B.1.9)+(C.2.1), (A.2)+(B.1.9)+(C.2.1), (A.1)+(B.1.10)+(C.2.1), (A.2)+(B.1.10)+(C.2.1), (A.1)+(B.1.11)+(C.2.1), (A.2)+(B.1.11)+(C.2.1), (A.1)+(B.2.1)+(C.2.1), (A.2)+(B.2.1)+(C.2.1).

(A.1)+(B.1.1)+(C.2.3), (A.2)+(B.1.1)+(C.2.3), (A.1)+(B.1.2)+(C.2.3), (A.2)+(B.1.2)+(C.2.3), (A.1)+(B.1.3)+(C.2.3), (A.2)+(B.1.3)+(C.2.3), (A.1)+(B.1.4)+(C.2.3), (A.2)+(B.1.4)+(C.2.3), (A.1)+(B.1.5)+(C.2.3), (A.2)+(B.1.5)+(C.2.3), (A.1)+(B.1.6)+(C.2.3), (A.2)+(B.1.6)+(C.2.3), (A.1)+(B.1.7)+(C.2.3), (A.2)+(B.1.7)+(C.2.3), (A.1)+(B.1.8)+(C.2.3), (A.2)+(B.1.8)+(C.2.3), (A.1)+(B.1.9)+(C.2.3), (A.2)+(B.1.9)+(C.2.3), (A.1)+(B.1.10)+(C.2.3), (A.2)+(B.1.10)+(C.2.3), (A.1)+(B.1.11)+(C.2.3), (A.2)+(B.1.11)+(C.2.3), (A.1)+(B.2.1)+(C.2.3), (A.2)+(B.2.1)+(C.2.3).

(A.1)+(B.1.1)+(C.3.3), (A.2)+(B.1.1)+(C.3.3), (A.1)+(B.1.2)+(C.3.3), (A.2)+(B.1.2)+(C.3.3), (A.1)+(B.1.3)+(C.3.3), (A.2)+(B.1.3)+(C.3.3), (A.1)+(B.1.4)+(C.3.3), (A.2)+(B.1.4)+(C.3.3), (A.1)+(B.1.5)+(C.3.3), (A.2)+(B.1.5)+(C.3.3), (A.1)+(B.1.6)+(C.3.3), (A.2)+(B.1.6)+(C.3.3), (A.1)+(B.1.7)+(C.3.3), (A.2)+(B.1.7)+(C.3.3), (A.1)+(B.1.8)+(C.3.3), (A.2)+(B.1.8)+(C.3.3), (A.1)+(B.1.9)+(C.3.3), (A.2)+(B.1.9)+(C.3.3), (A.1)+(B.1.10)+(C.3.3), (A.2)+(B.1.10)+(C.3.3), (A.1)+(B.1.11)+(C.3.3), (A.2)+(B.1.11)+(C.3.3), (A.1)+(B.2.1)+(C.3.3), (A.2)+(B.2.1)+(C.3.3).

(A.1)+(B.1.1)+(C.3.4), (A.2)+(B.1.1)+(C.3.4), (A.1)+(B.1.2)+(C.3.4), (A.2)+(B.1.2)+(C.3.4), (A.1)+(B.1.3)+(C.3.4), (A.2)+(B.1.3)+(C.3.4), (A.1)+(B.1.4)+(C.3.4), (A.2)+(B.1.4)+(C.3.4), (A.1)+(B.1.5)+(C.3.4), (A.2)+(B.1.5)+(C.3.4), (A.1)+(B.1.6)+(C.3.4), (A.2)+(B.1.6)+(C.3.4), (A.1)+(B.1.7)+(C.3.4), (A.2)+(B.1.7)+(C.3.4), (A.1)+(B.1.8)+(C.3.4), (A.2)+(B.1.8)+(C.3.4), (A.1)+(B.1.9)+(C.3.4), (A.2)+(B.1.9)+(C.3.4), (A.1)+(B.1.10)+(C.3.4), (A.2)+(B.1.10)+(C.3.4), (A.1)+(B.1.11)+(C.3.4), (A.2)+(B.1.11)+(C.3.4), (A.1)+(B.2.1)+(C.3.4), (A.2)+(B.2.1)+(C.3.4).

(A.1)+(B.1.1)+(C.3.5), (A.2)+(B.1.1)+(C.3.5), (A.1)+(B.1.2)+(C.3.5), (A.2)+(B.1.2)+(C.3.5), (A.1)+(B.1.3)+(C.3.5), (A.2)+(B.1.3)+(C.3.5), (A.1)+(B.1.4)+(C.3.5), (A.2)+(B.1.4)+(C.3.5), (A.1)+(B.1.5)+(C.3.5), (A.2)+(B.1.5)+(C.3.5), (A.1)+(B.1.6)+(C.3.5), (A.2)+(B.1.6)+(C.3.5), (A.1)+(B.1.7)+(C.3.5), (A.2)+(B.1.7)+(C.3.5), (A.1)+(B.1.8)+(C.3.5), (A.2)+(B.1.8)+(C.3.5), (A.1)+(B.1.9)+(C.3.5), (A.2)+(B.1.9)+(C.3.5), (A.1)+(B.1.10)+(C.3.5), (A.2)+(B.1.10)+(C.3.5), (A.1)+(B.1.11)+(C.3.5), (A.2)+(B.1.11)+(C.3.5), (A.1)+(B.2.1)+(C.3.5), (A.2)+(B.2.1)+(C.3.5).

(A.1)+(B.1.1)+(C.3.6), (A.2)+(B.1.1)+(C.3.6), (A.1)+(B.1.2)+(C.3.6), (A.2)+(B.1.2)+(C.3.6), (A.1)+(B.1.3)+(C.3.6), (A.2)+(B.1.3)+(C.3.6), (A.1)+(B.1.4)+(C.3.6), (A.2)+(B.1.4)+(C.3.6), (A.1)+(B.1.5)+(C.3.6), (A.2)+(B.1.5)+(C.3.6), (A.1)+(B.1.6)+(C.3.6), (A.2)+(B.1.6)+(C.3.6), (A.1)+(B.1.7)+(C.3.6), (A.2)+(B.1.7)+(C.3.6), (A.1)+(B.1.8)+(C.3.6), (A.2)+(B.1.8)+(C.3.6), (A.1)+(B.1.9)+(C.3.6), (A.2)+(B.1.9)+(C.3.6), (A.1)+(B.1.10)+(C.3.6), (A.2)+(B.1.10)+(C.3.6), (A.1)+(B.1.11)+(C.3.6), (A.2)+(B.1.11)+(C.3.6), (A.1)+(B.2.1)+(C.3.6), (A.2)+(B.2.1)+(C.3.6).

(A.1)+(B.1.1)+(C.3.10), (A.2)+(B.1.1)+(C.3.10), (A.1)+(B.1.2)+(C.3.10), (A.2)+(B.1.2)+(C.3.10), (A.1)+(B.1.3)+(C.3.10), (A.2)+(B.1.3)+(C.3.10), (A.1)+(B.1.4)+(C.3.10), (A.2)+(B.1.4)+(C.3.10), (A.1)+(B.1.5)+(C.3.10), (A.2)+(B.1.5)+(C.3.10), (A.1)+(B.1.6)+(C.3.10), (A.2)+(B.1.6)+(C.3.10), (A.1)+(B.1.7)+(C.3.10), (A.2)+(B.1.7)+(C.3.10), (A.1)+(B.1.8)+(C.3.10), (A.2)+(B.1.8)+(C.3.10), (A.1)+(B.1.9)+(C.3.10), (A.2)+(B.1.9)+(C.3.10), (A.1)+(B.1.10)+(C.3.10), (A.2)+(B.1.10)+(C.3.10), (A.1)+(B.1.11)+(C.3.10), (A.2)+(B.1.11)+(C.3.10), (A.1)+(B.2.1)+(C.3.10), (A.2)+(B.2.1)+(C.3.10).

(A.1)+(B.1.1)+(C.4.2), (A.2)+(B.1.1)+(C.4.2), (A.1)+(B.1.2)+(C.4.2), (A.2)+(B.1.2)+(C.4.2), (A.1)+(B.1.3)+(C.4.2), (A.2)+(B.1.3)+(C.4.2), (A.1)+(B.1.4)+(C.4.2), (A.2)+(B.1.4)+(C.4.2), (A.1)+(B.1.5)+(C.4.2), (A.2)+(B.1.5)+(C.4.2), (A.1)+(B.1.6)+(C.4.2), (A.2)+(B.1.6)+(C.4.2), (A.1)+(B.1.7)+(C.4.2), (A.2)+(B.1.7)+(C.4.2), (A.1)+(B.1.8)+(C.4.2), (A.2)+(B.1.8)+(C.4.2), (A.1)+(B.1.9)+(C.4.2), (A.2)+(B.1.9)+(C.4.2), (A.1)+(B.1.10)+(C.4.2), (A.2)+(B.1.10)+(C.4.2), (A.1)+(B.1.11)+(C.4.2), (A.2)+(B.1.11)+(C.4.2), (A.1)+(B.2.1)+(C.4.2), (A.2)+(B.2.1)+(C.4.2).

(A.1)+(B.1.1)+(C.4.3), (A.2)+(B.1.1)+(C.4.3), (A.1)+(B.1.2)+(C.4.3), (A.2)+(B.1.2)+(C.4.3), (A.1)+(B.1.3)+(C.4.3), (A.2)+(B.1.3)+(C.4.3), (A.1)+(B.1.4)+(C.4.3), (A.2)+(B.1.4)+(C.4.3), (A.1)+(B.1.5)+(C.4.3), (A.2)+(B.1.5)+(C.4.3), (A.1)+(B.1.6)+(C.4.3), (A.2)+(B.1.6)+(C.4.3), (A.1)+(B.1.7)+(C.4.3), (A.2)+(B.1.7)+(C.4.3), (A.1)+(B.1.8)+(C.4.3), (A.2)+(B.1.8)+(C.4.3), (A.1)+(B.1.9)+(C.4.3), (A.2)+(B.1.9)+(C.4.3), (A.1)+(B.1.10)+(C.4.3), (A.2)+(B.1.10)+(C.4.3), (A.1)+(B.1.11)+(C.4.3), (A.2)+(B.1.11)+(C.4.3), (A.1)+(B.2.1)+(C.4.3), (A.2)+(B.2.1)+(C.4.3).

(A.1)+(B.1.1)+(C.4.5), (A.2)+(B.1.1)+(C.4.5), (A.1)+(B.1.2)+(C.4.5), (A.2)+(B.1.2)+(C.4.5), (A.1)+(B.1.3)+(C.4.5), (A.2)+(B.1.3)+(C.4.5), (A.1)+(B.1.4)+(C.4.5), (A.2)+(B.1.4)+(C.4.5), (A.1)+(B.1.5)+(C.4.5), (A.2)+(B.1.5)+(C.4.5), (A.1)+(B.1.6)+(C.4.5), (A.2)+(B.1.6)+(C.4.5), (A.1)+(B.1.7)+(C.4.5), (A.2)+(B.1.7)+(C.4.5), (A.1)+(B.1.8)+(C.4.5), (A.2)+(B.1.8)+(C.4.5), (A.1)+(B.1.9)+(C.4.5), (A.2)+(B.1.9)+(C.4.5), (A.1)+(B.1.10)+(C.4.5), (A.2)+(B.1.10)+(C.4.5), (A.1)+(B.1.11)+(C.4.5), (A.2)+(B.1.11)+(C.4.5), (A.1)+(B.2.1)+(C.4.5), (A.2)+(B.2.1)+(C.4.5).

(A.1)+(B.1.1)+(C.4.6), (A.2)+(B.1.1)+(C.4.6), (A.1)+(B.1.2)+(C.4.6), (A.2)+(B.1.2)+(C.4.6), (A.1)+(B.1.3)+(C.4.6), (A.2)+(B.1.3)+(C.4.6), (A.1)+(B.1.4)+(C.4.6), (A.2)+(B.1.4)+(C.4.6), (A.1)+(B.1.5)+(C.4.6), (A.2)+(B.1.5)+(C.4.6), (A.1)+(B.1.6)+(C.4.6), (A.2)+(B.1.6)+(C.4.6), (A.1)+(B.1.7)+(C.4.6), (A.2)+(B.1.7)+(C.4.6), (A.1)+(B.1.8)+(C.4.6), (A.2)+(B.1.8)+(C.4.6), (A.1)+(B.1.9)+(C.4.6), (A.2)+(B.1.9)+(C.4.6), (A.1)+(B.1.10)+(C.4.6), (A.2)+(B.1.10)+(C.4.6), (A.1)+(B.1.11)+(C.4.6), (A.2)+(B.1.11)+(C.4.6), (A.1)+(B.2.1)+(C.4.6), (A.2)+(B.2.1)+(C.4.6).

(A.1)+(B.1.1)+(C.5), (A.2)+(B.1.1)+(C.5), (A.1)+(B.1.2)+(C.5), (A.2)+(B.1.2)+(C.5), (A.1)+(B.1.3)+(C.5), (A.2)+(B.1.3)+(C.5), (A.1)+(B.1.4)+(C.5), (A.2)+(B.1.4)+(C.5), (A.1)+(B.1.5)+(C.5), (A.2)+(B.1.5)+(C.5), (A.1)+(B.1.6)+(C.5), (A.2)+(B.1.6)+(C.5), (A.1)+(B.1.7)+(C.5), (A.2)+(B.1.7)+(C.5), (A.1)+(B.1.8)+(C.5), (A.2)+(B.1.8)+(C.5), (A.1)+(B.1.9)+(C.5), (A.2)+(B.1.9)+(C.5), (A.1)+(B.1.10)+(C.5), (A.2)+(B.1.10)+(C.5), (A.1)+(B.1.11)+(C.5), (A.2)+(B.1.11)+(C.5), (A.1)+(B.2.1)+(C.5), (A.2)+(B.2.1)+(C.5).

Even more preference is given to the following combinations:

(A.1)+(B.1.1)+(C.1.1), (A.2)+(B.1.1)+(C.1.1), (A.1)+(B.1.2)+(C.1.1), (A.2)+(B.1.2)+(C.1.1), (A.1)+(B.1.3)+(C.1.1), (A.2)+(B.1.3)+(C.1.1), (A.1)+(B.1.4)+(C.1.1), (A.2)+(B.1.4)+(C.1.1), (A.1)+(B.1.5)+(C.1.1), (A.2)+(B.1.5)+(C.1.1), (A.1)+(B.2.1)+(C.1.1), (A.2)+(B.2.1)+(C.1.1).

(A.1)+(B.1.1)+(C.1.2), (A.2)+(B.1.1)+(C.1.2), (A.1)+(B.1.2)+(C.1.2), (A.2)+(B.1.2)+(C.1.2), (A.1)+(B.1.3)+(C.1.2), (A.2)+(B.1.3)+(C.1.2), (A.1)+(B.1.4)+(C.1.2), (A.2)+(B.1.4)+(C.1.2), (A.1)+(B.1.5)+(C.1.2), (A.2)+(B.1.5)+(C.1.2), (A.1)+(B.2.1)+(C.1.2), (A.2)+(B.2.1)+(C.1.2).

(A.1)+(B.1.1)+(C.1.3), (A.2)+(B.1.1)+(C.1.3), (A.1)+(B.1.2)+(C.1.3), (A.2)+(B.1.2)+(C.1.3), (A.1)+(B.1.3)+(C.1.3), (A.2)+(B.1.3)+(C.1.3), (A.1)+(B.1.4)+(C.1.3), (A.2)+(B.1.4)+(C.1.3), (A.1)+(B.1.5)+(C.1.3), (A.2)+(B.1.5)+(C.1.3), (A.1)+(B.2.1)+(C.1.3), (A.2)+(B.2.1)+(C.1.3).

(A.1)+(B.1.1)+(C.2.1), (A.2)+(B.1.1)+(C.2.1), (A.1)+(B.1.2)+(C.2.1), (A.2)+(B.1.2)+(C.2.1), (A.1)+(B.1.3)+(C.2.1), (A.2)+(B.1.3)+(C.2.1), (A.1)+(B.1.4)+(C.2.1), (A.2)+(B.1.4)+(C.2.1), (A.1)+(B.1.5)+(C.2.1), (A.2)+(B.1.5)+(C.2.1), (A.1)+(B.2.1)+(C.2.1), (A.2)+(B.2.1)+(C.2.1).

(A.1)+(B.1.1)+(C.2.3), (A.2)+(B.1.1)+(C.2.3), (A.1)+(B.1.2)+(C.2.3), (A.2)+(B.1.2)+(C.2.3), (A.1)+(B.1.3)+(C.2.3), (A.2)+(B.1.3)+(C.2.3), (A.1)+(B.1.4)+(C.2.3), (A.2)+(B.1.4)+(C.2.3), (A.1)+(B.1.5)+(C.2.3), (A.2)+(B.1.5)+(C.2.3), (A.1)+(B.2.1)+(C.2.3), (A.2)+(B.2.1)+(C.2.3).

(A.1)+(B.1.1)+(C.3.3), (A.2)+(B.1.1)+(C.3.3), (A.1)+(B.1.2)+(C.3.3), (A.2)+(B.1.2)+(C.3.3), (A.1)+(B.1.3)+(C.3.3), (A.2)+(B.1.3)+(C.3.3), (A.1)+(B.1.4)+(C.3.3), (A.2)+(B.1.4)+(C.3.3), (A.1)+(B.1.5)+(C.3.3), (A.2)+(B.1.5)+(C.3.3), (A.1)+(B.2.1)+(C.3.3), (A.2)+(B.2.1)+(C.3.3).

(A.1)+(B.1.1)+(C.3.10), (A.2)+(B.1.1)+(C.3.10), (A.1)+(B.1.2)+(C.3.10), (A.2)+(B.1.2)+(C.3.10), (A.1)+(B.1.3)+(C.3.10), (A.2)+(B.1.3)+(C.3.10), (A.1)+(B.1.4)+(C.3.10), (A.2)+(B.1.4)+(C.3.10), (A.1)+(B.1.5)+(C.3.10), (A.2)+(B.1.5)+(C.3.10), (A.1)+(B.2.1)+(C.3.10), (A.2)+(B.2.1)+(C.3.10).

(A.1)+(B.1.1)+(C.4.5), (A.2)+(B.1.1)+(C.4.5), (A.1)+(B.1.2)+(C.4.5), (A.2)+(B.1.2)+(C.4.5), (A.1)+(B.1.3)+(C.4.5), (A.2)+(B.1.3)+(C.4.5), (A.1)+(B.1.4)+(C.4.5), (A.2)+(B.1.4)+(C.4.5), (A.1)+(B.1.5)+(C.4.5), (A.2)+(B.1.5)+(C.4.5), (A.1)+(B.2.1)+(C.4.5), (A.2)+(B.2.1)+(C.4.5).

(A.1)+(B.1.1)+(C.4.6), (A.2)+(B.1.1)+(C.4.6), (A.1)+(B.1.2)+(C.4.6), (A.2)+(B.1.2)+(C.4.6), (A.1)+(B.1.3)+(C.4.6), (A.2)+(B.1.3)+(C.4.6), (A.1)+(B.1.4)+(C.4.6), (A.2)+(B.1.4)+(C.4.6), (A.1)+(B.1.5)+(C.4.6), (A.2)+(B.1.5)+(C.4.6), (A.1)+(B.2.1)+(C.4.6), (A.2)+(B.2.1)+(C.4.6).

(A.1)+(B.1.1)+(C.5), (A.2)+(B.1.1)+(C.5), (A.1)+(B.1.2)+(C.5), (A.2)+(B.1.2)+(C.5), (A.1)+(A) (B.1.3)+(C.5), (A.2)+(B.1.3)+(C.5), (A.1)+(B.1.4)+(C.5), (A.2)+(B.1.4)+(C.5), (A.1)+(B.1.5)+(C.5), (A.2)+(B.1.5)+(C.5), (A.1)+(B.2.1)+(C.5), (A.2)+(B.2.1)+(C.5).

Most preference is given to the following combinations:
(A.2)+(B1.1)
(A.2)+(B.1.1)+(C.1.1), (A.2)+(B.1.1)+(C.1.2), (B.1.1)+(C.1.3), (A.2)+(B.1.1)+(C.2.1), (A.2)+(B.1.1)+(C.2.3), (A.2)+(B.1.1)+(C.3.3), (A.2)+(B.1.1)+(C.3.10), (A.2)+(B.1.1)+(C.4.5), (A.2)+(B.1.1)+(C.4.6), A.2)+(B.1.1)+(C.5).

All ternary combinations mentioned above can be combined with at least one further known bactericide, fungicide, acaricide, nematicide, herbicide, insecticide, micronutrients and micronutrient-containing compound, safener, lipochito-oligosaccharides (LCO), soil-improvement product or product for reducing plant stress, for example Myconate, in order to widen the spectrum of action or to prevent the development of resistance, for example.

Preferably, the ternary and quaternary combinations mentioned above may be further combined with at least one compound selected from the group consisting of (A.1) acibenzolar-S-methyl, (A.2) isotianil, (A.3) probenazole, (A.4) tiadinil, (C.2.1) Fosetyl-Al, (C.2.4) azoxystrobin, (C.2.3) trifloxystrobin, (C.3.3) imidacloprid, (C.3.4) thiacloprid, (C.3.5) betacyfluthrin, (C.3.6) deltamethrin, (C.3.10) flupyradifurone, (C.4.1) copper (Cu), (C.4.2) copper-hydroxyde, (C.4.3) copper-sulphate, (C.4.4) copper-oxychloride, (C.4.5) Propineb, (C.4.6) Mancozeb, and (C.5) Myconate.

All named combination partners, as well as the host defense inducers of the present invention can, if their functional groups enable this, optionally form salts with suitable bases or acids.

Further, the host defense inducers of the present invention can be combined with at least one active compound selected from the group consisting of:

Acetic acid (e.g. naphthalene acetic acid), peracetic acid, organic acids (e.g. citric acid, lactic acid), amino acids (e.g. 1-arginine), humic acids, fulvic acids, boric acid, oxolinic acid, 1,2,3-Benzothiadiazole-7-thiocarboxylic acid-S-methyl-ester, 5-hydroxy-1,4-naphthalenedione, bromo-chloro-dimethylhydantoin, Trichloroisoyanuric acid, salicylic acid, dichlorophen, kanamycin, kasugamycin, streptomycin, strepromycin sulfate, oxytetracycline, gentamycin (e.g. gentamycin sulphate hydrate), imidacloprid, tebuconazole thiabendzole, thiram, teracep, octhilinone, quinoxyfen, azadirachtin, furanoflavone, forchlorfenuron, plant minerals (e.g. calcium, calcium calcium carbonate, hypochlorite, calcium EDTA), enzymes (e.g. protease, amylase, lipase), trace elements and chelated trace elements (e.g. as amino acid chelates), vitamins and plant extracts, salicylate derivatives, bioflavonoids and organic acids derived from vegetables and fruit, natural fruit extracted polyphenols, bitter orange oil, citrus extracts, chitosan, starch, seaweed extract, organosilicone, activated ionized silicon complex (Zumsil®), bee wax, urea, *Bacillus subtilis, Bacillus amyloliquefaciens, Pseudomonas fluorescens, Pseudomonas putida, Pantoea agglomerans, Trichoderma koningii, Trichoderma harzianum*, chlorine and chlorine compounds (e.g. chlorinated water, chlorine dioxide, sodium chlorite, sodium hypochlorite, hypochlorous acid, ammonium chloride, didecyl dimethyl ammonium chloride, benzalkonium chloride), oxygen, hydrogen peroxide ($H_2O_2$) and peroxygen compounds, hydrogen cyanamide, nickel (III) sulphate, sodium persulphate, phosphite, phosphate, Trisodium phosphate, phosphoric acid, inorganic nitrogen, silver and silver containing compounds (e.g. colloidal silver), glutaraldehyde, rhamnolipid (Zonix®).

Thereunder, preference is given to combinations of at least one of the host defense inducers of the present invention with at least one further compound selected from the group consisting of:

Fosetyl-Al, strobilurins preferably selected from azoxystrobin and trifloxystrobin and micronutrients and micronutrient-containing compounds as defined herein, preferably selected from copper (Cu), copper-hydroxyde, copper-sulphate, copper-oxychloride, Propineb, and Mancozeb.

In this context and within the meaning of the present invention, the term "combination" or "formulation" means various combinations of at least one host defense inducer with at least one biological control agent and optionally at least one compound (C), each as defined herein, and which may be provided, for example, in the form of ready mixes, tank mixes (which is understood as meaning spray slurries prepared from the formulations of the individual active compounds by combining and diluting prior to the application) or combinations of these (for example, a binary ready mix of two of the abovementioned active compounds is made into a tank mix by using a formulation of the third individual substance).

Application Forms and Method of Treatment

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. Preference is given to application by dipping, spraying, atomizing, irrigating, evaporating, dusting, fogging, broadcasting, foaming, painting, spreading-on, watering (drenching) and drip irrigating. Also encompassed by the present invention is nursery box treatment.

The treatment according to the present invention may be carried out curatively as well as preventively.

According to the invention, the individual active compounds may also be employed sequentially, i.e. one after the other, at a reasonable interval of a few hours or days, in the case of the treatment of seed for example also by applying a plurality of layers which contain different active compounds. Preferably, it is immaterial in which order the individual active compounds can be employed.

In an especially preferred embodiment of the present invention, the combinations comprising the host defense inducers and biological control agents or their formulations are used for application in the form of solutions, emulsions or suspensions to be applied by spraying, for the treatment of vegetative propagation material, or for rhizome or foliar application.

Depending on its respective physical and/or chemical properties, the selected compounds of the combinations of the present invention can be converted into the customary formulations, such as solutions, emulsions, suspensions, powders, foams, pastes, granules, sachets, aerosols, micro-encapsulations in polymeric substances, and ULV cold- and hot-fogging formulations.

These formulations are prepared in a known manner, for example by mixing the host defense inducers and/or biological control agents and/or optional additional compounds (C) with extenders, that is to say liquid solvents, pressurized liquefied gases and/or solid carriers, optionally with the use of surfactants, that is emulsifiers and/or dispersants and/or foam formers. If water is used as the extender, it is possible for example also to use organic solvents as cosolvents. Liquid solvents which are suitable in the main are: aromatics such as xylene, toluene or alkyl-naphthalenes, chlorinated aromatics or chlorinated aliphatic hydrocarbons such as chlorobenzenes, chloroethylenes or methylene chloride, aliphatic hydrocarbons, such as cyclohexane or paraffins, for example mineral oil fractions, alcohols such as butanol or glycol, and their ethers and esters, ketones such as acetone, methyl ethyl ketone, methyl isobutyl ketone or cyclohexanone, strongly polar solvents such as dimethylformamide and di-me-thyl sulph-oxide, and water, and also mineral, animal and vegetable oils such as, for example, palm oil or other plant seed oils. Liquefied gaseous extenders or carriers are understood as meaning those liquids which are gaseous at normal temperature and under normal pressure, for example aerosol propellants such as halohydrocarbons and butane, propane, nitrogen and carbon dioxide.

Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, pumice, marble, sepiolite, dolomite, and synthetic granules of inorganic and organic meals, and granules of organic material such as sawdust, coconut shells, maize cobs and tobacco stalks. Emulsifiers and/or foam formers which are suitable are: for example nonionic, cationic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and protein hydrolysates. Suitable dispersants are: for example, lignosulphite waste liquors and methylcellulose.

Adhesives such as carboxymethylcellulose, natural and synthetic polymers in the form of powders, granules or latices, such as gum arabic, polyvinyl alcohol, polyvinyl acetate, and natural phospholipids such as cephalins and lecithins, and synthetic phospholipids, may be used in the formulations. Further additives may be mineral and vegetable oils.

It is possible to use colorants such as inorganic pigments, for example iron oxide, titanium oxide, Prussian Blue, and organic dyestuffs, such as alizarin, azo and metal phthalocyanine dyestuffs, and trace nutrients, such as salts of iron, manganese, boron, copper, cobalt, molybdenum and zinc.

In general, the formulations contain between 0.1 and 95% by weight of active compound (host defense inducer, biological control agent and/or compound (C)), preferably between 0.5 and 90%.

The control of the selected bacterial harmful organisms by treating the vegetative propagation material of plants has been known for a long time and is the subject of continuous improvements. However, the treatment of vegetative propagation material involves a series of problems which cannot always be solved in a satisfactory manner. Thus, it is desirable to develop methods for protecting the vegetative propagation material and the germinating plant which do away with, or at least markedly reduce, the additional application of plant protection products after planting or after emergence of the plants. It is furthermore desirable to optimize the amount of the active compound employed such that the vegetative propagation material and the germinating plant are protected the best possible from attack by the bacterial harmful organisms without, however, damaging the plant itself by the active compound employed. In particular, methods for the treatment of vegetative propagation material should also take into consideration the intrinsic properties of transgenic plants in order to achieve an optimal protection of the vegetative propagation material and the germinating plant while keeping the application rate of plant protection products as low as possible.

The present invention therefore relates in particular also to a method of protecting vegetative propagation material and germinating plants from attack by the selected bacterial harmful organisms, by treating the seed and the vegetative propagation material with a compound or formulation according to the invention.

The invention also relates to the use of the compounds according to the invention for the treatment of vegetative propagation material for protecting the vegetative propagation material and the germinating plant from the selected bacterial harmful organisms.

One of the advantages of the present invention is that, owing to the special systemic properties of the compounds according to the invention, the treatment of the vegetative propagation material with these compounds protects not only the vegetative propagation material itself, but also the plants which it gives rise to after planting, from the bacterial harmful organisms. In this manner, the immediate treatment of the crop at the time of planting, or shortly thereafter, can be dispensed with.

Another advantage is that the compounds according to the invention can be employed in particular also in transgenic vegetative propagation material.

The compounds according to the invention are suitable for protecting vegetative propagation material of any plant variety which is employed in agriculture, in the greenhouse, in forests or in horticulture. In particular, this is vegetative propagation material of the plants as defined and preferred herein.

Within the scope of the present invention, the compounds according to the invention are applied to the vegetative propagation material either alone or in a suitable formulation. Preferably, the vegetative propagation material is treated in a state in which it is sufficiently stable such that no damage occurs during the treatment. In general, the vegetative propagation material can be treated at any point in time between harvesting and planting out. Usually, vegetative propagation material is used which has been separated from the plant and freed from cobs, shells, stalks, coats, hairs or fruit flesh.

When treating the vegetative propagation material, care must be taken in general that the amount of the compound or formulation according to the invention, and/or of further additives, applied to the vegetative propagation material is chosen such that the germination of the vegetative propagation material is not adversely affected, or that the plant which it gives rise to is not damaged. This must be considered in particular in the case of active compounds which, at certain application rates, may have phytotoxic effects.

The compounds or formulations according to the invention can be applied directly, that is to say without containing further components and without having been diluted. In general, it is preferred to apply the compounds or formulations to the vegetative propagation material in the form of a suitable formulation. Suitable formulations and methods for the treatment of seed and of vegetative propagation material are known to the skilled worker.

The compounds or formulations which can be used in accordance with the invention can be converted into the customary formulations, such as solutions, emulsions, suspensions, powders, foams and ULV formulations.

These formulations are prepared in the known manner by mixing the host defense inducers, biological control agents and optionally compounds (C) with customary additives, such as, for example, customary extenders and also solvents or diluents, colorants, wetters, dispersants, emulsifiers, antifoams, preservatives, secondary thickeners, adhesives, gibberellins, mineral and vegetable oils, and also water.

Colorants which may be present in the formulations which can be used in accordance with the invention are all colorants which are customary for such purposes. In this context, both pigments, which are sparingly soluble in water, and dyes, which are soluble in water, may be used. Examples which may be mentioned are the colorants known by the names Rhodamin B, C.I. Pigment Red 112 and C.I. Solvent Red 1.

Wetters which may be present in the formulations which can be used in accordance with the invention are all substances which are customary for formulating agrochemical active compounds and which promote wetting. Alkylnaphthalenesulphonates, such as diisopropyl- or diisobutylnaphthalenesulphonates, may preferably be used.

Suitable dispersants and/or emulsifiers which may be present in the formulations which can be used in accordance with the invention are all nonionic, anionic and cationic dispersants which are conventionally used for the formulation of agrochemical active compounds. The following may be used by preference: nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristyrylphenol polyglycol ethers and their phosphated or sulphated derivatives. Suitable anionic dispersants are, in particular, lignosulphonates, salts of polyacrylic acid, and arylsulphonate/formaldehyde condensates.

Antifoams which may be present in the formulations which can be used in accordance with the invention are all foam-inhibitor substances which are conventionally used for the formulation of agrochemical active compounds. Silicone antifoams and magnesium stearate may be used by preference.

Preservatives which may be present in the formulations which can be used in accordance with the invention are all substances which can be employed for such purposes in agrochemical compositions. Examples which may be mentioned are dichlorophene and benzyl alcohol hemiformal.

Secondary thickeners which may be present in the formulations which can be used in accordance with the invention are all substances which can be employed for such purposes in agrochemical compositions. Cellulose derivatives, acrylic acid derivatives, xanthan, modified clays and highly disperse silica are preferably suitable.

Adhesives which may be present in the formulations which can be used in accordance with the invention are all customary binders which can be used in mordants. Polyvinylpyrrolidone, polyvinyl acetate, polyvinyl alcohol and tylose may be mentioned by preference.

Gibberellins which may be present in the formulations which can be used in accordance with the invention are preferably Gibberellin A1, Gibberellin A3 (gibberellic acid), Gibberellin A4, Gibberellin A7. Especially preferred is gibberellic acid.

The gibberellins are known (cf. R. Wegler "Chemie der Pflanzenschutz- and Schädlingsbekämpfungsmittel" [Chemistry of plant protection and pesticide agents], volume 2, Springer Verlag, Berlin-Heidelberg-New York, 1970, pages 401-412).

The formulations which can be used in accordance with the invention can be employed, for the treatment of various types of seed, either directly or after previously having been diluted with water. Thus, the concentrates or the preparations obtainable therefrom by dilution with water can be employed for dressing the seed. The formulations which can be used in accordance with the invention, or their diluted preparations, can also be employed for treating the vegetative propagation material of transgenic plants. Here, additional synergistic effects may also occur in combination with the substances formed by expression.

The application rate of the formulations which can be used in accordance with the invention can be varied within a substantial range. It depends on the respective active compound content in the formulations, and on the vegetative propagation material. As a rule, the application rates of active compound are between 0.001 and 50 g per kilogram of vegetative propagation material, preferably between 0.01 and 15 g per kilogram of vegetative propagation material.

The combinations of the present invention can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, scattering, dusting, foaming, painting on and the like. It is furthermore possible to apply the compounds or formulations of the present invention by the ultra-low-volume method or to inject the active compound preparation, or the active compound itself, into the soil. The vegetative propagation material of the plants may also be treated.

The application rates may be varied within a substantial range, depending on the type of application. In the treatment of plant parts, the application rates of active compound are generally between 0.1 and 10 000 g/ha, preferably between 10 and 1000 g/ha. In the treatment of vegetative propagation material, the application rates of active compound are generally between 0.001 and 50 g per kilogram of vegetative propagation material, preferably between 0.01 and 10 g per kilogram of vegetative propagation material. In the treatment of the soil, the application rates of active compound are generally between 0.1 and 10 000 g/ha, preferably between 1 and 5000 g/ha.

The present invention further relates to Kit-of-parts combinations comprising
(A) at least one host defense inducer as defined herein,
(B) at least one biological control agent as defined herein, and
(C) optionally at least one further compound as defined herein in a synergistically effective amount for controlling bacterial harmful organisms in useful plants.

Such Kit-of-parts comprise the respective components in a spatially separated arrangement. Therein, it is possible that all components are spatially separated from each other as illustrated by e.g. A/B; A/B/C; A/A'/B/C (for example in the case of the preferred embodiment comprising a combination of isotianil and acibenzolar-S-methyl as host defense inducers (A)). It is further possible, that at least two of the components are present in a mixture and spatially separated from the at least one other component or mixture(s) such as illustrated by e.g. A+B/C; A+C/B; B+C/A; A+A'/B/C; A/A'+B/C; A/B/C+A'; A+B/A'/C; A/A'/B+C; A+A'/B+C etc. (respective combinations apply accordingly for embodiments comprising combinations of at least two biological control agents B and B' or at least two further compounds C and C' etc.). It is possible to mix at least two of the spatially separated components or mixture(s) of two components with the spatially separated third component (or further mixture(s)) before application to the plants. Alternatively the spatially separated components as described herein may be used separately and be applied sequentially in separated sequential treatment blocks as defined hereinafter.

The active compound formulations of the present invention comprise an effective and non-phytotoxic amount of the active ingredients with the expression "effective and non-phytotoxic amount" means an amount of the ingredients and the active combinations according to the invention which is sufficient for controlling or destroying pathogenic bacterial organisms present or liable to appear on the plants, by notably avoiding the development of resistant strains to the active ingredients and in each case does not entail any appreciable symptom of phytotoxicity for the said crops. Such an amount can vary within a wide range depending on the pathogen to be combated or controlled bacteria, the type of crop, the climatic conditions and the compounds included in the bactericide combination according to the invention. This amount can be determined by systematic field trials, which are within the capabilities of a person skilled in the art.

Accordingly, the present invention is further directed to a method for controlling bacterial harmful organisms in useful plants comprising treatment of the plants with a combination comprising (A) at least one host defense inducer as defined herein and (B) at least one biological control agent as defined herein and optionally at least one compound (C) as defined herein.

A preferred embodiment of the present invention relates to a method for controlling bacterial harmful organisms in useful plants, which method comprises subjecting plants to be protected against attack by bacterial harmful organisms to two or more, sequential treatment blocks, preferably 2, 3 or 4 sequential treatment blocks, where at least one treatment block comprises subjecting the plants to at least one treatment with at least one host defense inducer (A) as defined herein and at least one treatment block comprises subjecting the plants to at least one treatment with at least one biological control agent (B) as defined herein. An even more preferred embodiment of the present invention relates to a method for controlling bacterial harmful organisms in useful plants, which method comprises subjecting plants to be protected against attack by bacterial harmful organisms to two or more, sequential treatment blocks, preferably 2, 3 or 4 sequential treatment blocks, where at least one treatment block comprises subjecting the plants to at least one treatment with at least one host defense inducer (A) as defined herein and at least one treatment block comprises subjecting the plants to at least one treatment with at least one biological control agent (B) as defined herein, with the proviso that the last treatment block comprises subjecting the plants to at least one treatment with at least one biological control agent.

Within the meaning of the present invention "treatment block" refers to a treatment step which comprises one or more applications of either the at least one host defense inducer (A) or the at least one biological control agent (B). The different treatment blocks are distinguished by the type of active compounds used (one treatment block comprises the application of either the at least one host defense inducer or the at least one biological control agent) and by time (i.e. the different treatment blocks do not overlap). However, if there are more than two treatment blocks, one treatment block may comprise the combined treatment with at least one host defense inducer and at least one biological control agent, e.g. by applying a mixture of at least one host defense inducer and at least one biological control agent. Preferably, if there are more than two treatment blocks, one treatment block may comprise the combined treatment with at least one host defense inducer and at least one biological control agent, e.g. by applying a mixture of at least one host defense inducer and at least one biological control agent, with the proviso that the last treatment block comprises subjecting the plants to at least one treatment with at least one biological control agent (and no host defense inducer). It is however preferred that no treatment block comprises the combined treatment with at least one host defense inducer and at least one biological control agent; in other words it is preferred that each treatment block comprises the application of either the at least one host defense inducer or the at least one biological control agent.

The "last" treatment block is that treatment block which is the last host defense inducer treatment block in a season, e.g. before, during or latest after harvest (treatment of the crop) or before the plant's death (in case of annual plants).

Preferably, the method of the invention comprises two treatment blocks. Thus, the invention preferably relates to a method for controlling bacterial harmful organisms, which method comprises subjecting plants to be protected against phytopathogenic bacteria attack to two sequential treatment blocks, where the first treatment block comprises subjecting the plants to at least one treatment with at least one host defense inducer and the second, subsequent treatment block comprises subjecting the plants to at least one treatment with at least one biological control agent. In a treatment block which comprises subjecting the plants to at least one treatment with at least one host defense inducer, no biological control agent is applied. In a treatment block which comprises subjecting the plants to at least one treatment with at least one biological control agent, no host defense inducer is applied. In the method of the invention, a treatment block is carried out only after the preceding treatment block has been finished, i.e. the second treatment block is carried out only after the first treatment block has been finished, the third treatment block, if existent, is carried out only after the second treatment block has been finished, etc.

Preferably, the respective treatment blocks are carried out during different growth stages of the plants. In other words, the time interval between the subsequent treatment blocks is preferably such that the plants are in different growth stages when being subjected to the respective treatment blocks, i.e. the first, the second, etc. treatment blocks are carried out during non-overlapping growth stages of the plants, the first treatment block of course being carried out at earlier growth stages than the second, etc. In case of the preferred embodiment of the invention in which the method comprises two treatment blocks, preferably the time interval between the first and the second treatment block is such that the plants are in different growth stages when being subjected to the first and the second treatment blocks, respectively, i.e. the first and the second treatment blocks are preferably carried out during non-overlapping growth stages of the plants, the first treatment block of course being carried out at earlier growth stages.

"Growth stage", as used in the terms of the present invention, refers to growth stages according to the BBCH extended scale (BBCH Makrostadien; Biologische Bundesanstalt fur Land-und Forstwirtschaft [BBCH Macrostages; German Federal Biological Research Center for Agriculture and Forestry]; see www.bba.de/veroeff/bbch/bbchen.pf).

Preferably, the first treatment block ends latest when the plants have reached growth stage 81 and the last treatment block begins earliest when the plants are in growth stage 41, according to BBCH extended scale. As already pointed out, a subsequent block is always and mandatorily carried out after completion of the preceding block; which means for example that if the first treatment block has finished when the plant is in growth stage 81, the second treatment block is carried out only after the completion of the first block, preferably earliest in growth stage 82. The most suitable point of time for the treatment depends, inter alia, from the plant to be treated.

In case of the preferred embodiment of the invention in which the method comprises two treatment blocks, preferably the first treatment block ends latest when the plants have reached growth stage 81 and the second treatment block begins earliest when the plants are in growth stage 41. As already pointed out, the second block is always and mandatorily carried out after completion of the first block; which means for example, that if the first treatment block has finished when the plant is in growth stage 81, the second treatment block is carried out only after the completion of the first block, preferably earliest in growth stage 82. The most suitable point of time for the treatment depends, inter alia, from the plant to be treated.

More preferably, the first treatment block ends latest when the plants have reached growth stage 79 and the last treatment block, which is preferably the second treatment block, begins earliest when the plants are in growth stage 41. Even more preferably, the first treatment block is carried out when the plants are in the growth stage 01 to 79 preferably 10 to 79 and the last treatment block, which is preferably the second treatment block, is carried out when the plants are in the growth stage 41 to 92 or even after harvest, i.e. 41 to 99. The most suitable point of time for the treatment depends, inter alia, from the plant to be treated. More detailed information is given below with respect to specific plants.

In the following, specific plants and the respectively preferred time interval for the preferred two treatment blocks are compiled by way of example:

between the single applications depends, inter alia, on the pest pressure, the plant to be treated, weather conditions and can be determined by the skilled person. In general, the application frequency as well as the application rates will correspond to what is customary for the respective plant and the respective host defense inducer under the given conditions, with the exception that after a specific growth stage the treatment with the host defense inducer is replaced by a treatment with a biological control agent. If there is more than one application of the at least one host defense inducer, these may be carried out during different growth stages.

In the method of the invention, depending on the type of host defense inducer used, the single application rates of the at least one host defense inducer are from 0.0001 to 7 kg per ha, preferably from 0.005 to 5 kg per ha, more preferably from 0.05 to 2 kg per ha.

In the treatment block in which the at least one biological control agent is used, this is applied at least once, for example 1, 2, 3, 4, 5, 6, 7 or 8 times, preferably 1, 2, 3, 4, 5 or 6 times, more preferably 1, 2, 3 or 4 times, even more preferably 2, 3 or 4 times and in particular 2 or 3 times. Like in the case of the application of host defense inducers, the application frequency depends, inter alia, on the pathogen pressure and/or on climatic conditions. For instance, weather conditions which promote bacterial attack and proliferation, such as extreme wetness, might require more applications of the biological control agent than dry and hot weather. If there is more than one application of the biological control agent, the time interval between the single applications depends, inter alia, on the pest pressure, the plant to be treated, weather conditions etc., and can be determined by

| Plant | 1$^{st}$ treatment block (host defense inducer) [GS*] | 2$^{nd}$ treatment block (biological control agent) [GS*] |
|---|---|---|
| Grape | finished latest in GS 81, preferably latest in GS 75; preferably 19-75 | starting earliest in GS 65, e.g. 65 through harvest period (89-92) |
| potatoes, vegetables with finished atest in GS 69; starting earliest in GS 69, long vegetation period, e.g. tomatoes, cucumbers, peppers | finished latest in GS 69; preferably 12-69 | starting earliest in GS 69, e.g. 69 through harvest period (89-92) |
| pomefruit, stonefruit, tree nuts | finished latest in GS 69; preferably 01-69 | starting earliest in GS 69, e.g. 69 through harvest period (89-92) |
| strawberry | finished latest in GS 69; preferably 55-69 | starting earliest in GS 71 and continuing during harvestperiod |

*GS = growth stage

In a specific embodiment, all treatment blocks which comprise the treatment with at least one host defense inducer end latest at the end of the vegetative period of the respective plant. In other words, in this specific embodiment no host defense inducer is used for treating the plants after the end of the vegetative period. In this specific embodiment the treatment step with the at least one biological control agent is carried out after the vegetative period in the pre-harvest period. In the treatment block in which the at least one host defense inducer is used, this is applied at least once, for example 1, 2, 3, 4, 5, 6, 7 or 8 times, preferably 1, 2, 3, 4 or 5 times. The application frequency depends, inter alia, on the pathogen pressure and/or on climatic conditions. For instance, weather conditions which promote bacterial attack and proliferation, such as extreme wetness, might require more applications of the at least one host defense inducer than dry and hot weather. If there is more than one application of the host defense inducers, the time interval the skilled person. In general, the application frequency as well as the application rates will correspond to what is customary for the respective plant and the respective biological control agent under the given conditions, with the exception that the treatment with the biological control agent starts only after the plant has reached a specific growth stage and after the treatment with a host defense inducer has been completed. If there is more than one application of the biological control agent, these may be carried out during different growth stages.

A further preferred method according to the present invention comprises subjecting the plants to two or more sequential treatment block as described herein and further to at least one treatment with at least one compound (C) as defined herein. An even more preferred method according to the present invention comprises subjecting the plants to two or more sequential treatment block as described herein and further to at least one treatment with at least one compound (C) as defined herein, with the proviso that the last treatment block comprises subjecting the plants to at least one treatment with at least one biological control agent and optionally the at least one further compound (C). In such embodiment the biological control agents are not necessarily applied after the host defense inducer but may be applied after the at least one further compound (C), too. Concretely, the three components (A), (B) and (C) may be applied in any order and therein each in any differing repeat of treatments. More preferred, the three components (A), (B) and (C) may be applied in any order and therein each in any differing repeat of treatments, with the proviso that the last (final) treatment block comprises subjecting the plants to at least one treatment with at least one biological control agent (and no host defense inducer and no further compound (C)). This means, that the method may comprise at least two repeated treatment blocks of either compound (A), (B) and/or (C), too. In general, the application frequency as well as the application rates and repeats of either compound (A), (B) and/or (C) will correspond to what is customary for the respective plant and the respective compounds (A), (B) and (C) under the given conditions, with the exception that the treatment with either compound (A), (B) or (C) starts only after the plant has reached a specific growth stage and after the application of any previous treatment block has been completed. If there is more than one application of the compounds (A), (B) and (C), these may be carried out during different growth stages.

The methods described herein all encompass the treatment of transgenic plants.

According to the present invention, a synergistic effect of e.g. host defense inducers or the biological control agent is always present when the activity of the active compound combinations exceeds the total of the activities of the active compounds when applied individually. The expected activity for a given combination of two active compounds (binary combination) can be calculated as follows:

$$E = x + y - \frac{x * y}{100}$$

in which E represents the expected percentage of inhibition of the disease for the combination of two compounds at defined doses (for example equal to x and y respectively), x is the percentage of inhibition observed for the disease by the compound (A) at a defined dose (equal to x), y is the percentage of inhibition observed for the disease by the compound (B) at a defined dose (equal to y). When the percentage of inhibition observed for the combination is greater than E, there is a synergistic effect.

The expected activity for a given combination of three active compounds (ternary combination) can be calculated as follows:

$$E = X + Y + Z - \left(\frac{X \cdot Y + X \cdot Z + Y \cdot Z}{100}\right) + \frac{X \cdot Y \cdot Z}{10000}$$

wherein
X is the efficacy when active compound A is applied at an application rate of m ppm (or g/ha),
Y is the efficacy when active compound B is applied at an application rate of n ppm (or g/ha),
Z is the efficacy when active compound C is applied at an application rate of r ppm (or g/ha),
E is the efficacy when the active compounds A, B and C are applied at application rates of m, n and r ppm (or g/ha), respectively.

The degree of efficacy, expressed in % is denoted. 0% means an efficacy which corresponds to that of the control while an efficacy of 100% means that no disease is observed.

If the actual activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in Neth. J. Plant Path., 1964, 70, 73-80).

In a preferred embodiment of the present invention relates to the use of a combination in tomatoes, wherein
(A) the host defense inducer is isotianil,
(B) the biological control agent is selected from the group consisting of
1) bacteria consisting of *Bacillus subtilis* strain QST713/AQ713 (NRRL Accession No. B21661), *Bacillus subtilis* strain AQ 153 (NRRL Accession No. 55614), *Bacillus* sp. strain AQ 175 (ATCC Accession No. 55608), *Bacillus* sp. strain AQ 177 (ATCC Accession No. 55609), and *Bacillus* sp. strain AQ178 (ATCC Accession No. 53522); and
2) Bacteria consiting of *Pseudomonas syringae* pv. tomato, and
(C) at least one further compound is selected from the group consisting of penflufen.

In another preferred embodiment of the present invention relates to the use of a combination as seed treatment in potatoes, wherein
(A) the host defense inducer is isotianil,
(B) the biological control agent is selected from the group consisting of
1) bacteria consisting of *Bacillus subtilis* strain QST713/AQ713 (NRRL Accession No. B21661), *Bacillus subtilis* strain AQ 153 (NRRL Accession No. 55614), *Bacillus* sp. strain AQ 175 (ATCC Accession No. 55608), *Bacillus* sp. strain AQ 177 (ATCC Accession No. 55609), and *Bacillus* sp. strain AQ178 (ATCC Accession No. 53522); and
2) Bacteria consiting of *Streptomyces scabies*, and
(C) at least one further compound is selected from the group consisting of penflufen.

Example 1

The advanced anti-bacterial activity of the active compound combinations according to the invention is evident from the example below. While the individual active compounds exhibit weaknesses with regard to the anti-bacterial activity, the combinations have an activity which exceeds a simple addition of activities.

A synergistic effect of bactericides is always present when the anti-bacterial activity of the active compound combinations exceeds the total of the activities of the active compounds when applied individually. The expected activity for a given combination of two active compounds can be calculated as indicated above, The degree of efficacy, expressed in % is denoted. 0% means an efficacy which corresponds to that of the control while an efficacy of 100% means that no disease is observed.

If the actual anti-bacterial activity exceeds the calculated value, then the activity of the combination is superadditive, i.e. a synergistic effect exists. In this case, the efficacy which was actually observed must be greater than the value for the expected efficacy (E) calculated from the abovementioned formula.

The invention is illustrated by the following example. However the invention is not limited to the example.

Example 1: In Vivo Preventive Test on *Pseudomonas syringae* pv. Tomato (Tomatoes)

Solvent: deionized water
tested compounds: Isotianil (SC200 formulation) at 200/100/50 g a.i./ha
   Acibenzolar-S-methyl (Bion WG50) at 20/10/5 g/ha
   Serenade Max (Dried *Bacillus subtilis* QST 713 strain/WP/14.6%) 6/3/1.2 g/ha To test for preventive activity, young plants are sprayed with the prepared compounds at three different rates of application. One week after application, the plants are inoculated with an aqueous suspension of *Pseudomonas syringae* pv. tomato. Inoculated plants are placed in a greenhouse chamber at 25° C. at a relative atmospheric humidity of 90%.

The test is evaluated 1 week after inoculation. 0% means an efficacy which corresponds to that of the untreated control while an efficacy of 100% means that no disease is observed.

The table below clearly shows that the observed activity of the active compound combination according to the invention is greater than the calculated activity, i.e. a synergistic effect is present.

TABLE in vivo preventive test on *Pseudomonas syringae* pv. tomato (tomatoes)

| Active compounds | Application rate of compound | Efficacy in % found* | calc.** |
|---|---|---|---|
| (A.2) Isotianil | 200 g a.i. | 0 | |
| (B.1) Serenade Max | 6 g product | 5 | |
| (A.2) + (B.1) 1:1 | 200 g + 6 g | 31 | 5 |
| (A.2) Isotianil | 100 g a.i. | 0 | |
| (B.1) Serenade Max | 1.2 g product | 16 | |
| (A.2) + (B.1) 1:1 | 100 g + 1.2 g | 48 | 16 |
| (A.2) Isotianil | 50 g a.i. | 6 | |
| (B.1) Serenade Max | 6 g product | 5 | |
| (A.2) + (B.1) 1:1 | 50 g + 6 g | 46 | 10 |
| (A.1) Bion | 20 g a.i. | 21 | |
| (B.1) Serenade Max | 6 g product | 5 | |
| (A.2) + (B.1) 1:1 | 20 g + 6 g | 51 | 24 |
| (A.1) Bion | 20 g a.i. | 21 | |
| (B.1) Serenade Max | 3 g product | 5 | |
| (A.2) + (B.1) 1:1 | 20 g + 3 g | 39 | 24 |
| (A.1) Bion | 20 g a.i. | 21 | |
| (B.1) Serenade Max | 1.2 g product | 16 | |
| (A.2) + (B.1) 1:1 | 20 g + 1.2 g | 49 | 33 |
| (A.1) Bion | 10 g a.i. | 24 | |
| (B.1) Serenade Max | 3 g product | 5 | |
| (A.2) + (B.1) 1:1 | 10 g + 3 g | 39 | 28 |
| (A.1) Bion | 5 g a.i. | 24 | |
| (B.1) Serenade Max | 6 g product | 5 | |
| (A.2) + (B.1) 1:1 | 5 g + 6 g | 69 | 28 |
| (A.1) Bion | 5 g a.i. | 24 | |
| (B.1) Serenade Max | 3 g product | 5 | |
| (A.2) + (B.1) 1:1 | 5 g + 3 g | 33 | 28 |

*found = activity found
**calc. = activity calculated using Colby's formula

Example 2: In Vivo Preventive (Seed Growth Test) Test on *Streptomyces scabies* (Potato)

Solvent: water
Tested compounds: Isotianil (FS200 formulation) at 30/24/12 ml/100 KG Potato Seed
   Penflufen (Emesto FS240 formulation) at 10 ml/100 KG Potato Seed
   Serenade ASO (*Bacillus subtilis* QST 713 strain/SC/1.34%) 5 Litres/ha (200 ml/area sown under 100 KG Seed)

To test for seed (tuber) treatment activity mixtures of Isotianil FS200 and Serenade ASO SC in combination with an optional further fungicide, ie Potato tubers are selected having reasonable *Streptomyces scabies* infestation. Seed was treated by spray on the tubers with hand knapsack sprayer using total volume of slurry 1500 ml/100 Kg Seed. Seed treatment was done with Isotianil FS 200 alone and in tank-mix with Penflufen.

Serenade ASO SC 1.34% @ 5000 ml/ha of formulated product was sprayed in the furrows just before the sowing of seeds. 100 KG seeds are sown on an area of 400 m² and Serenade ASO @ 200 ml formulated product was used in this test. Seed treated with Isotianil and optional Penflufen as method described above was used in combination with soil application of Serenade ASO in furrows before sowing. This study was conducted in natural field conditions chamber and observations for *Streptomyces scabies* infestation on potato was taken at the time of harvest.

The test is evaluated at harvest of potato crop. 0% means an efficacy which corresponds to that of the untreated control while an efficacy of 100% means that no disease is observed.

The table below clearly shows the combined product has an improved efficacy against scab while at the same time the "% age Grading" shows a positve effect, ie the amount of larger tubers is increased, wherein the combination of Isotianil with Serenade and Penfluven as additional fungiced is in particular advantageous.

| | | | | % age increase/dicrease over conrol | | | | % age Grading | | |
|---|---|---|---|---|---|---|---|---|---|---|
| Tr. | Product | Dose ml/100 kg seed | 1st app. | No. of Plants/5 meter | No. of stems/meter | Weight of tuber/5 meter | % age Efficacy Scab | Small | medium | Large |
| T1 | UTC (untreated control) | | | | | | | 31% | 36% | 32% |
| T2 | Isotianil 200 FS | 12/100 kg | ST | 3% | 7% | 11% | 68% | 29% | 37% | 34% |
| T3 | Serenade ASO 1.34% SC | 5 ltr/ha | Soil app. Just before sowing | 5% | 8% | −3% | 65% | 26% | 38% | 37% |

| Tr. | Product | Dose ml/ 100 kg seed | 1st app. | No. of Plants/5 meter | No. of stems/ meter | Weight of tuber/5 meter | % age Efficacy Scab | % age Grading Small | medium | Large |
|---|---|---|---|---|---|---|---|---|---|---|
| T4 | | 7.5 ltr/ha | Soil app. Just before sowing | 4% | 9% | 2% | 68% | 23% | 35% | 42% |
| T5 | IST + Serenade | 12 ml & 5 ltr | IST & Pen ST. Serenade soil app. Just before sowing | 2% | 10% | −1% | 63% | 25% | 32% | 43% |
| T6 | PEN + IST + SRD | 10 + 12/ 100 kg + 5 ltr/ha | IST + Pen ST. Serenade soil app. Just before sowing | −3% | 5% | 0% | 74% | 27% | 31% | 43% |

The invention claimed is:

1. A method for controlling harmful bacteria in useful plants comprising treatment of the plants with a combination comprising
    (A) at least one host defense inducer selected from the group consisting of acibenzolar-S-methyl, isotianil, and combinations thereof, and
    (B) at least one biological control agent selected from the group consisting of *Bacillus subtilis* strain QST713/AQ713 having NRRL Accession No. B-21661, *Bacillus subtilis* strain QST30002/AQ30002 having NRRL Accession No. B-50421, and *Bacillus subtilis* strain QST30004/AQ30004 having NRRL Accession No. B-50455,
    wherein combination of the host defense inducer and the biological control agent results in an anti-bacterial synergistic effect and the harmful bacteria are *Pseudomonas* spp. or *Xanthomonas* spp.

2. The method according to claim 1, wherein the host defense inducer is isotianil.

3. The method according to claim 1, wherein the at least one biological control agent (B) is *Bacillus subtilis* strain QST713/AQ713 having NRRL Accession No. B-21661.

4. The method according to claim 1, wherein the harmful bacteria are selected from the group consisting of *Pseudomonas syringae*, *Pseudomonas syringae* pv. *actinidae*, *Pseudomonas syringae* pv. *glycinea*, *Pseudomonas syringae* pv. *lachrymans*, and *Pseudomonas syringae* pv. *tomato*.

5. The method according to claim 1, wherein the harmful bacteria are selected from the group consisting of *Xanthomonas axonopodis*, *Xanthomonas axonopodis* pv. *citri*, *Xanthomonas axonopodis* pv. *glycines*, *Xanthomonas campestris*, *Xanthomonas campestris* pv. *musacearum*, *Xanthomonas campestris* pv. *pruni*, *Xanthomonas campestris* pv. *oryzae*, *Xanthomonas fragariae*, *Xanthomonas transluscens*, and *Xylella fastidiosa Xanthomonas oryzae* pv. *oryzae*.

6. The method according to claim 1, wherein the useful plants are selected from the group consisting of apples, bananas, citrus, kiwi, melons, peaches, pears, pineapple, pome fruit, pomegranate, cabbage, cauliflower, cucumbers, cucurbits, tomatoes, potatoes, wheat, rice and soybeans.

7. The method according to claim 1 for controlling *Xanthomonas campestris* pv. *oryzae* in rice, *Xanthomonas axonopodis* pv. *citri* in citrus, *Pseudomonas syringae* pv. *actinidae* in Kiwi, *Xanthomonas campestris* and/or *Xanthomonas campestris* pv. *pruni* in peaches, *Pseudomonas syringae* pv. *glycinea* and/or *Xanthomonas axonopodis* pv. *glycines* in soybeans, *Xanthomonas transluscens* in cereals, *Pseudomonas syringae*, *Pseudomonas syringae* pv. tomato and/or *Xanthomonas campestris* in tomatoes, and/or *Pseudomonas syringae* and/or *Pseudomonas syringae* pv. *lachrymans* in cucumbers.

8. The method according to claim 1, wherein the combination comprising (A) at least one host defense inducer and (B) at least one biological control agent further comprises
    at least one compound (C) selected from the group consisting of fosetyl-Al; aluminium ethyl phosphite; penflufen; acetamiprid, chlothianidin, imidacloprid, thiacloprid, betacyfluthrin, deltamethrin, flupyradifurone, spirotetramat, spiromesifen, spirodiclofen; copper hydroxide, copper sulphate, propineb, mancozeb; lipochito-oligosaccharide compounds (LCO); kasugamycin, streptomycin, and oxytetracyclin.

9. The method according to claim 8, wherein
    the host defense inducer (A) is isotianil,
    the biological control agent (B) is *Bacillus subtilis* strain QST713/AQ713 (NRRL Accession No. B-21661 and
    the at least one further compound (C) is selected from the group consisting of fosetyl-Al; aluminium ethyl phosphite; trifloxystrobin; imidacloprid, thiacloprid, betacyfluthrin, deltamethrin, flupyradifurone, kasugamycin, streptomycin, and oxytetracyclin.

10. The method according to claim 8, wherein compound (C) is penflufen.

11. The method according to claim 1, wherein the host defense inducer is acibenzolar-S-methyl.

12. The method according to claim 6, wherein the treated plant is tomato or potato.

13. The method according to claim 4, wherein the harmful bacteria is *Pseudomonas syringae* pv. tomato.

14. The method according to claim 7, wherein the treated plant is rice and the harmful bacteria is *Xanthomonas campestris* pv. *oryzae*.

15. A method for controlling harmful bacteria in useful plants, which method comprises subjecting plants to be protected against attack by phytopathogenic bacteria to two or more sequential treatment blocks,
    where at least one treatment block comprises subjecting the plants to at least one treatment with at least one host defense inducer (A) selected from the group consisting of acibenzolar-S-methyl, isotianil, and combinations thereof, and
    at least one treatment block comprises subjecting the plants to at least one treatment with at least one biological control agent (B) selected from the group consisting of *Bacillus subtilis* strain QST713/AQ713 having NRRL Accession No. B-21661, *Bacillus subtilis* strain QST30002/AQ30002 having NRRL Accession No. B-50421, and *Bacillus subtilis* strain QST30004/ AQ30004 having NRRL Accession No. B-50455, with the proviso that the last treatment block comprises subjecting the plants to at least one treatment with a combination of the at least one host defense inducer (A) and the at least one biological control agent (B), wherein combination of the host defense inducer and the biological control agent results in an anti-bacterial synergistic effect and the harmful bacteria are *Pseudomonas* spp. or *Xanthomonas* spp.

16. The method according to claim 15 further comprising subjecting the plants to at least one treatment with at least one compound (C) selected from the group consisting of fosetyl-Al; aluminium ethyl phosphite; penflufen; trifloxystrobin; acetamiprid, chlothianidin, imidacloprid, thiacloprid, betacyfluthrin, deltamethrin, flupyradifurone, spirotetramat, spiromesifen, spirodiclofen; copper hydroxide, copper sulphate, propineb, mancozeb; lipochito-oligosaccharide compounds (LCO); kasugamycin, streptomycin, and oxytetracyclin.

17. The method according to claim 15, wherein the respective treatment blocks are carried out during different growth stages of the plants.

* * * * *